US012714480B2

(12) United States Patent
Caldarella et al.

(10) Patent No.: US 12,714,480 B2
(45) Date of Patent: Aug. 25, 2026

(54) BONE FUSION/FIXATION DEVICE AND RELATED METHODS

(71) Applicant: ExoToe LLC, Johnston, IA (US)

(72) Inventors: David Caldarella, Barrington, RI (US); Michael Lee, Johnston, IA (US); Shannon Rush, San Jose, CA (US); Jordan Grossman, Akron, OH (US); John Roop, Scottsdale, AZ (US); Christopher Pell, San Francisco, CA (US)

(73) Assignee: ExoToe LLC, Johnston, IA (US)

( * ) Notice: Subject to any disclaimer, the term of this patent is extended or adjusted under 35 U.S.C. 154(b) by 324 days.

(21) Appl. No.: 18/586,013

(22) Filed: Feb. 23, 2024

(65) Prior Publication Data

US 2024/0189004 A1 Jun. 13, 2024

Related U.S. Application Data

(63) Continuation-in-part of application No. 29/828,153, filed on Feb. 24, 2022, now Pat. No. Des. 1,046,144, which is a continuation-in-part of application No. 17/103,279, filed on Nov. 24, 2020, now Pat. No. 11,660,131, which is a continuation of application No. 16/114,391, filed on Aug. 28, 2018, now Pat. No. 10,849,664, which is a continuation of application No. 15/121,238, filed as application No. PCT/US2015/018111 on Feb. 27, 2015, now Pat. No. 9,878,857, application No. 18/586,013, filed on Feb. 23, 2024 is a continuation-in-part of application No.

(Continued)

(51) Int. Cl.

| | |
|---|---|
| *A61B 17/80* | (2006.01) |
| *A61B 17/064* | (2006.01) |
| *A61B 17/72* | (2006.01) |
| *A61B 17/82* | (2006.01) |
| *A61B 17/88* | (2006.01) |

(52) U.S. Cl.

CPC ........ *A61B 17/8061* (2013.01); *A61B 17/064* (2013.01); *A61B 17/0644* (2013.01); *A61B 17/7291* (2013.01); *A61B 17/808* (2013.01); *A61B 17/8085* (2013.01); *A61B 17/809* (2013.01); *A61B 17/82* (2013.01); *A61B 17/8863* (2013.01); *A61B 2017/0641* (2013.01); *A61B 17/8009* (2013.01)

(58) Field of Classification Search

CPC .................................................. A61B 17/8061

See application file for complete search history.

(56) References Cited

U.S. PATENT DOCUMENTS 3,593,709 A * 7/1971 Halloran ............ A61B 17/8061 52/514

5,586,985 A * 12/1996 Putnam ................ A61B 17/809 606/904

(Continued)

*Primary Examiner* — Christian A Sevilla

(74) *Attorney, Agent, or Firm* — ZarleyConley PLC

(57) ABSTRACT

The various aspects disclosed herein relate to bone fixation or fusion devices, including fixation or fusion devices that are implanted around the target bone. Certain device aspects relate to devices that can be bent or otherwise deformed to replicate the natural or desired curve of the bone being treated. In addition, other aspects relate to implantation devices that can be used to implant or position the bone fixation or fusion devices. Aspects related to the making of the device and its use are discussed.

23 Claims, 40 Drawing Sheets

Related U.S. Application Data

29/849,835, filed on Aug. 15, 2022, now Pat. No. Des. 1,039,150, and a continuation-in-part of application No. 29/849,840, filed on Aug. 15, 2022, now Pat. No. Des. 1,039,151, and a continuation-in-part of application No. 29/849,841, filed on Aug. 15, 2022, now Pat. No. Des. 1,039,695.

(56) References Cited

U.S. PATENT DOCUMENTS

| | | | | |
|---|---|---|---|---|
| 2003/0105461 | A1* | 6/2003 | Putnam .............. | A61B 17/8033<br>606/104 |
| 2004/0153073 | A1* | 8/2004 | Orbay ................ | A61B 17/8057<br>606/291 |
| 2009/0198285 | A1* | 8/2009 | Raven, III ......... | A61B 17/8061<br>606/280 |
| 2020/0054374 | A1* | 2/2020 | Schumacher ...... | A61B 17/8061 |

* cited by examiner

BONE FUSION/FIXATION DEVICE AND RELATED METHODS

CROSS REFERENCE TO RELATED APPLICATION

This application claims priority as a continuation-in-part to U.S. application Ser. No. 29/828,153, filed on Feb. 24, 2022 and entitled "Bone Fusion/Fixation Device," which claims priority as a continuation-in-part to U.S. application Ser. No. 17/103,279, filed on Nov. 24, 2020 and entitled "Bone Fusion/Fixation Device and Related Systems and Methods," now U.S. Pat. No. 11,660,131, which claims priority as a continuation to U.S. application Ser. No. 16/114,391, filed on Aug. 28, 2018 and entitled "Bone Fusion/Fixation Device and Related Systems and Methods," now U.S. Pat. No. 10,849,644, which claims priority as a continuation to U.S. application Ser. No. 15/121,239, filed on Aug. 24, 2016 and entitled "Bone Fusion/Fixation Device and Related Systems and Methods," now U.S. Pat. No. 10,080,599, which claims the benefit under 35 U.S.C. § 371 to International PCT Patent Application No. PCT/US15/18111, filed on Feb. 27, 2015.

This application also claims priority as a continuation-in-part to U.S. application Ser. No. 29/849,835, filed Aug. 15, 2022 and entitled "Bone Fixation/Fusion Device."

This application also claims priority as a continuation-in-part to U.S. application Ser. No. 29/849,840, filed Aug. 15, 2022 and entitled "Bone Fixation/Fusion Device."

This application also claims priority as a continuation-in-part to U.S. application Ser. No. 29/849,841, filed Aug. 15, 2022 and entitled "Bone Fixation/Fusion Device."

All of the preceding are hereby incorporated herein by reference in their entireties.

FIELD OF INVENTION

The various embodiments disclosed herein relate to bone fixation or fusion devices, including fixation or fusion devices for extramedullary fixation of the metatarsal, metacarpal, and phalangeal bone, such as for use in a long bone osteotomy or fracture of the foot or hand.

BACKGROUND OF THE INVENTION

Bone fracture repair is a common surgical procedure for bone repair as are osteotomies for curing and reshaping bones to correct bone alignment.

Fractures of the phalanges, metatarsal, and metacarpals inherently result in varied patterns based on the injury forces in play. These patterns can be transverse, oblique, comminuted, or a combination of any of the preceding. Historically, surgical repair involves fixation of the fracture pattern using pins, screws, plates, external frame fixation devices, or a combination of any of these depending on the nature of the fracture. These repairs are directed at stabilizing the fracture and restoring the anatomic shape.

Fracture reduction and fixation of the long bones of the foot and hand can be challenging due to limited access provided by the confined space of such portions of the body. Due to this, the surgical approach is directed at the dorsal surface of the hand or foot to avoid scarring the palm of the hand or the bottom of the foot. While useful in the preservation of soft tissue, it fails to provide optimal exposure for the medial, lateral, or plantar fracture fragments of the injured bone or bones.

Prior to the creation of the various embodiments disclosed herein, bone fractures have been commonly repaired by the application of a Kirschner wire ("K-wire") or pin. The use for K-wire is depicted in FIG. 1A, which depicts a K-wire positioned in a digit to repair a transverse fracture. The K-wire provides for quick application as it is often driven through the skin in a percutaneous manner. In some instances, the K-wire is left external to the skin surface to allow removal after the bone has sufficiently healed. It is common practice to drive the K-wire through the plantar surface of the skin, which is well suited to fix transverse or metacarpal fractures.

Disadvantages of standard K-wire fixation include that one or more such K-wires will protrude from the plantar weightbearing surface for weeks. As is apparent, this poses the risk of inadvertent movement by the patient that can serve as a conduit for skin bacteria that can in turn result in deeper soft tissue infection. K-wires can also be placed externally on the dorsal, medial, or lateral surface where the skin is thinner. Nerves at such locations are at a higher risk of injury. Hence, the external positioning of K-wires and pins are prone to complications related to tissue and nerve irritation, swelling, and postoperative injury. Other disadvantages caused by the external nature of K-wires include limitation of ambulation and secondary events. Accordingly, K-wires are often removed prematurely when one or more of the stated complications arise. As the bone has not sufficiently healed, the fracture is prone to instability and delay in healing or healing at all. Therefore, while K-wires and pins are useful in addressing fracture patterns of the metatarsal and metacarpals given their simplistic form of fixation and practicality, they are a less stable form of fixation and have a higher potential failure rate.

As an alternative to K-wires as an intramedullary fixation device, screw fixation is used alone or in combination with pins or plates. When used alone, complete internal placement is intended. FIG. 1B depicts an embodiment of screw fixation utilized to repair fracture. Use of screw fixation depends on the fracture pattern, access related to the desired angle of insertion, and proximity to adjacent joints. The screws used in screw fixation are typically applied percutaneously through the skin and soft tissues since the dorsal surgical exposure used to reduce the fracture may not allow for desired angle and location of placement. Under desirable conditions, the screw or screws are inserted perpendicular to the fracture line to facilitate compression of the fracture fragments and promote primary bone healing. As such, oblique fracture patterns are highly amenable to screw fixation.

Other complications relate to screw fixation and related solid and cannulated intramedullary devices. These include failure to impart stability, loss of stability, loss of fixation, breakage of device, device loosening, handling and storage constraints due to metallurgy properties, inventory control dissatisfiers, cost, difficulty in removal, bone loss, and secondary procedures, and complications salvaged via explanation. Further, few of the newer intra-medullar technologies are compatible and approved (via 510K clearance) to be used concurrently with Kirschner wire fixation.

Screw fixation requires small stab incisions, which adds the risk of nerve injury. Additionally, transverse fractures are not readily addressed with screws as the screws can cause displacement when tightened. Additional anatomic limitations exist regarding screw insertion. For instance, the third metatarsal hinders lateral to medial screw placement for a second metatarsal fracture. The same applies to metacarpal fractures.

Screw fixation is also not a practical method of repair for small or comminuted fracture fragments. Such zones of fracture fragmentation are commonly addressed in combination with plate fixation such as a bridge plate that secures the stable bone segments on either side of the fragmented zone with multiple screws. Plate fixation has other advantages. For example, plate fixation provides simplified application from the dorsal surface. The plate can also span two or more fracture fragments. FIG. 1C depicts an illustrative example of plate fixation utilized to repair fracture. While a variety of plates are used in plate fixation, only small-sized plates are appropriate for the long bones of the foot and hand.

While plate fixation has a long history, specialized plate sets are not available at all surgical facilities. Even though common fracture patterns exist, every fracture is unique with respect to the fracture lines and orientation, as well as the specification location in relation to adjacent joints and the size of the fracture fragments. Plate fixation is also limited by the location of the plate holes that receive the screws used in screw fixation. The position of the plate holes frequently does not align with the ideal screw placement of a given fracture pattern. As a result, surgeons are required to depart for ideal screw placement to conform to the given plate hole pattern. Another disadvantage of plate fixation and screw fixation is the requirement that drill holes be formed in the fracture fragments. The need for a plate also increases the monetary cost as well as increase the operative time. Moreover, plate fixation is not always practical near a joint.

Comminuted fractures, which involve more than two fracture fragments, are generally less stable and can require shortening and/or angulation of the bone segment. Repair of comminuted fractures often requires distraction of the fracture out to length and provisional pinning prior to the application of a bridge plate as discussed. Due to the small size of the bones of the foot and hand, and the limited dorsal access, repair of this nature is difficult and at times, entirely impractical. As such, plate fixation is often limited to the capture of large bone fragments while the small fracture fragments are left unrepaired. These small fragments are commonly referred to as butterfly fragments. In some instances, butterfly fragments require the additional step and time of circumferentially wrapping them around the bone with suture or stainless-steel wire.

External fixation frames are also known for use with comminuted fractures and in situations where the soft tissue has been significantly compromised. In some such scenarios, a provisionally placed external fixator device is used to stabilize the bone fragments and distract fractures out to length. In instances where the fracture is highly comminuted with many small fragments that are not amenable to plate fixation as discussed, external fixation is used.

As noted herein, external fixation devices are not without risk. The use of percutaneous pin fixation has the disadvantage of potential infection and hardship for the patient given their protruding nature. Additionally, external fixation usually requires a second surgery requiring anesthesia for frame removal, which also carries a significant monetary cost.

Extramedullary devices exist as well for simple fractures. Such devices are designed and sized for toe and joint fusion, and therefore have limited application for complex fractures and osteotomies. The use of extramedullary devices also carries the limitation of preventing the incorporation of additional wires (e.g., olive wire) or screw fixation.

Metatarsal osteotomy procedures involve surgical bone cuts that are undertaken to shorten a bone, correct a deformity (such as elevating a plantarly displaced bone), or straightening a crooked bone (such as with tailor's bunions). Commonly, the osteotomy is temporarily held in place by a pin and fixated with one or more screws alone or in conjunction with plate fixation. Screw fixation is generally limited to oblique, whereas flat-cut osteotomies usually require plate fixation.

Central metatarsal fractures and osteotomies generally fixate from the dorsal surface due to limited medial and lateral access (and no plantar access) as discussed. Accordingly, there is limited ability to capture comminuted fracture fragments.

There is a need in the art for an improved extramedullary device designed specifically for bone fracture repair and osteotomy.

SUMMARY OF THE INVENTION

Discussed herein are various bone fusion or fixture devices and related systems and methods.

In Example 1, a bone fusion/fixation device comprises at least one spine, at least two proximal arms extending from the proximal end of the at least one spine, two distal arms extending from a distal end of the at least one spine, and at least two medial arms extending between the at least two proximal arms and the at least two distal arms.

Example 2 relates to the bone fusion/fixation device according to Example 1, further comprising at least one opening defined in the bone fixation device, wherein the opening is sized and shaped to receive a portion of an implantation tool.

Example 3 relates to the bone fusion/fixation device according to Example 1, further comprising each of the at least two medial arms comprising at least one deformation feature that is configured to facilitate deformation of the at least two medial arms.

Example 4 relates to the bone fusion/fixation device according to Example 1, wherein the at least one medial tine is positioned at a radius of curvature that is more acute than a radii of curvature within the at least two medial arms.

Example 5 relates to the bone fusion/fixation device according to Example 1, wherein the at least one spine comprises a first spine and a second spine that each have an inner curved edge.

Example 6 relates to the bone fusion/fixation device according to Example 5, further comprising the inner curved edge of the first spine and the second spine extending from a spine corner that are configured to facilitate stability and are radiused to prevent fatigue fracture of the at least one spine.

Example 7 relates to the bone fusion/fixation device according to Example 1, further comprising the at least two proximal arms comprising at least one proximal mid tine positioned proximally on the at least two proximal arms.

Example 8 relates to the bone fusion/fixation device according to Example 1, further comprising the at least two distal arms comprising at least one distal mid tine positioned distally on the at least two distal arms.

Example 9 relates to the bone fusion/fixation device according to Example 1, comprising the at least two medial arms comprising at least one tool interface feature.

Example 10 relates to the bone fusion/fixation device according to Example 1, further comprising the bone fusion/fixation device positioned over a target site. The target site is selected from a group consisting of an osteotomy of the bone and a fracture of the bone. The bone is selected from a group consisting of the bone of a foot, a digital bone of the foot, a long bone of the foot, the bone of a hand, the digital bone of the hand, and the long bone of the hand.

Example 11 relates to the bone fusion/fixation device according to Example 1, wherein the at least two proximal arms extend outwardly in an acute angle formed by the at least one spine and each of the at least two proximal arms, respectively. The at least two proximal arms extend proximally forward of the proximal end of the at least one spine.

Example 12 relates to the bone fusion/fixation device according to Example 1, wherein the at least two distal arms extend outwardly in an acute angle formed by the at least one spine and each of the at least two distal arms, respectively. The at least two distal arms extend distally forward of the distal end of the at least one spine.

Example 13 relates to the bone fusion/fixation device according to Example 1, further comprising at least two second medial arms extending from the at least one spine between the at least two distal arms and the at least two medial arms. Each of the at least two second medial arms comprising at least one second medial tine, wherein the at least two second medial arms are configured to be positionable around the bone.

Example 14 relates to the bone fusion/fixation device according to Example 1, wherein the at least two proximal arms and the at least two distal arms extend a first distance away from the at least one spine, and the at least two medial arms and the at least two second medial arms extend a second distance away from the at least one spine. The first distance and the second distance are not equal.

In Example 15, a bone fusion/fixation method comprises providing a bone fusion/fixation device that comprises (a) at least one comprises at least one spine, (b) at least one proximal structure extending from a proximal end of the at least one spine, the at least one proximal structure comprising at least one proximal tine, (c) at least one distal structure extending from a distal end of the at least one spine, the at least one distal structure comprising at least one distal tine, and (d) at least one medial structure extending from the at least one spine between the at least one proximal structure and the at least one distal structure, wherein the at least one medial structure comprising at least one medial tine, wherein the at least one medial structure is configured to be positionable around the bone. The at least one proximal structure, distal structure, and medial structure are each configured to be positionable around a bone. The method also comprises positioning the at least one proximal structure, the at least one distal structure, and the at least one proximal structure around a target site of the bone. Additionally, the method comprises crimping the bone fusion/fixation device with an application tool such that the at least one proximal tine, the at least one distal tine, and the at least one distal tine are urged into the bone. The bone is a single bone, rather than bones joined by a joint, that are fixed about the target site with the fusion/fixation device in a desired anatomical alignment.

Example 16 relates to the method of bone fusion/fixation according to Example 15, wherein the target site is selected from a group consisting of an osteotomy of the bone and a fracture of the bone. The bone is selected from a group consisting of the bone of a foot, a digital bone of the foot, a long bone of the foot, the bone of a hand, the digital bone of the hand, and the long bone of the hand.

Example 17 relates to the method of bone fusion/fixation according to Example 15, further comprising (e) at least one arm deformation feature defined in at least one of the at least one medial structure that is configured to facilitate deformation of the at least one medial structure.

Example 18 relates to the method of bone fusion/fixation according to Example 15, further comprising (e) at least one second medial structure extending from the at least one spine between the at least one medial structure and the at least one distal structure, wherein the at least one second medial structure comprising at least one second medial tine. The at least one second medial structure is configured to be positionable around the bone.

Example 19 relates to the method of bone fusion/fixation according to Example 18, wherein the at least one proximal structure and the at one distal structure extend a first distance away from the at least one spine, and the at least one medial structure and the at least one second medial structure extend a second distance away from the at least one spine. The first distance and the second distance are not equal.

Example 20 relates to the method of bone fusion/fixation device according to Example 15, wherein the at least one proximal structure extends outwardly in an acute angle formed by the at least one spine and the at least one proximal structure and the at least one proximal structure extends proximally forward of the proximal end of the at least one spine. The at least one distal structure extends outwardly in an acute angle formed by the at least one spine and the at least one distal structure and the at least one distal structure extends distally forward of the distal end of the at least one spine.

In Example 21, a method of making a bone fusion/fixation device comprises forming a flat structure of bendable material. The flat structure comprises: (a) at least one spine, (b) at least one proximal structure having at least one proximal tine and extending from a proximal end of the at least one spine (c) at least one distal structure having at least one distal tine and extending from a distal end of the at least one spine, and (d) at least one medial structure having at least one medial tine and extending from the at least one spine between the at least one proximal structure and the at least one distal structure. The method also comprises deforming the at least one medial tine such that the at least one medial tine is disposed at an angle greater than 0 degrees in relation to the at least one medial structure.

Example 22 relates to the method of making a bone fusion/fixation device according to Example 21, further comprising (e) at least one second medial structure having at least one second medial tine and extending from the at least one spine between the at least one medial structure and the at least one distal structure.

Example 23 relates to the method of making a bone fusion/fixation device according to Example 21, further comprising (e) at least one opening defined in the flat structure, wherein the opening is sized and shaped to receive a portion of an application tool.

This has outlined, rather broadly, the features, advantages, solutions, and benefits of the disclosure in order that the description that follows may be better understood. Additional features, advantages, solutions, and benefits of the disclosure will be described in the following. It should be appreciated by those skilled in the art that this disclosure may be readily utilized as a basis for modifying or designing other structures and related operations for carrying out the same purposes of the present disclosure. It should also be realized by those skilled in the art that such equivalent constructions and related operation do not depart from the teachings of the disclosure as set forth in the appended claims. The novel features, together with further objects and advantages, will be better understood from the following description when considered in connection with the accompanying Figures. It is to be expressly understood, however, that each of the Figures is provided for the purpose of illustration and description only and is not intended as a definition of the limits of the present disclosure.

DETAILED DESCRIPTION

Figure 1A:
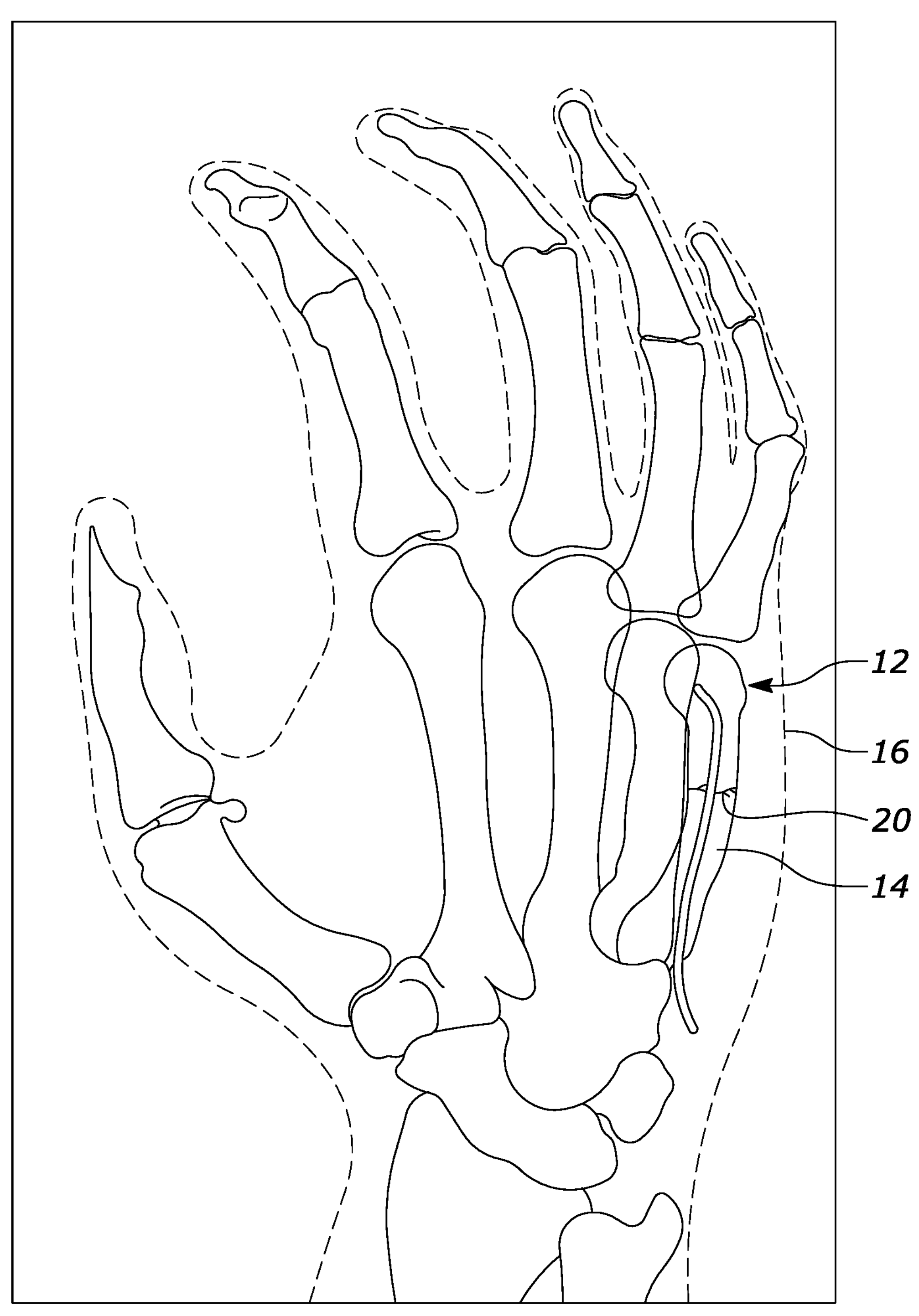
FIG. 1A is a front view of an X-ray of a known K-wire device positioned in an affected digit.

The disclosure described herein is directed to different aspects of a bone fixation device and related systems and methods. The detailed description set forth below, in connection with the appended drawings, is intended as a description of various configurations and is not intended to represent the only configurations in which the concepts described herein may be practiced. These descriptions include specific details for the purpose of providing a thorough understanding of the various concepts. It will be apparent, however, to those skilled in the art that these concepts may be practiced without these specific details.

The various embodiments disclosed and contemplated herein relate to anatomic, site-specific extra-medullary fixation and/or fusion devices (and related systems and methods) designed to achieve satisfactory mechanical and clinical benefit over traditional K-wire fixation and existing and emerging new solid and/or cannulated intramedullary fixation technologies, including those used with over existing plate fixation combined with screw fixation. Certain implementations are designed specifically for fracture repair and osteotomy applications related to the foot (or hand). More specifically, the various embodiments relate to a system comprising an anatomically specific extramedullary digital fixation device and a related application tool.

Aspects, elements, and/or features may be disclosed in relation to a reference numeral ending in "n" (e.g., 30*n*). Such a designation should be understood to refer to similar features present in the Figures that are not specifically set forth in this disclosure for the sake of being concise.

FIGS. 2A-2E depict examples of a fusion/fixation device 10 affixed to various target sites on a bone 12, including a long bone 14 of the hand 16 and foot 18. Each of the examples disclosed herein can be affixed to the target site independently, such that the fusion/fixation device 10 is not present along with any pin or K-wire fixation, screw fixation, or plate fixation post-operation. Alternatively, the fusion/fixation device 10 can be used concurrently with K-wire fixation device or other known devices per clinical need and/or surgeon preference. That is, the aspects disclosed herein are configured to be capable of and compatible with the concurrent use of a K-Wire. Surgeons may elect to adjunctively apply such K-wire adjunct to stabilize and control the position of the bone 12. The various implementations disclosed herein allow such adjunctive use. In contrast, other known technologies as described herein cannot be used in combination with or concurrently with a K-wire.

The various examples and aspects disclosed herein relate to a device of enhanced stability over/against the intended site on the bone 12 over time. In FIGS. 2A-2E, the fusion/fixation device 10 is positioned on the bone 12 over a fracture 20, thereby fixating the fracture to allow the fracture 20 of the bone 12 to heal. The examples and aspects disclosed herein, relate to anatomically specific extramedullary fusion and/or fixation devices that are affixed to the desired target site of a fractured bone, thereby providing an entirely externally-based fixation method construct which provides satisfactory mechanical support to the intended fracture site.

Figure 3:
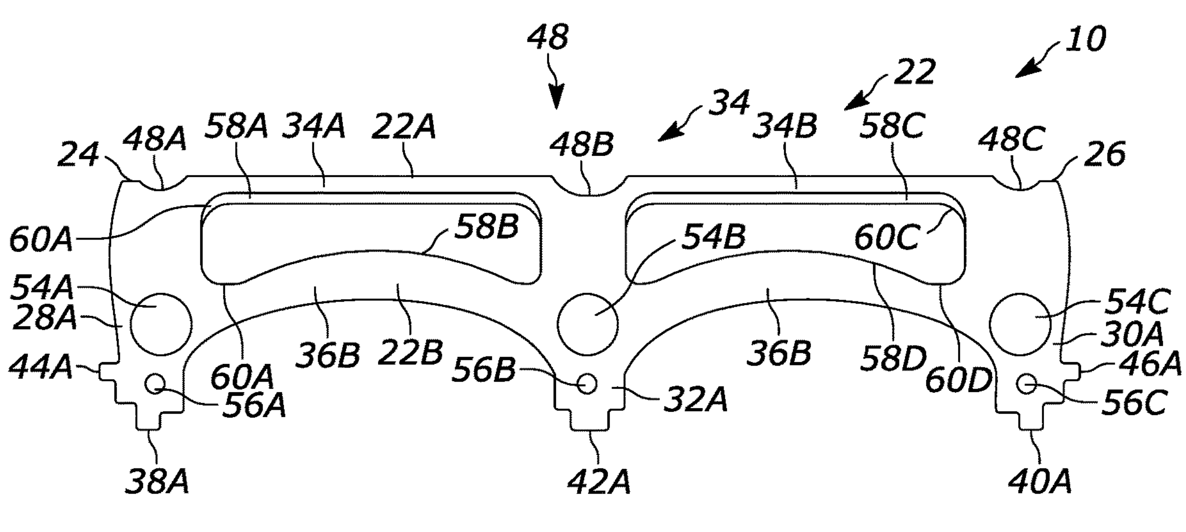
FIG. 3 is a side view of a fusion/fixation device according to an aspect of the disclosure.

FIG. 3 depicts aspects of the fusion/fixation device 10. The fusion/fixation device 10 comprises at least one spine 22, including a first spine 22A and a second spine 22B as shown in FIG. 3, that extends to and between a proximal end 24 and a distal end 26. A pair of proximal arms or structures 28A, 28B is connected at the proximal end 24 (the other arm is not visible in FIG. 3) and a pair of distal arms or structures 30A, 30B is connected to the distal end 26 (the other arm is not visible in FIG. 3). Positioned between the pair of proximal arms 28A, 28B and the pair of distal arms 30A, 30B is a pair of medial arms or structures 32A, 32B that are connected to the at least one spine 22, which in some aspects is equidistantly positioned between the proximal end 24 and the distal end 26. The at least one spine 22 may be separated into two or more spine sections 34. As shown in FIG. 3, the first spine 22A and the second spine 22B are divided into two spine sections 34A, 34B, 36A, 36B. Such an implementation maintains stability over longer fixation distances, which is useful in bone fracture fixation where more than two anchor points are desired.

The pair of proximal arms 28A, 28B may each have at least one tine 38A, 38B (or proximal tine), the pair of distal arms 30A, 30B may each have at least one tine 40A, 40B (or distal tine), and the pair of medial arms 32A, 32B may each have at least one tine 42A, 42B (or medial tine). In other aspects, the pair of proximal arms 28A, 28B may each have at least one mid tine 44A, 44B (or mid proximal tine) and the pair of distal arms 30A, 30B may each have at least one mid tine 46A, 46B (or mid distal tine). In some aspects, the at least one tine 38A, 38B, 40A, 40B, 42A, 42B and/or the at least one mid tine 44A, 44B, 46A, 46B, extend inwardly one another from the respective arm towards an interior of the fusion/fixation device 10. In other aspects, the at least one mid tine 44A, 44B of the pair of proximal arms 28A, 28B is positioned proximally ahead of the proximal end 24 of the at least one spine 22 and the at least one mid tine 46A, 46B is positioned distally ahead of the distal end 26 of the at least one spine 22. The tines, in some aspects, provide additional rotational and torsional stability of the bone 12 with respect to the at least one spine 22

In still other aspects, the at least one spine 22 has at least one opening 48. As depicted in FIG. 3, the at least one spine 22 has a plurality of openings 48A, 48B, 48C, 48*n*. In some aspects, the plurality of openings 48A, 48B, 48C may provide one or more features, including facilitating deformation of the fusion/fixation device 10 and/or mounting the fusion/fixation device 10 to a bone 12.

When one or more of the plurality of openings 48A, 48B, 48C, 48*n* are configured for mounting, an interior circumference of the plurality of openings 48A, 48B, 48C, 48*n* may be threaded to receive a screw 50 (not shown) or application tool 52, as discussed in further detail below. The plurality of openings 48A, 48B, 48C, 48*n* may also be configured for facilitating deformation of the at least one spine 22, as discussed further herein. In other aspects, the plurality of openings 48A, 48B, 48C, 48*n* can provide the surgeon flexibility to adjust the device to specific anatomical bends and incorporate additional fixation devices such as screws and locking screws.

One or more of the arms, including the pair of proximal arms 28A, 28B, the pair of distal arms 30A, 30B, and the pair of medial arms 32A, 32B, may each or all have one or more of a deformation feature 54A, 54B, 54C 54*n* (the features not visible on the opposing side in FIG. 3). The presence of the deformation feature 54A, 54B, 54C, 54*n* makes it easier to deform the respective arm in comparison to an equivalent device without the features. The deformation feature 54A, 54B, 54C, 54*n,* in certain aspects, is configured to have a cross-sectional area designed to preferentially localize deformation within the fusion/fixation device 10 in the area surrounding each of the deformation feature 54A, 54B, 54C, 54*n,* so that the fusion/fixation device 10 more closely approximates the cross section of the target site on the bone 12 when the fusion/fixation device 10 is crimped thereto as discussed further herein. The deformation feature 54A, 54B, 54C, 54*n* can provide the surgeon greater control and leverage when working to push the tines into the bone 12 and wrap the arms around the bone 12.

With continued reference to FIG. 3, one or more of the arms, including the pair of proximal arms 28A, 28B, the pair of distal arms 30A, 30B, and the pair of medial arms 32A, 32B, may each or all have one or more of a tool interface feature 56A, 56B, 56C, 56*n* (the features not visible on the opposing side in FIG. 3). Where present, the tool interface feature 56A, 56B, 56C, 56*n* is configured to couple with the application tool 52, such as a pair of pliers, for purposes of implanting or otherwise positioning the fusion/fixation device 10, as discussed in further detail herein. In some such aspects, the tool interface feature 56A, 56B, 56C, 56*n* are non-circular or comprise multiple openings to prevent rotation when the application tool 52 is coupled thereto.

As seen in FIG. 3, the at least one spine 22 may have an inner curved edge or edges 58A, 58B, 58C, 58D (the edges not visible on the opposing side in FIG. 3), including in aspects having two or more spine sections 34. This configuration facilitates deformation of the at least one spine 22, thereby facilitating the creation of an anatomical 3-D shape as the fusion/fixation device 10 is implanted on the bone 12 of the patient. More specifically, the inner curved edge or edges 58A, 58B, 58C, 58D allow for the at least one spine 22 to be deformed such that the proximal end 24 and the distal end 26 of the fusion/fixation device 10 are urged downward in relation to the middle of the at least one spine 2 more easily than if the at least one spine 22 did not have the inner curved edge or edges 58A, 58B, 58C, 58D. The inner curved edge or edges 58A, 58B, 58C, 58D, in some aspects, may be formed along the plurality of openings 48A, 48B, 48C, 48*n*. The at least one spine 22, in further aspects, may also have one or more spine corner 60A, 60B, 60C, 60D positioned at the terminal ends of the inner curved edge or edges 58A, 58B, 58C, 58D, 58*n*. The one or more spine corner 60A, 60B, 60C, 60D, 60*n* facilitate stability and are radiused to prevent fatigue fracture.

The fusion/fixation device 10 may also comprise a fracture site indicator line 62 (not shown). The fracture site indicator line 62 is configured to facilitate proper positioning and/or alignment of the fusion/fixation device 10 about the fracture 20 of the bone 12.

Figure 4:
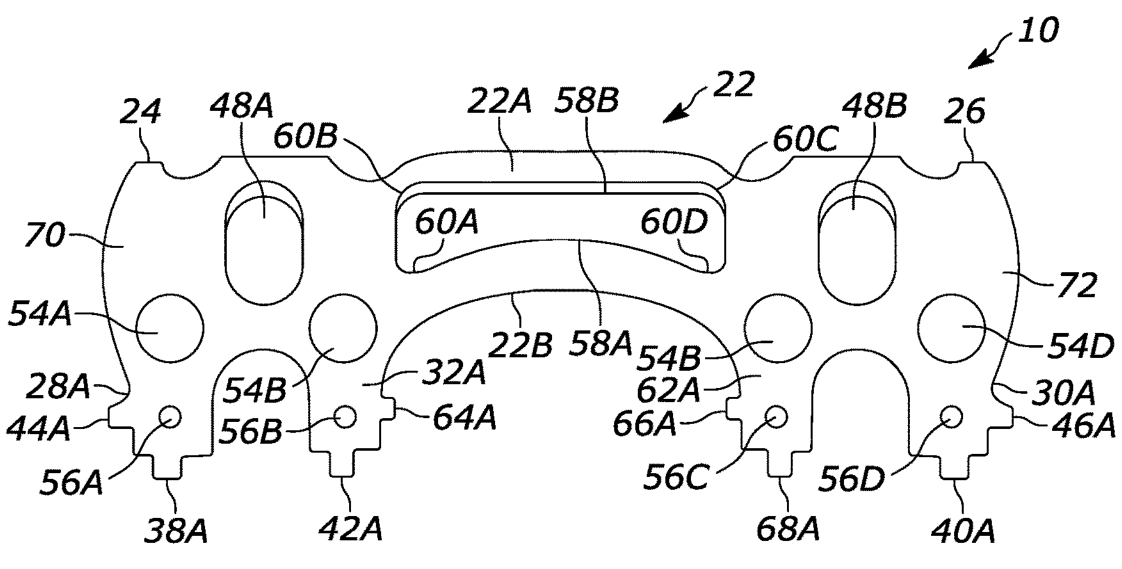
FIG. 4 is a side view of a fusion/fixation device according to an aspect of the disclosure.
Figure 5A:
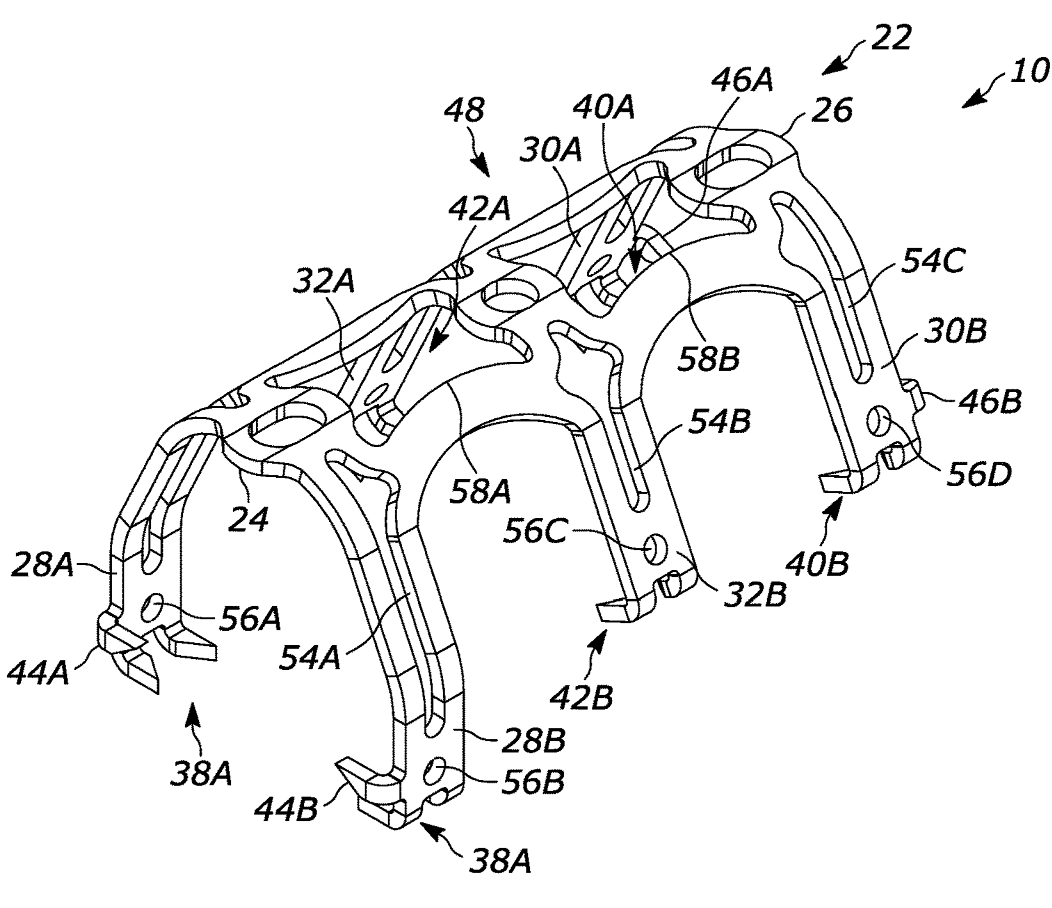
FIG. 5A is a perspective view of a fusion/fixation device according to an aspect of the disclosure.
Figure 5B:
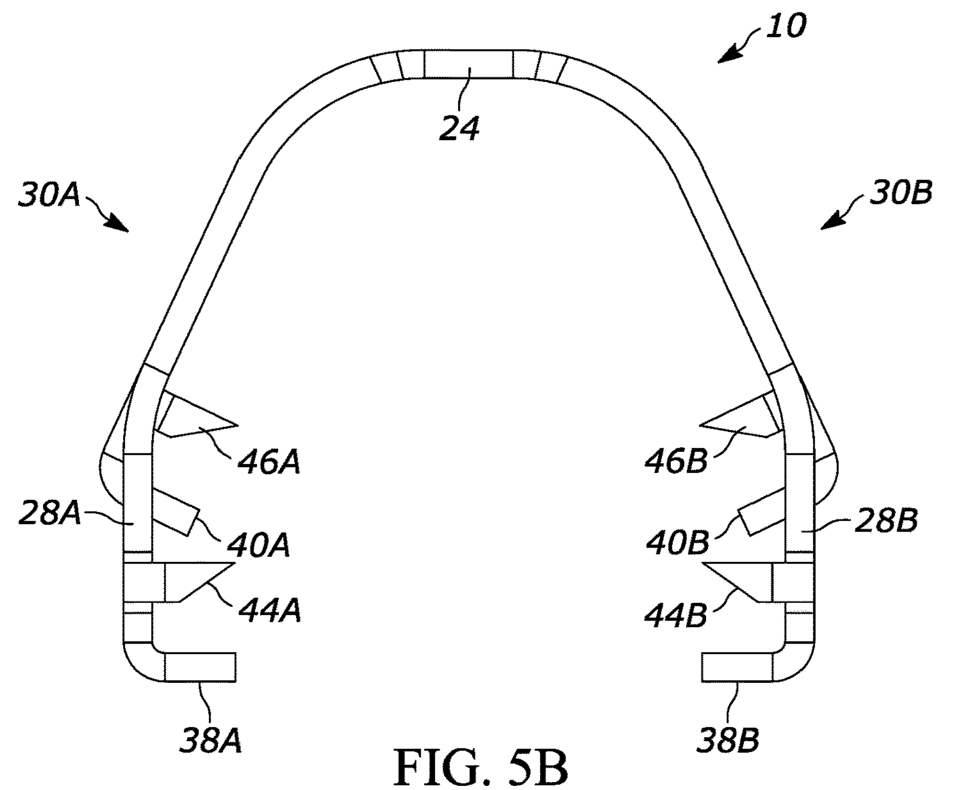
FIG. 5B is a front view of the fusion/fixation device of FIG. 5A.
Figure 5C:
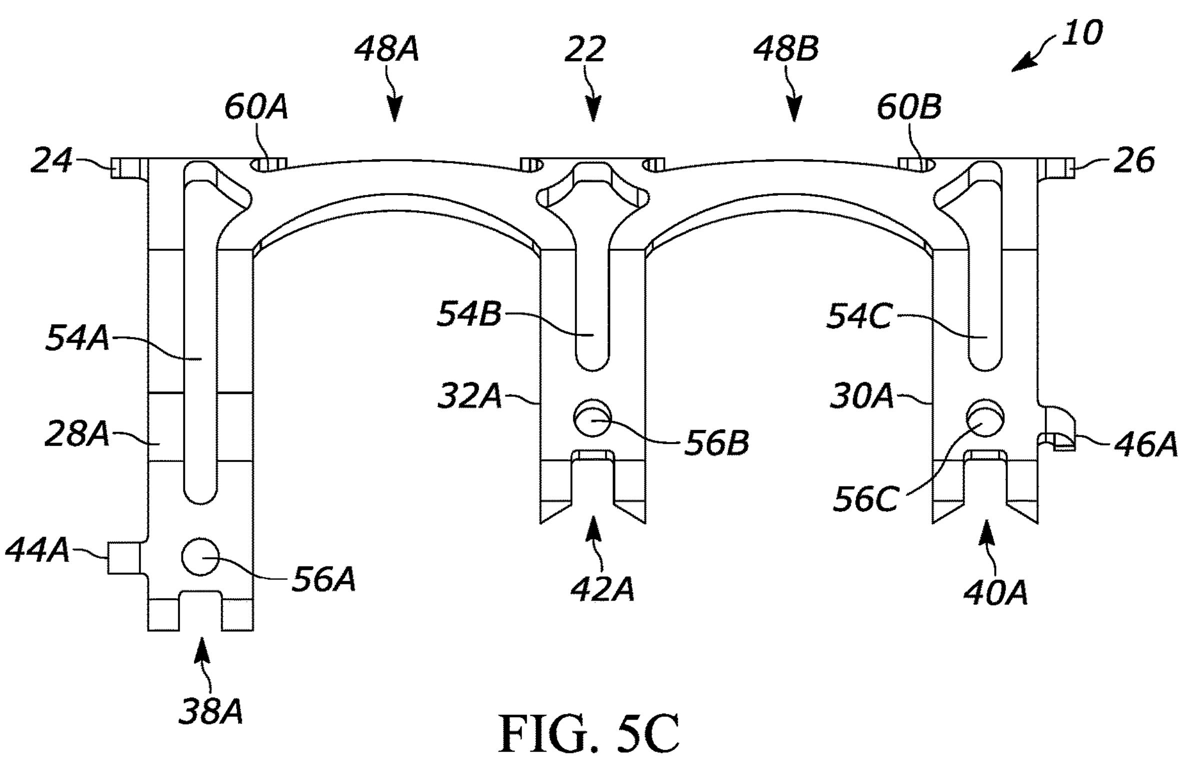
FIG. 5C is a side view of a fusion/fixation device of FIG. 5A.
Figure 5D:
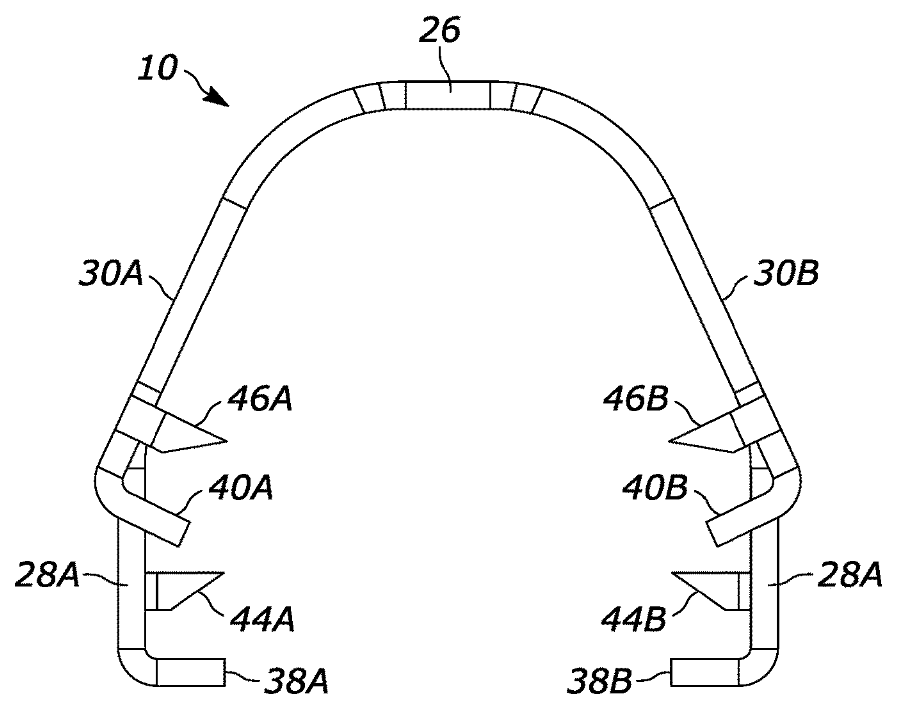
FIG. 5D is a rear view of the fusion/fixation device of FIG. 5A.
Figure 5E:
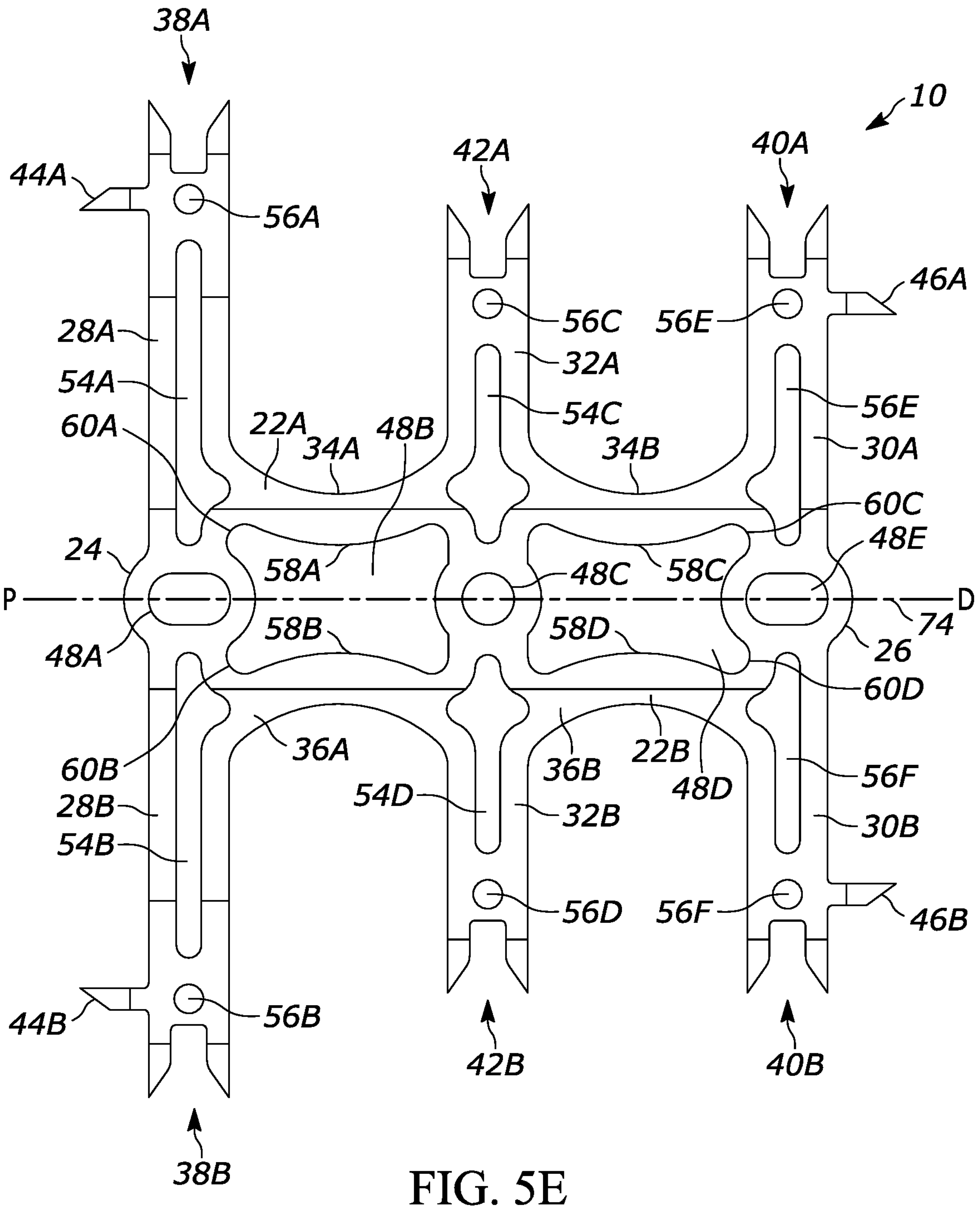
FIG. 5E is a top view of the fusion/fixation device of FIG. 5A prior to being formed into the desired shape.
Figure 6A:
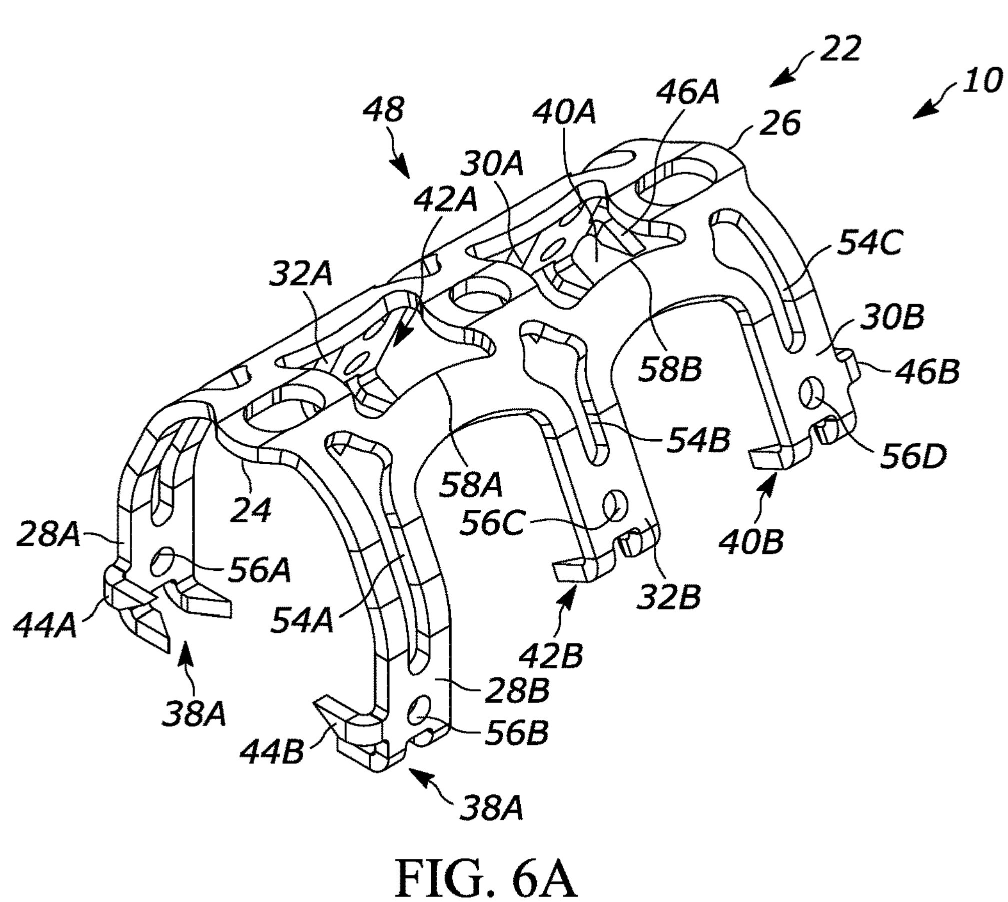
FIG. 6A is a perspective view of a fusion/fixation device according to an aspect of the disclosure.
Figure 6B:
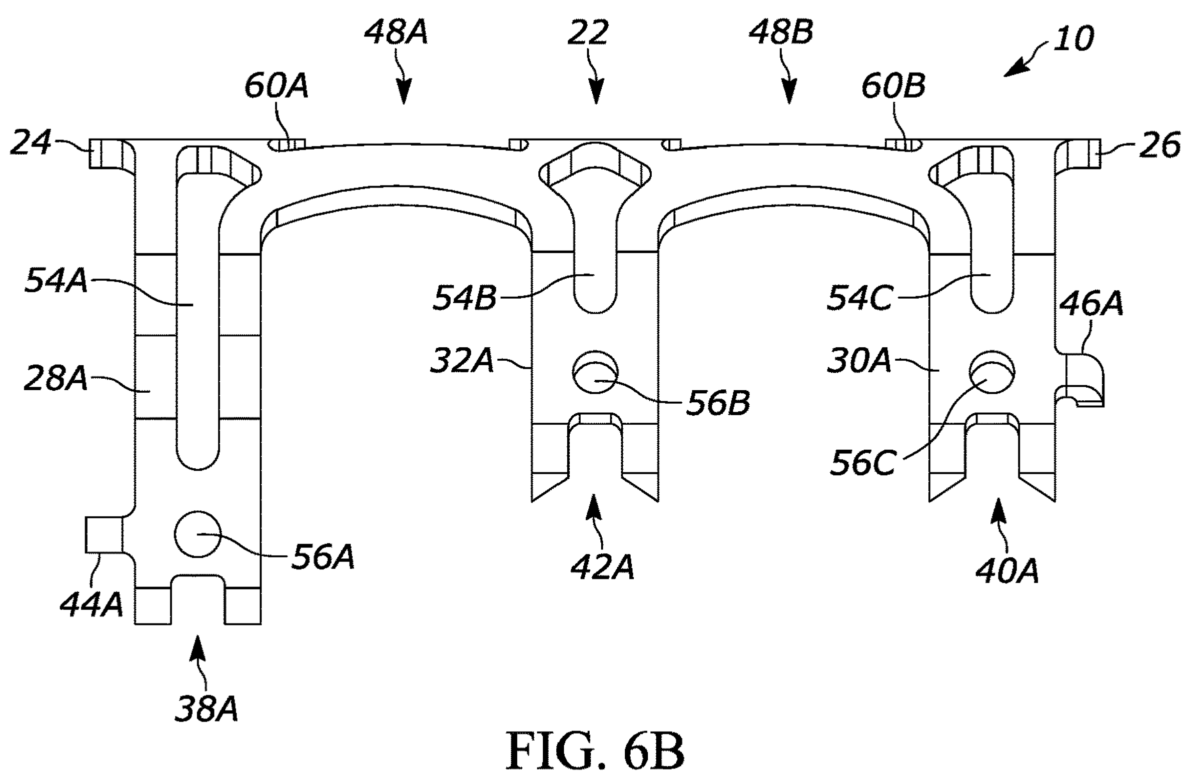
FIG. 6B is a side view of a fusion/fixation device of FIG. 6A.
Figure 6C:
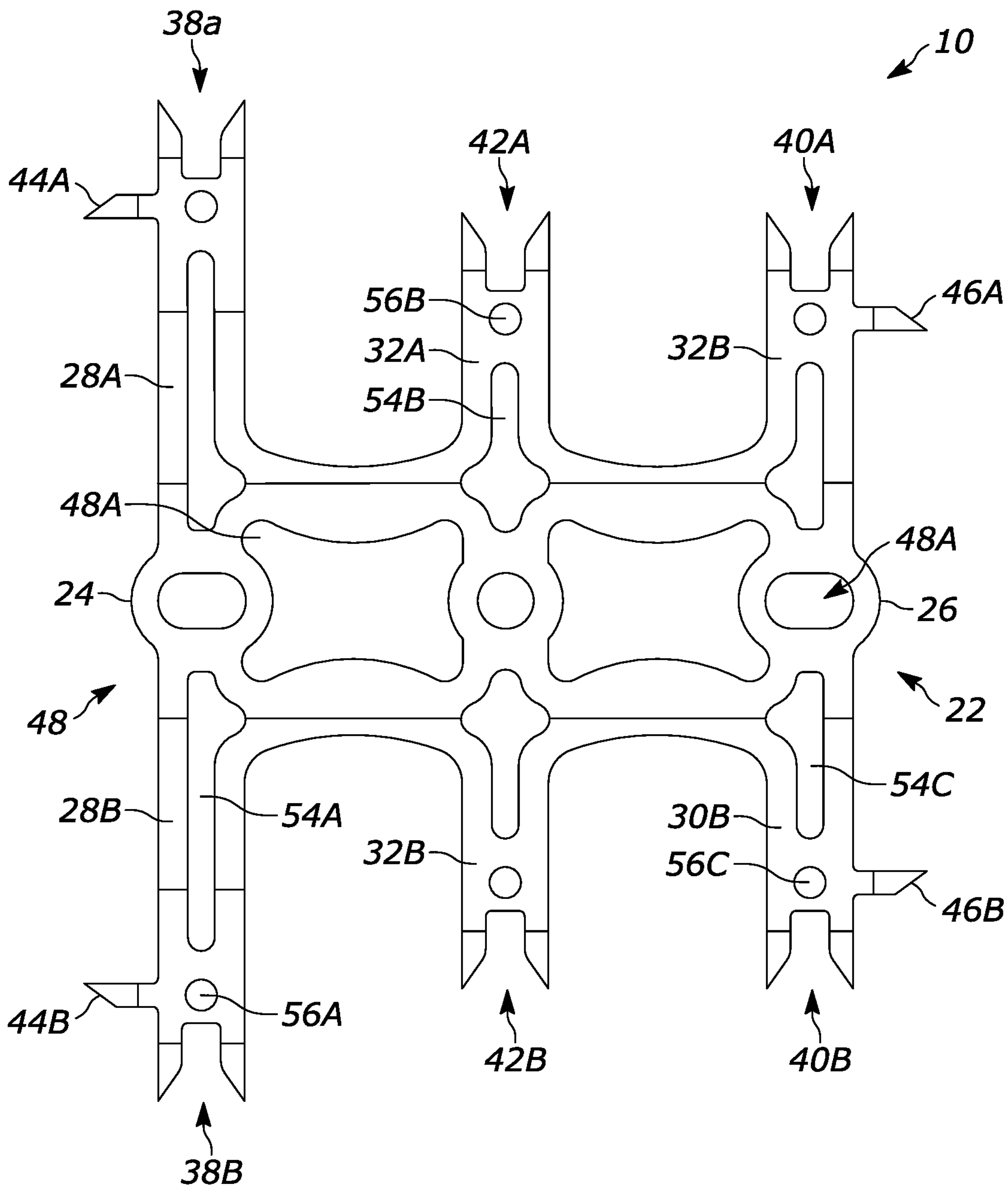
FIG. 6C is a top view of the fusion/fixation device of FIG. 6A prior to being formed into the desired shape.
Figure 7A:
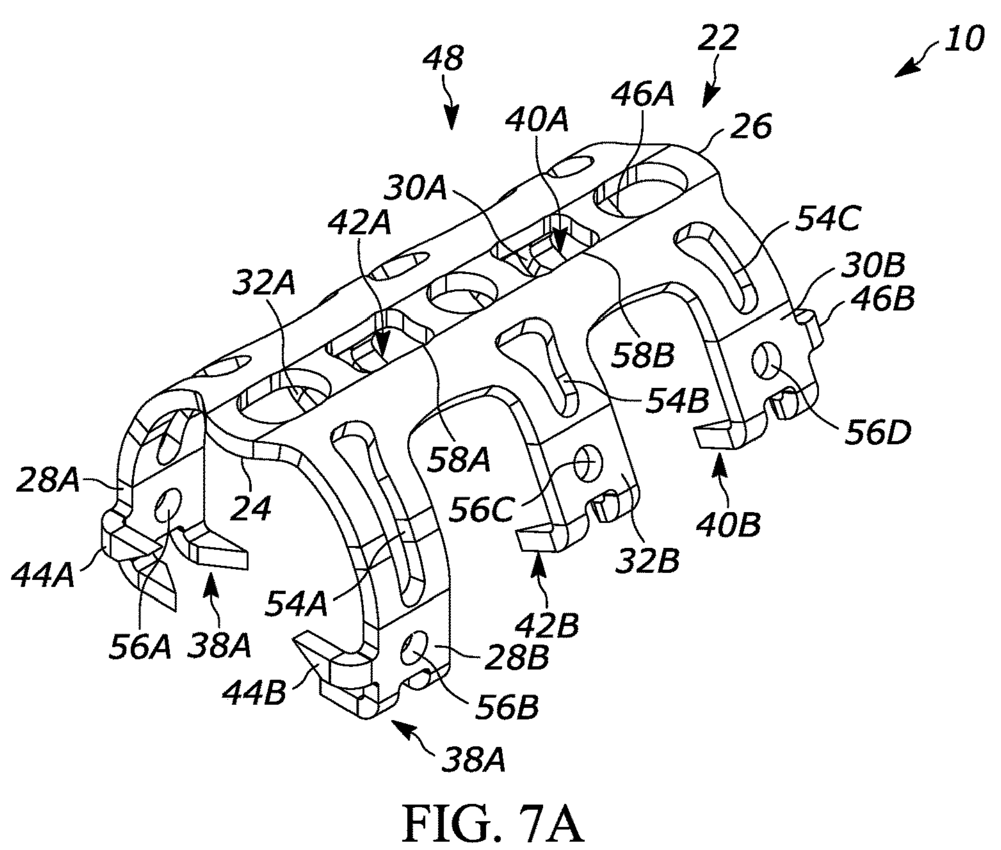
FIG. 7A is a perspective view of a fusion/fixation device according to an aspect of the disclosure.
Figure 7B:
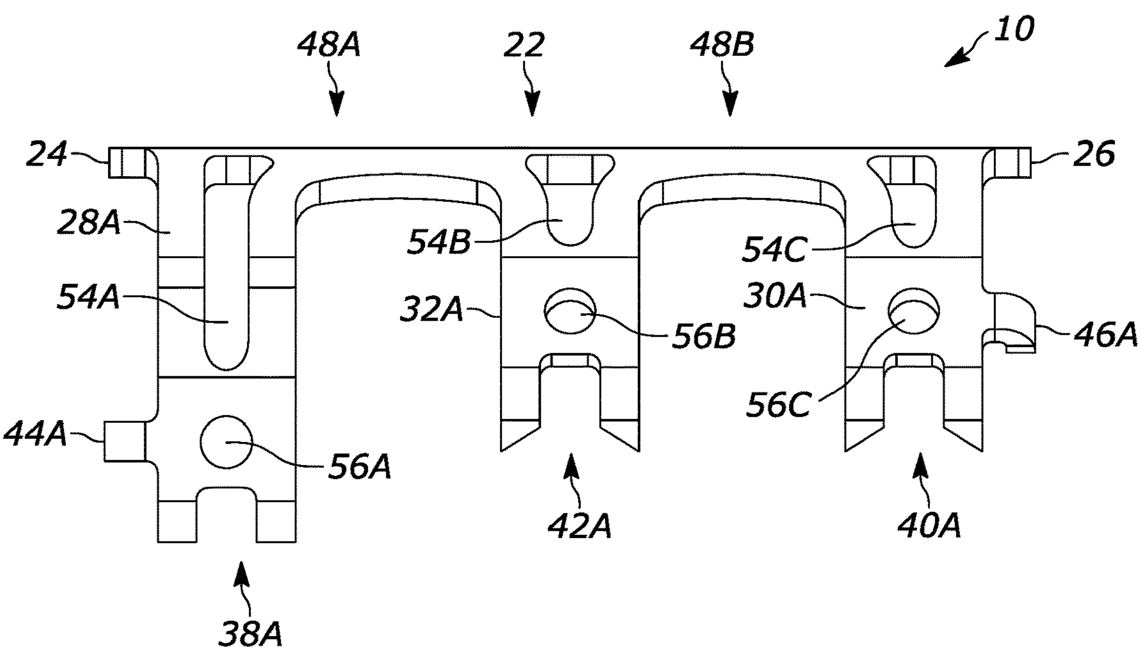
FIG. 7B is a side view of a fusion/fixation device of FIG. 7A.
Figure 7C:
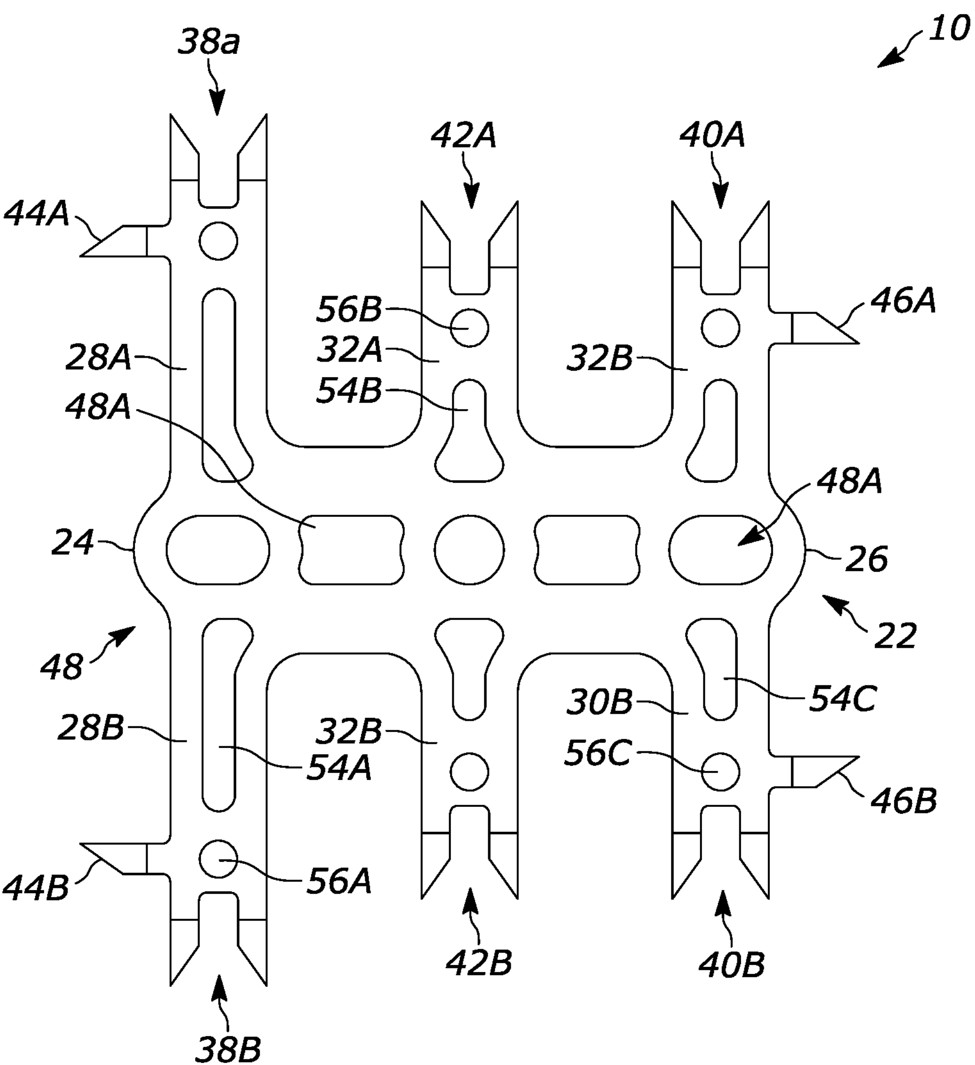
FIG. 7C is a top view of the fusion/fixation device of FIG. 7A prior to being formed into the desired shape.
Figure 8A:
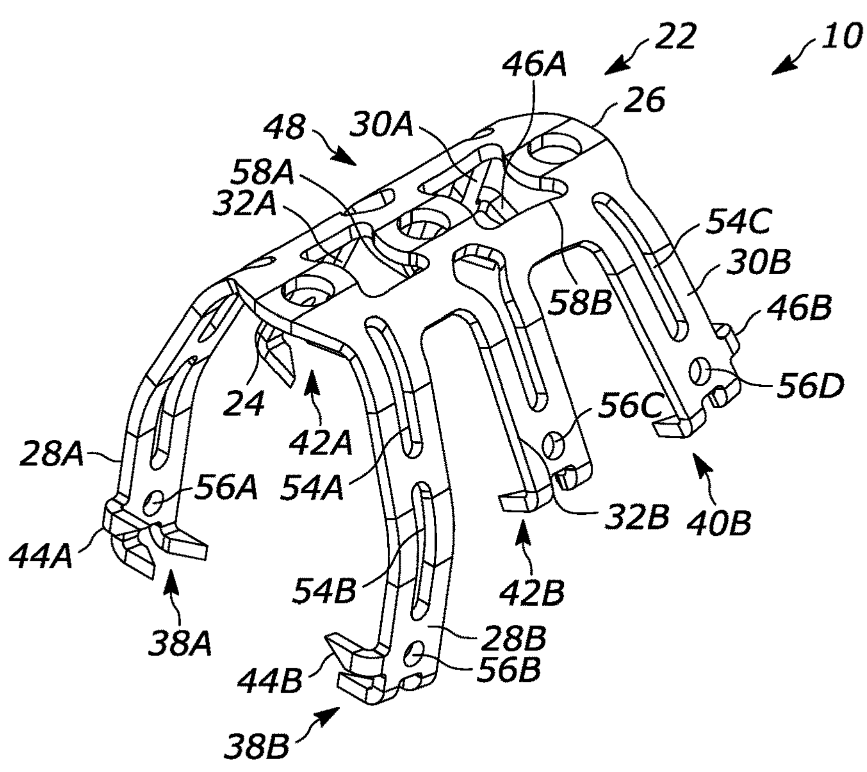
FIG. 8A is a perspective view of a fusion/fixation device according to an aspect of the disclosure.
Figure 8B:
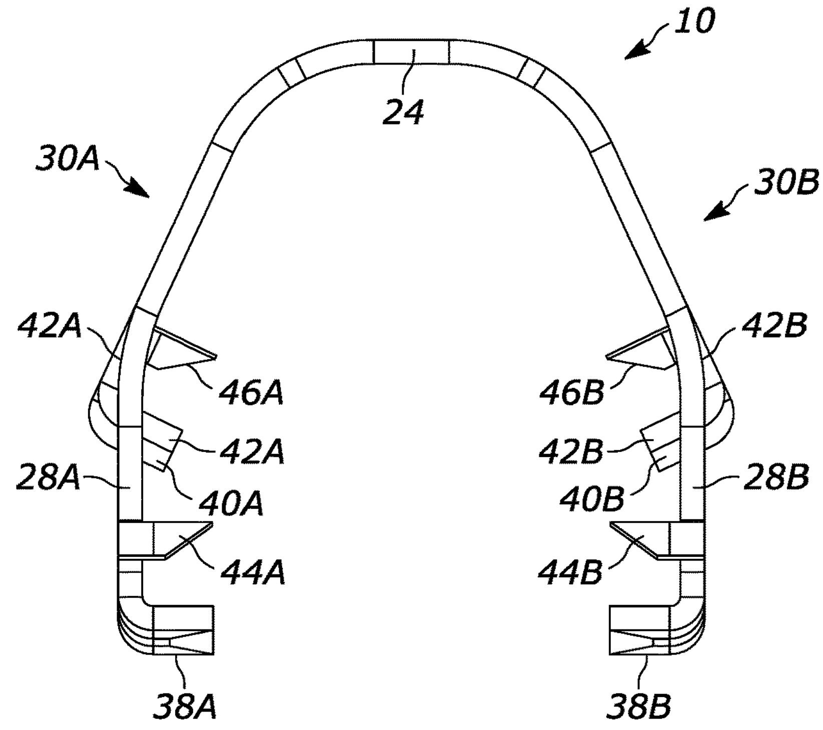
FIG. 8B is a front view of the fusion/fixation device of FIG. 8A.
Figure 8C:
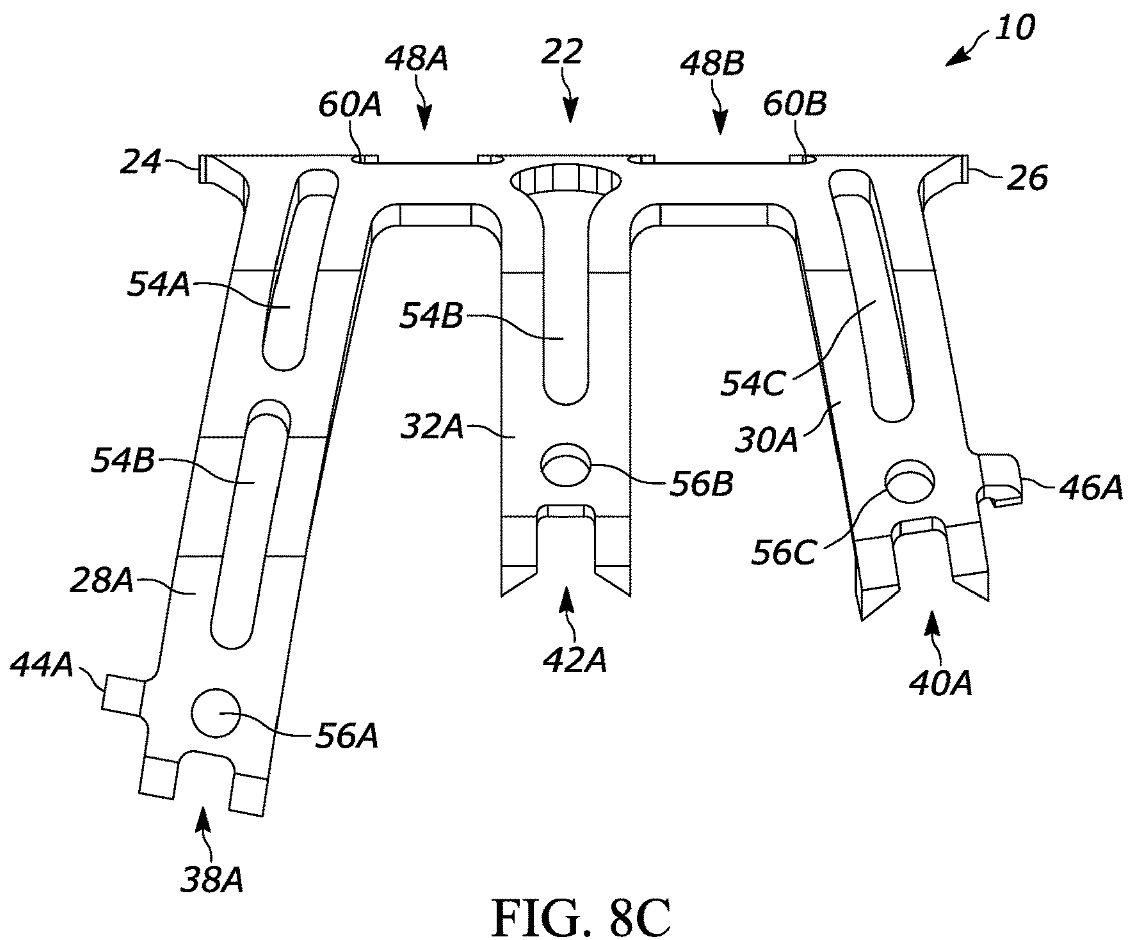
FIG. 8C is a side view of a fusion/fixation device of FIG. 8A.
Figure 8D:
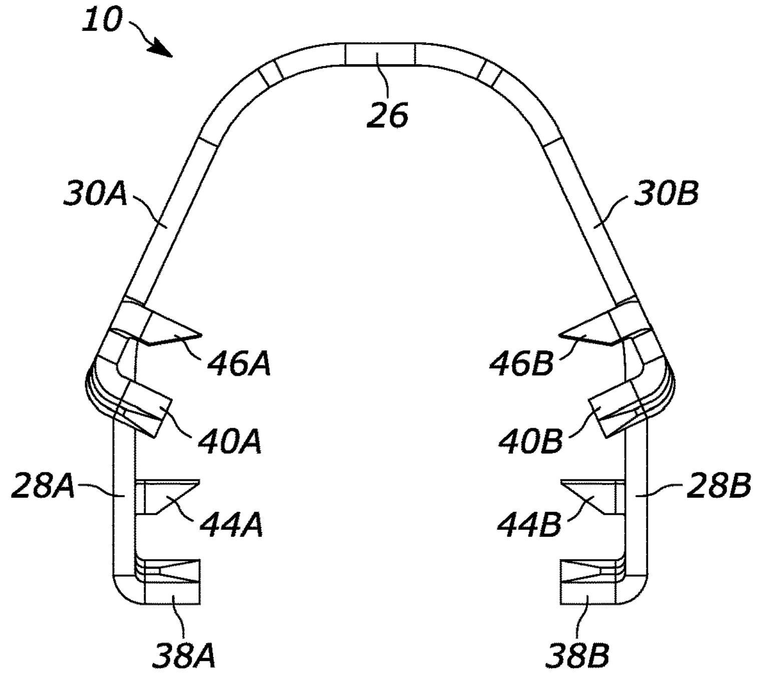
FIG. 8D is a rear view of the fusion/fixation device of FIG. 8A.
Figure 8E:
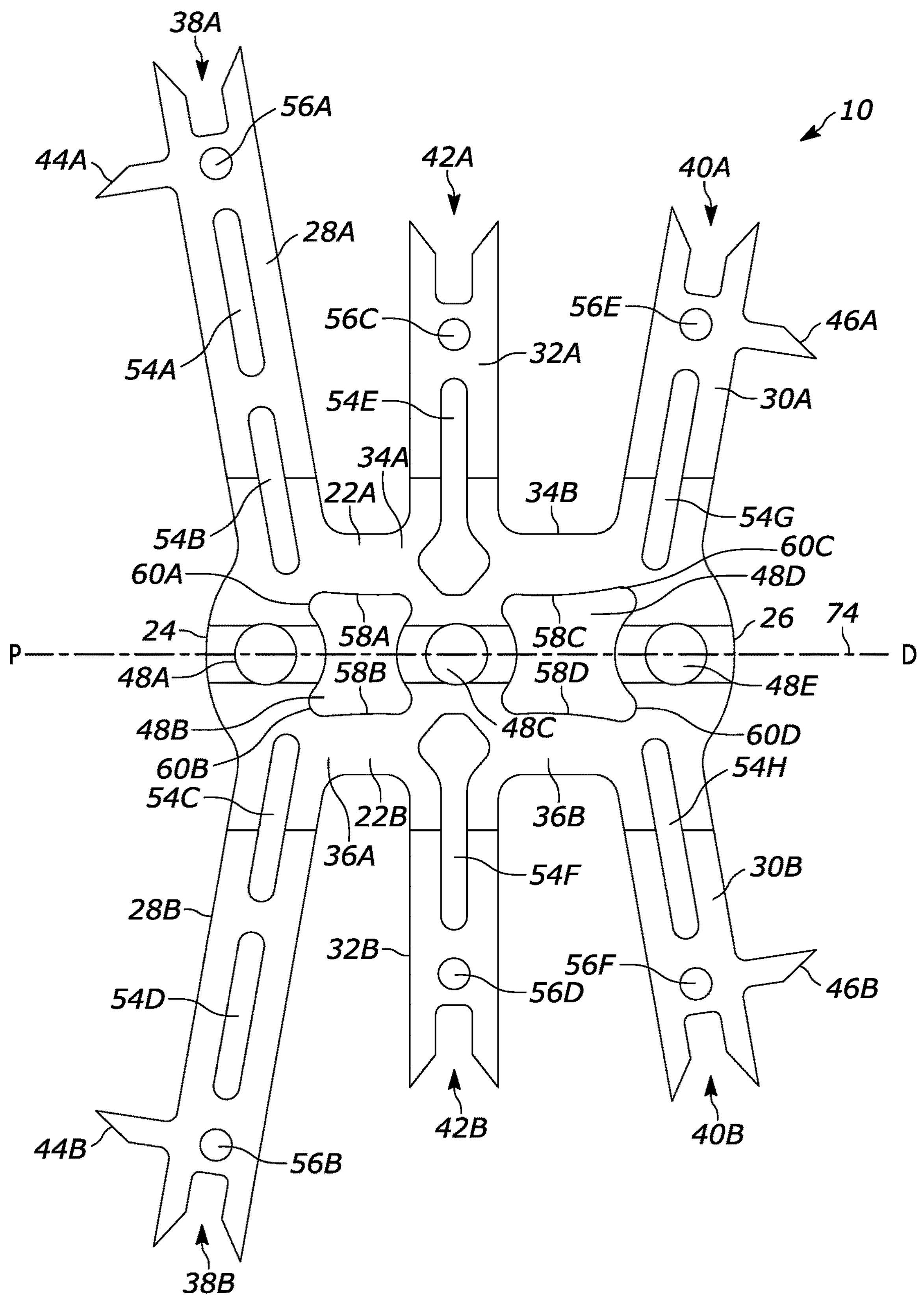
FIG. 8E is a top view of the fusion/fixation device of FIG. 8A prior to being formed into the desired shape.
Figure 9A:
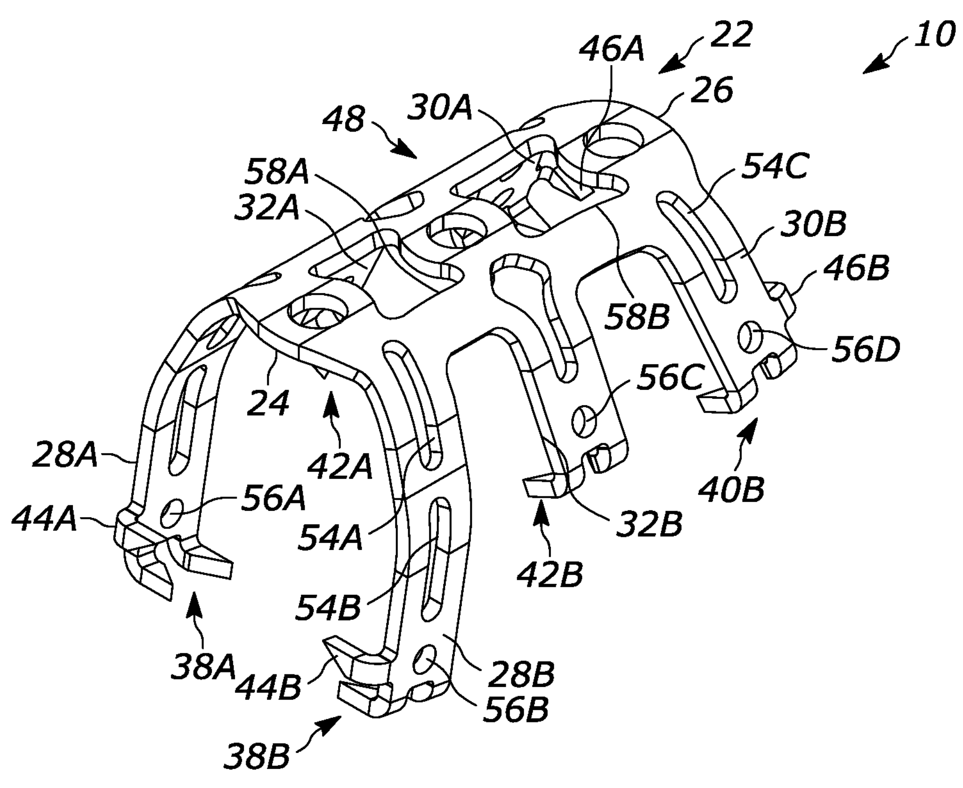
FIG. 9A is a perspective view of a fusion/fixation device according to an aspect of the disclosure.
Figure 9B:
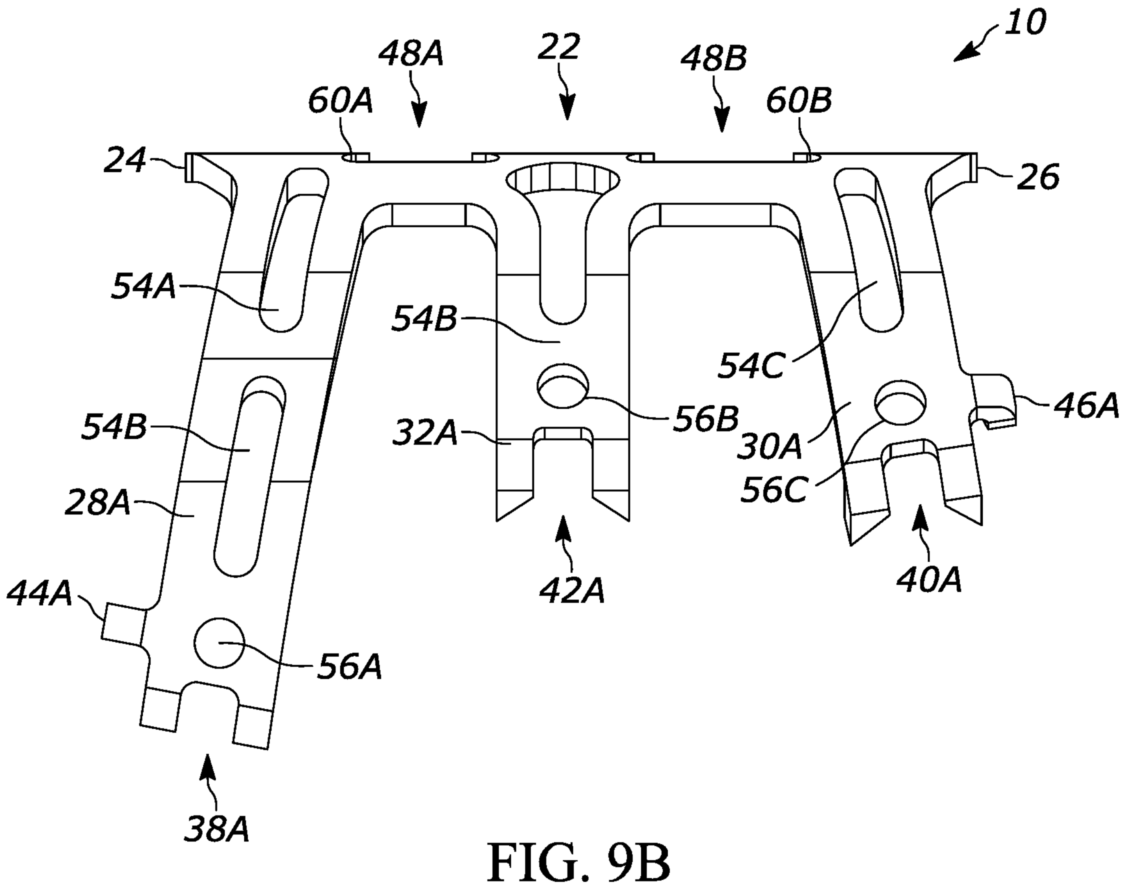
FIG. 9B is a side view of a fusion/fixation device of FIG. 9A.
Figure 9C:
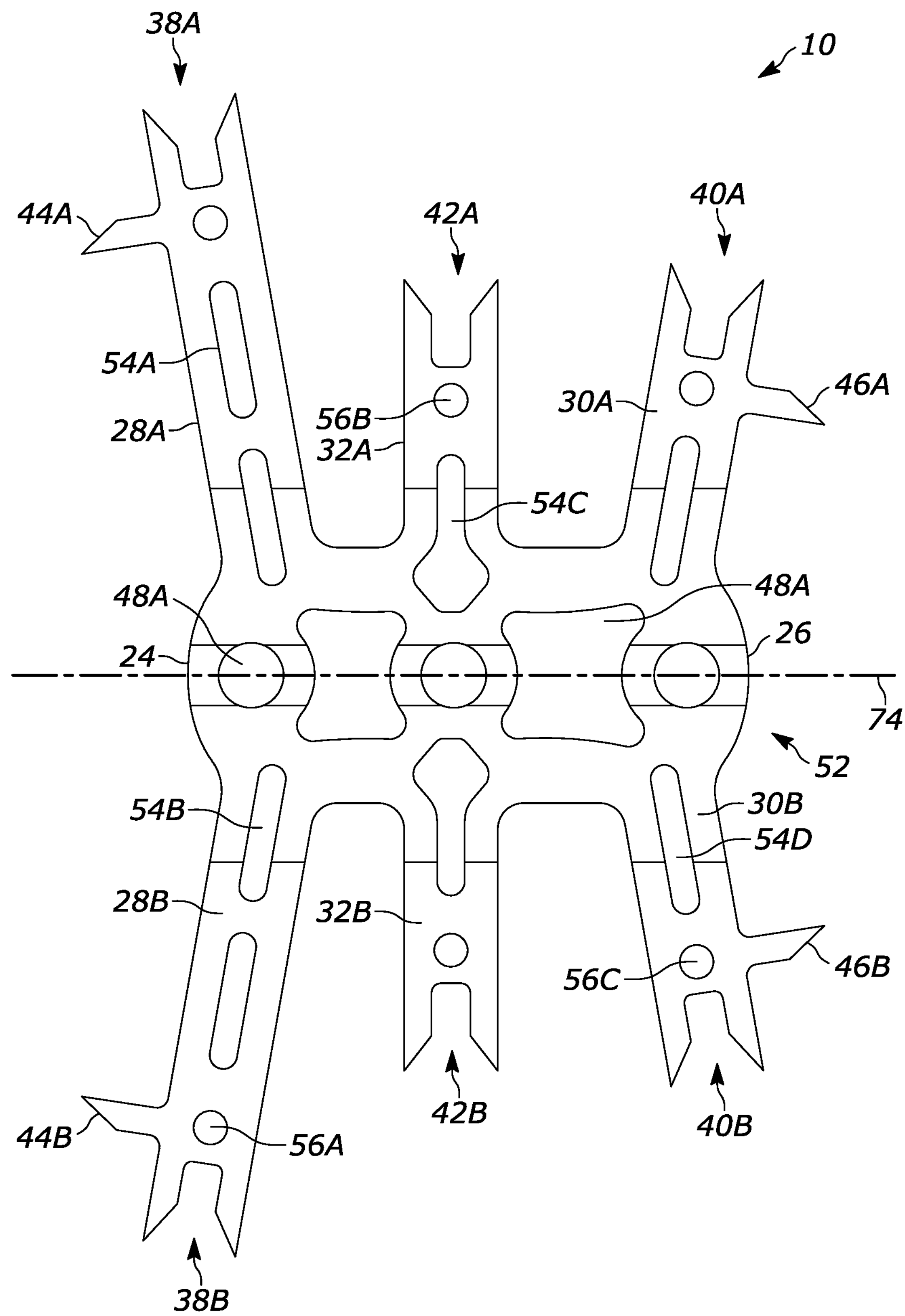
FIG. 9C is a top view of the fusion/fixation device of FIG. 9A prior to being formed into the desired shape.
Figure 10A:
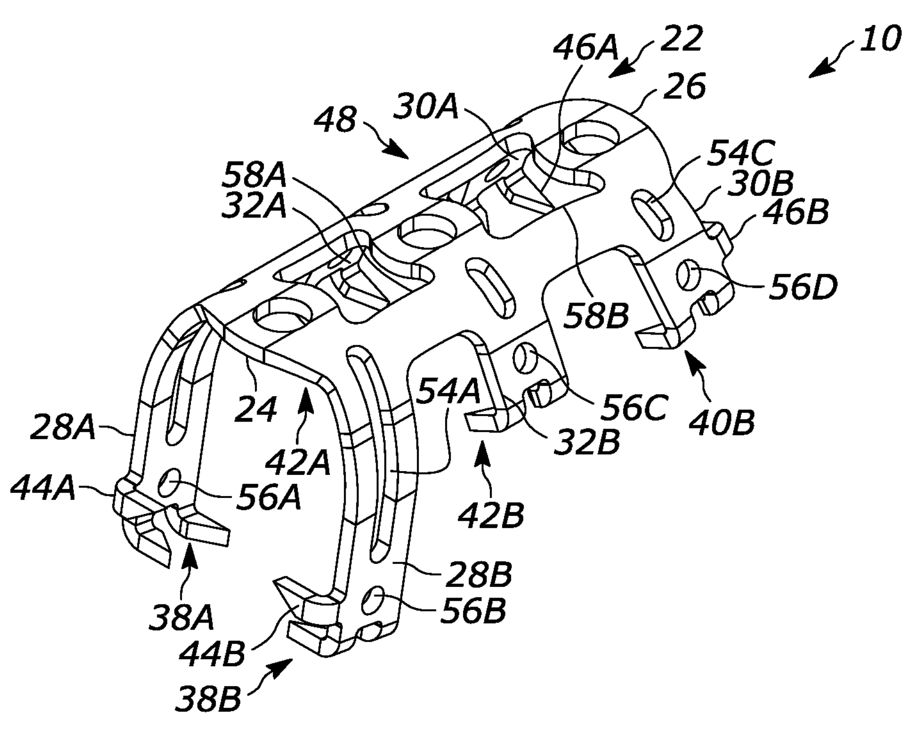
FIG. 10A is a perspective view of a fusion/fixation device according to an aspect of the disclosure.
Figure 10B:
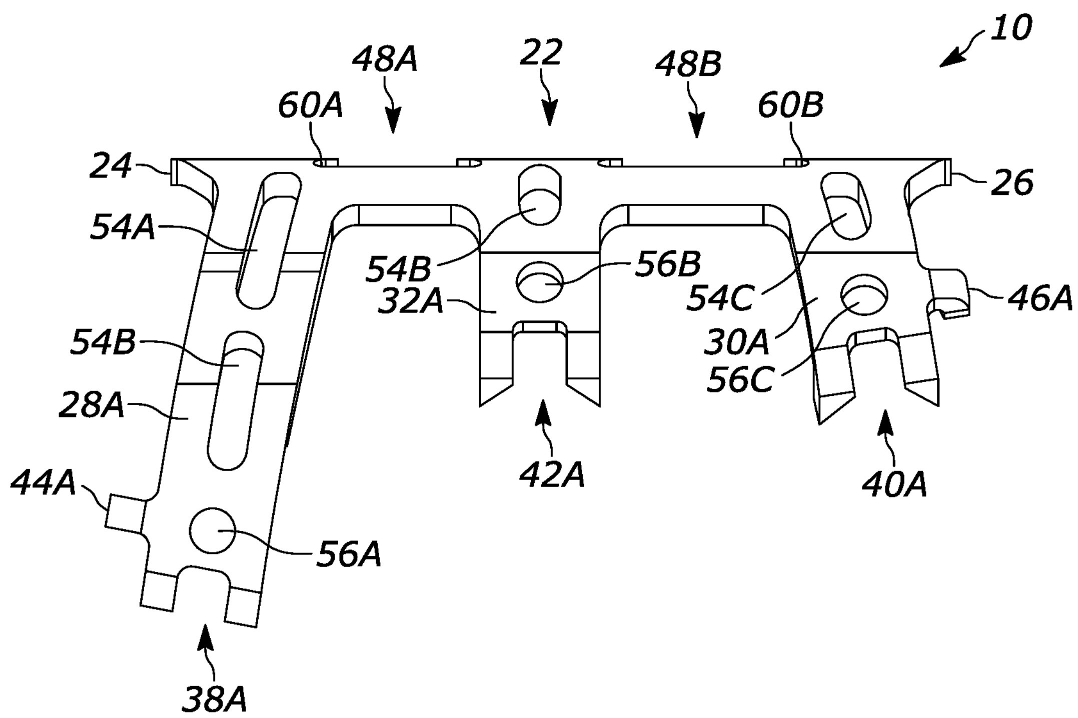
FIG. 10B is a side view of a fusion/fixation device of FIG. 10A.
Figure 10C:
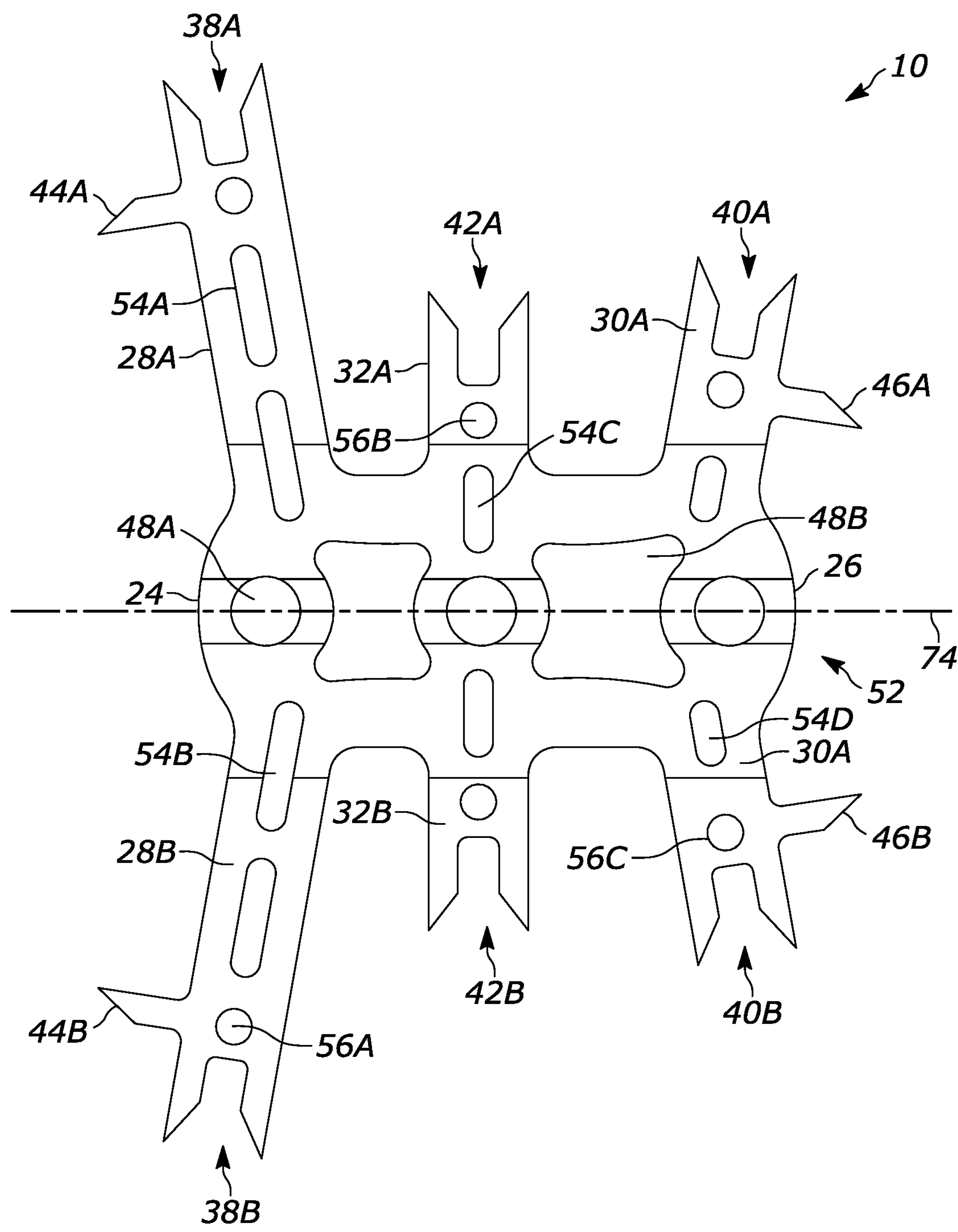
FIG. 10C is a top view of the fusion/fixation device of FIG. 10A prior to being formed into the desired shape.
Figure 11A:
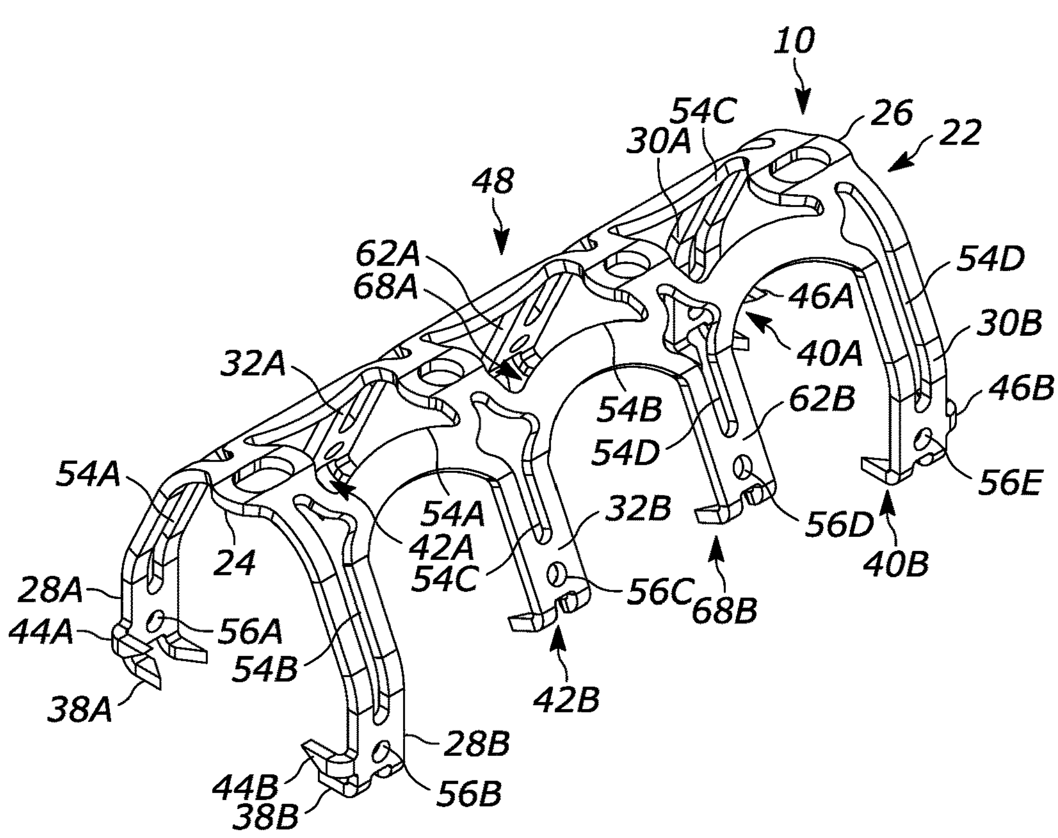
FIG. 11A is a perspective view of a fusion/fixation device according to an aspect of the disclosure.
Figure 11B:
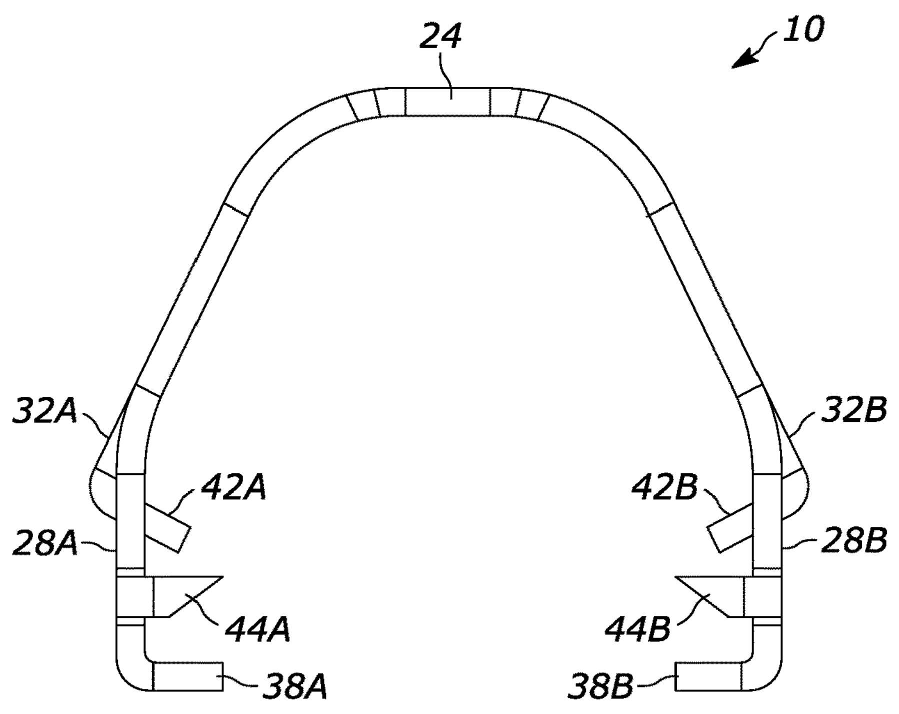
FIG. 11B is a front view of the fusion/fixation device of FIG. 11A.
Figure 11C:
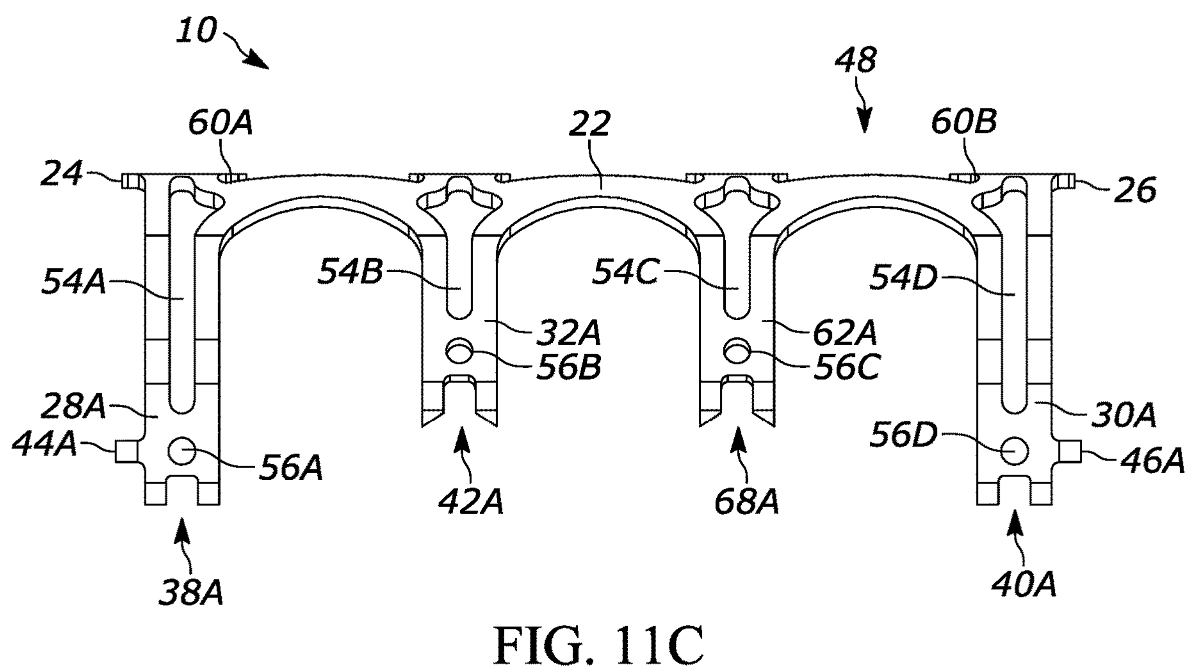
FIG. 11C is a side view of a fusion/fixation device of FIG. 11A.
Figure 11D:
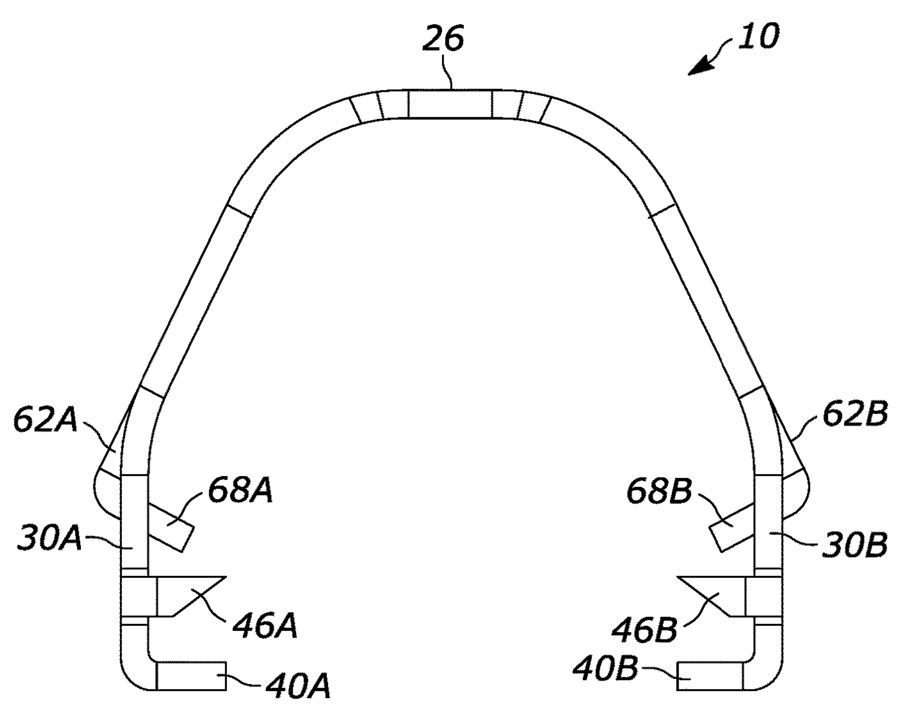
FIG. 11D is a rear view of the fusion/fixation device of FIG. 11A.
Figure 11E:
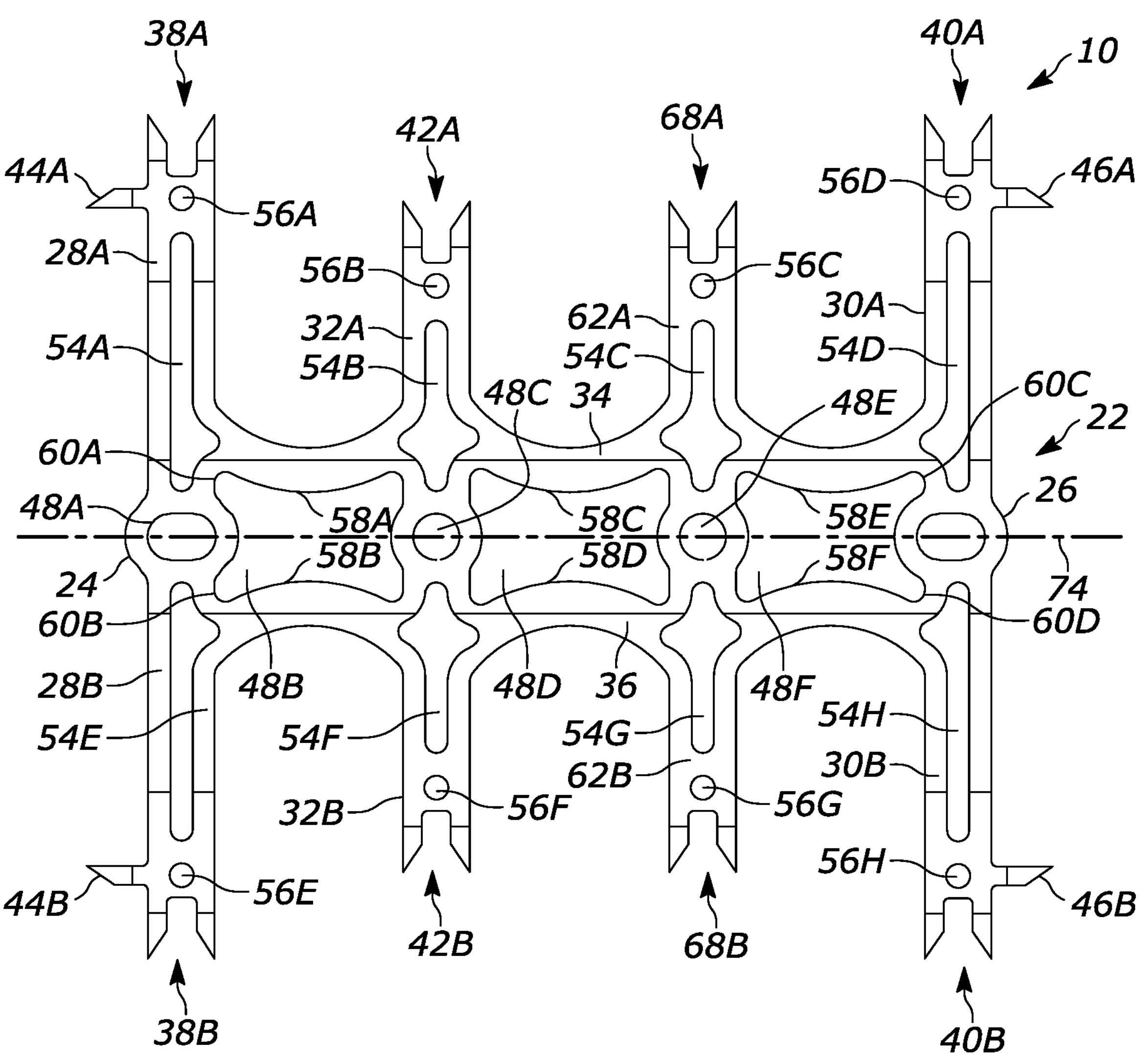
FIG. 11E is a top view of the fusion/fixation device of FIG. 11A prior to being formed into the desired shape.
Figures 12A, 12B:
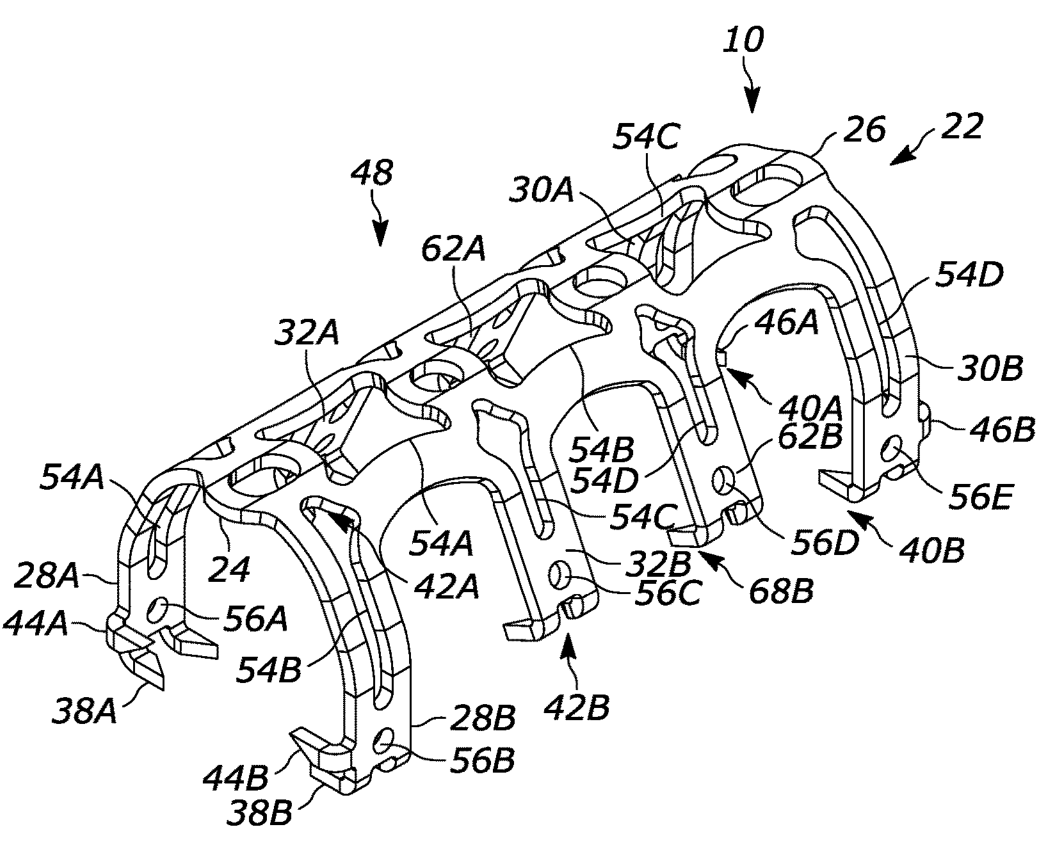
FIG. 12A is a perspective view of a fusion/fixation device according to an aspect of the disclosure.
FIG. 12B is a side view of a fusion/fixation device of FIG. 12A.
Figure 12C:
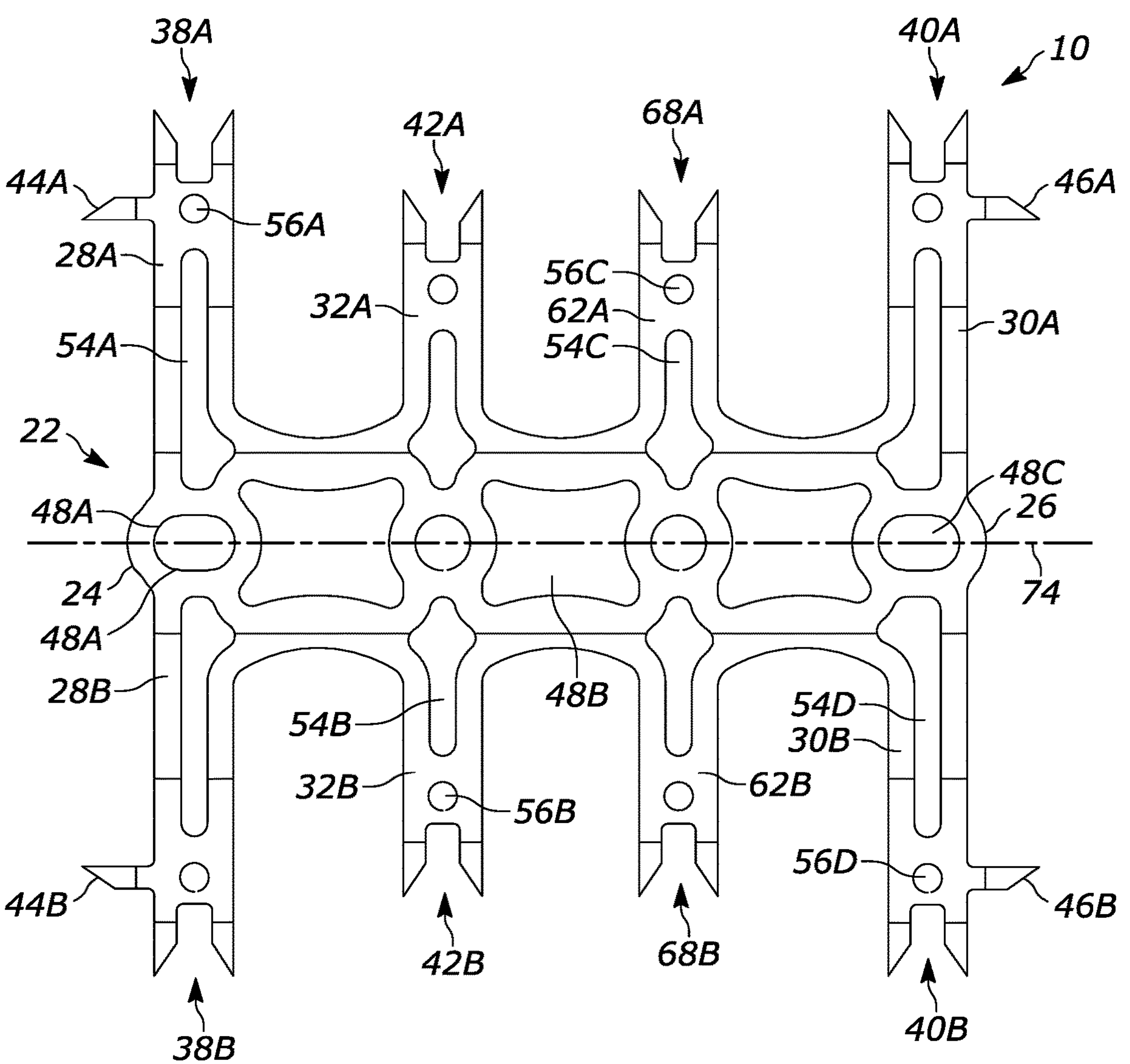
FIG. 12C is a top view of the fusion/fixation device of FIG. 12A prior to being formed into the desired shape.
Figure 13A:
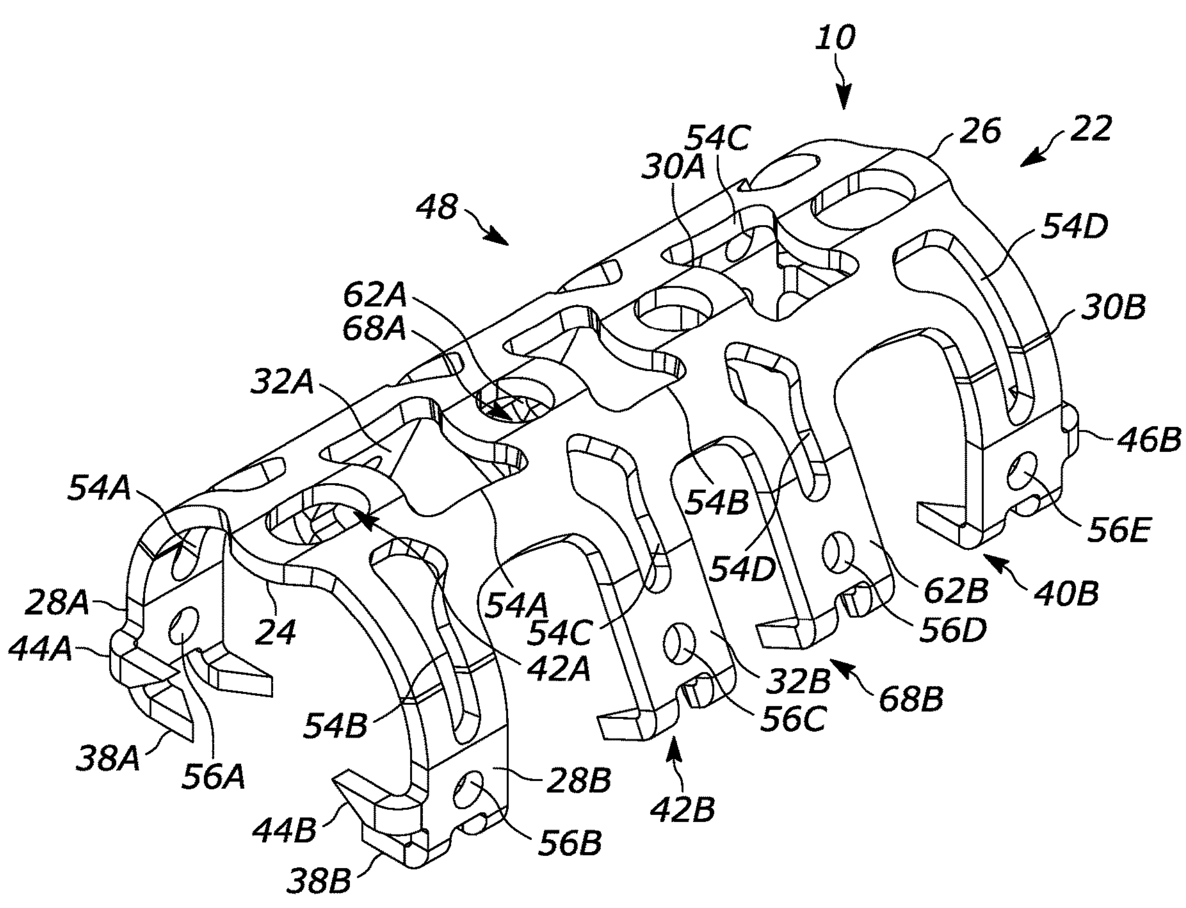
FIG. 13A is a perspective view of a fusion/fixation device according to an aspect of the disclosure.
Figure 13B:
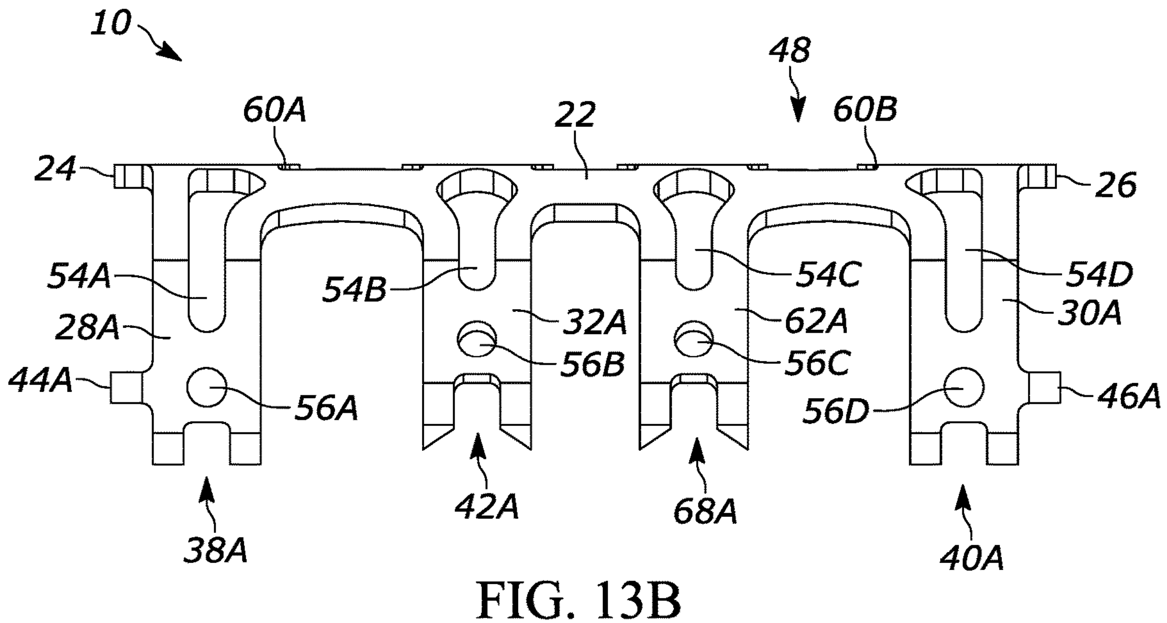
FIG. 13B is a side view of a fusion/fixation device of FIG. 13A.
Figure 13C:
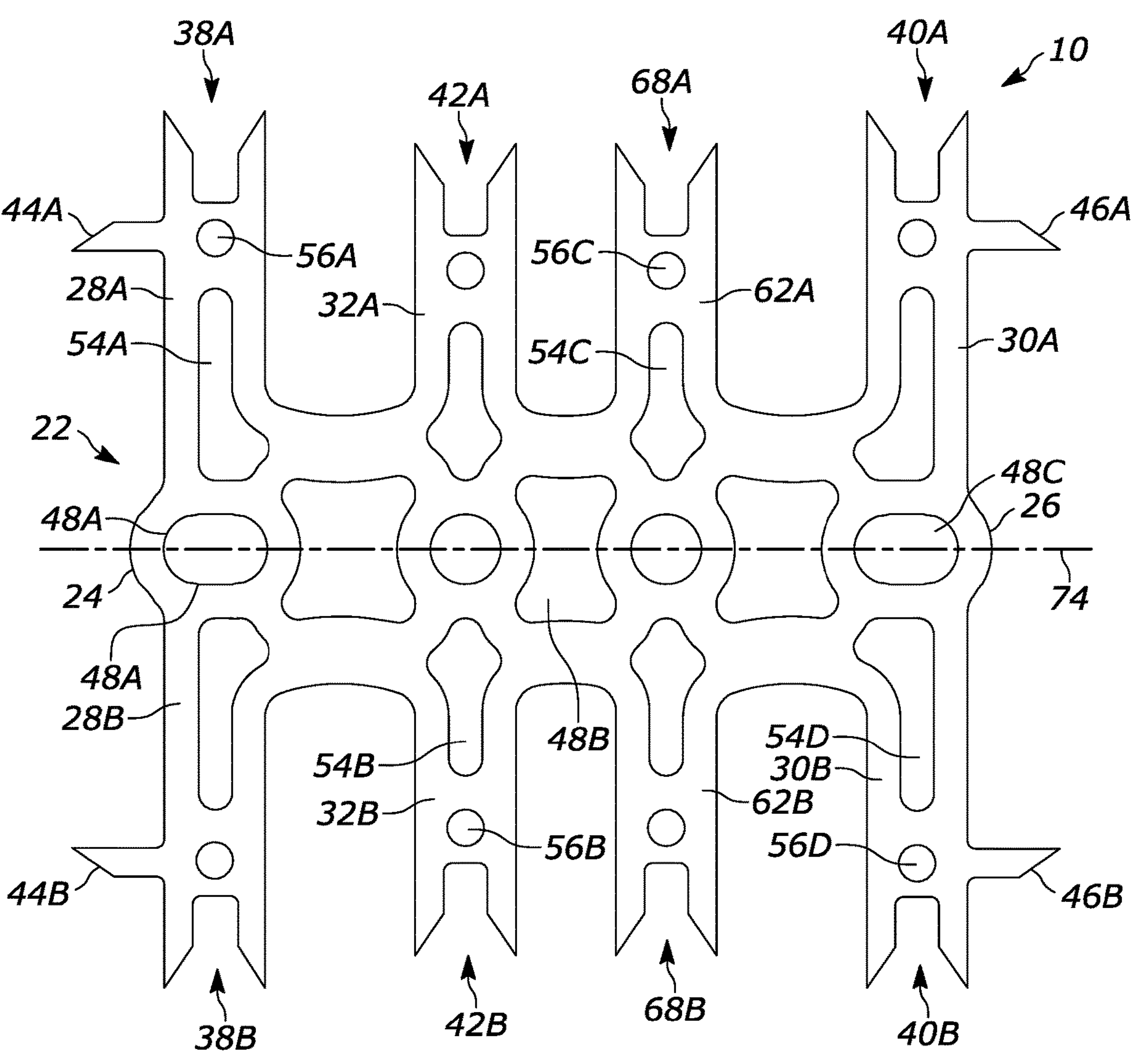
FIG. 13C is a top view of the fusion/fixation device of FIG. 13A prior to being formed into the desired shape.

FIG. 4 depicts the fusion/fixation device 10 having a second pair of medial arms or structures 62A, 62B (the other arm is not visible in FIG. 4). In this configuration, and others comprising additional arms or pairs of arms, the additional arms increase stability and robustness, which can be useful in applications that have higher loads or involve multiple, spaced primary fractures granted that sufficient space is available for application. The presence of additional arms can result in more of the plurality of openings 48*n* being present on the at least one spine 22.

The pair of medial arms 32A, 32B may each have a mid tine 64A, 64B (or medial tine) and the second pair of medial arms 62A, 62B may each have a mid tine 66A, 66B (or mid second medial tine). As shown, the second pair of medial arms 62A, 62B also comprise at least one tine 68A, 68B (or second medial tine). In the configuration depicted in FIG. 4, the mid tines 64A, 64B, 66A, 66B are positioned towards the midline of the at least spine 22 such that the mid tines 64A, 64B, 66A, 66B mirror one another about a cross section of the at least one spine 22.

In other aspects, as seen in FIG. 4, the at least one spine 22 comprises a proximal plate 70 and a distal plate 72 that are positioned and coupled to the at least one spine 22 at the proximal end 24 and the distal end 26.

In further aspects, shown in FIGS. 5A-5E, the fusion/fixation device 10 comprises the first spine 22A and the second spine 22B. One of the pair of proximal arms 28A extends outwardly from the spine 22A at the proximal end 24 and the other of the pair of proximal arms 28B extends outwardly from the second spine 22B at the proximal end 24. In some aspects, the pair of proximal arms 28A, 28B extend perpendicularly or substantially perpendicularly outward from a centerline 74 of the at least one spine 22 formed by a perpendicular plane extending from the proximal end 24 and the distal end 26 such that the centerline 74 bisects the fusion/fixation device 10 into mirrored halves as shown by the centerline 74 present in at least FIG. 5E.

In still other aspects, one of the one of the pair of distal arms 30A extends outwardly from the first spine 22A at the distal end 26 and the other of the pair of distal arms 30A extends outwardly from the second spine 22B at the distal end 26. In some aspects, the pair of proximal arms 28A, 28B extend perpendicularly or substantially perpendicularly outward in from a centerline 74 of the at least one spine 22.

One of the pair of medial arms 32A extends perpendicularly or substantially perpendicularly outward from the first spine 22A with respect to the centerline 74 and the other of the pair of medial arms 32B extends perpendicularly outward from the second spine 22B with respect to the centerline. In some aspects, the pair of medial arms 32A, 32B are equidistantly positioned from the pair of proximal arms 28A, 28B and the pair of distal arms 30A, 30B, but non-equidistant positioning is contemplated.

As seen further in FIGS. 5A-5E, in some aspects the pair of proximal arms 28A, 28B have a greater length than the pair of distal arms 30A, 30B and the pair of medial arms 32A, 32B. In the depicted configuration, the pair of distal arms 30A, 30B have a length equal to the pair of medial arms 32A, 32B. Rather than a single tine positioned at the terminal end of the pair of proximal arms 28A, 28B, the pair of distal arms 30A, 30B, and the pair of medial arms 32A, 32B as depicted in FIG. 3, the at least one tine 38A, 38B, 40A, 40B, 42A, 42B comprises two tines, respectively. In such configurations, the fusion/fixation device 10 has increased fixation and resistance to deforming after implantation.

FIGS. 6A-6C and FIGS. 7A-7C depict configurations of the fusion/fixation device 10 shown in FIGS. 5A-5E. The shown configurations show the of proximal arms 28A, 28B, the pair of distal arms 30A, 30B, and the pair of medial arms 32A, 32B that are of differing dimensions. Accordingly, the versatility of the fusion/fixation device 10 is understood as a fusion/fixation device 10 is configurable to accommodate differing types and sizes of fracture and osteotomy.

In other aspects, shown in FIGS. 8A-8E, the fusion/fixation device 10 comprises the first spine 22A and the second spine 22B. One of the pair of proximal arms 28A extends outwardly from the first spine 22A at the proximal end 24 and the other of the pair of proximal arms 28B extends outwardly from the second spine 22B at the proximal end 24. In some aspects, the pair of proximal arms 28A, 28B extend outwardly in the proximal direction in an acute angle formed between the centerline 74 of the first spine 22A and the second spine 22B. In particular aspects, the angle formed by the centerline 74 and the pair of proximal arms 28A, 28B is 80 degrees respectively. The extension of the pair of proximal arms 28A, 28B positions a terminal end of the pair of proximal arms 28A, 28B proximally beyond the proximal end 24.

In still further aspects, one of the pair of distal arms 30A extends outwardly from the first spine 22A at the distal end 26 and the other of the pair of distal arms 30A extends outwardly from the second spine 22B at the distal end 26. In other aspects, the pair of distal arms 30A, 30B extend outwardly in the distal direction in an acute angle formed between the centerline 74 and the pair of distal arms 30A, 30B. The angle formed with the centerline 74 and the pair of distal arms 30A, 30B is 80 degrees in some aspects. The extension of the pair of distal arms 30A, 30B positions a terminal end of the pair of distal arms 30A, 30B distally beyond the distal end 26.

One of the pair of medial arms 32A extends perpendicularly or substantially perpendicularly outward from the first spine 22A with respect to the centerline 74 and the other of the pair of medial arms 32B extends perpendicularly outward from the second spine 22B with respect to the centerline. In some aspects, the pair of medial arms 32A, 32B are equidistantly positioned from the pair of proximal arms 28A, 28B and the pair of distal arms 30A, 30B, but non-equidistant positioning is contemplated.

As seen in FIGS. 8A-8E, in some aspects the pair of proximal arms 28A, 28B have a greater length than the pair of distal arms 30A, 30B and the pair of medial arms 32A, 32B. In the depicted configuration, the pair of distal arms 30A, 30B have a greater length than the pair of medial arms 32A, 32B. Rather than a single tine positioned at the terminal end of the pair of proximal arms 28A, 28B, the pair of distal arms 30A, 30B, and the pair of medial arms 32A, 32B as depicted in FIG. 3, the at least one tine 38A, 38B, 40A, 40B, 42A, 42B comprises two tines, respectively. In such configurations, the fusion/fixation device 10 has increased fixation and resistance to deforming after implantation.

FIGS. 9A-9C and FIGS. 10A-10C depict configurations of the fusion/fixation device 10 shown in FIGS. 8A-8E. The shown configurations show the pair of proximal arms 28A, 28B, the pair of distal arms 30A, 30B, and the pair of medial arms 32A, 32B that are of different dimensions. Accordingly, the versatility of the fusion/fixation device 10 is understood as a fusion/fixation device 10 is configurable to accommodate differing types and sizes of fracture and osteotomy.

In further aspects, shown in FIGS. 11A-11E, the fusion/fixation device 10 comprises the first spine 22A and the second spine 22B. One of the pair of proximal arms 28A extends outwardly from the spine 22A at the proximal end 24 and the other of the pair of proximal arms 28B extends outwardly from the second spine 22B at the proximal end 24. In some aspects, the pair of proximal arms 28A, 28B extend perpendicularly or substantially perpendicularly outward in from the centerline 74 of the at least one spine 22 as depicted in, at least, FIG. 11E.

In still other aspects, one of the one of the pair of distal arms 30A extends outwardly from the first spine 22A at the distal end 26 and the other of the pair of distal arms 30A extends outwardly from the second spine 22B at the distal end 26. In some aspects, the pair of proximal arms 28A, 28B extend perpendicularly or substantially perpendicularly outward in from a centerline 74 of the at least one spine 22.

One of the pair of medial arms 32A extends perpendicularly outward from the first spine 22A with respect to the centerline 74 and the other of the pair of medial arms 32B extends perpendicularly outward from the second spine 22B with respect to the centerline 74. In further aspects, one of the second pair of medial arms 62A extends perpendicularly outward from the first spine 22A with respect to the centerline 74 and the other of the second pair of medial arms 62B extends perpendicularly outward from the second spine 22B with respect to the centerline 74.

In some aspects, the pair of medial arms 32A, 32B and the second pair of medial arms 62A, 62B are equally distantly spaced along the at least one spine 22 between the proximal end 24 and the distal end 26. In such aspects, the distance between the pair of proximal arms 28A, 28B and the pair of medial arms 32A, 32B, the distance between the pair of medial arms 32A, 32B and the second pair of medial arms 62A, 62B, and distance between the second pair of medial arms 62A, 62B and the distal pair of arms 30A, 30B are equally or substantially equal. An illustrative example of this configuration is readily viewed in at least FIG. 11E. Non-equidistant positioning is also contemplated.

As also seen in FIGS. 11A-11E, in some aspects the pair of proximal arms 28A, 28B and the pair of distal arms 30A, 30B are longer than the length of the pair of medial arms 32A, 32B and the second pair of medial arms 62A, 62B. In further aspects, the pair of proximal arms 28A, 28B and the pair of distal arms 30A, 30B have substantially the same or the same length and the pair of medial arms 32A, 32B and the second pair of medial arms 62A, 62B have substantially the same or the same length.

In the depicted configuration, rather than a single tine positioned at the terminal end of the pair of proximal arms 28A, 28B, the pair of distal arms 30A, 30B, the pair of medial arms 32A, 32B, and the second pair of medial arms 62A, 62B as depicted in FIG. 4, the at least one tine 38A,

38B, 40A, 40B, 42A, 42B, 68A, 68B comprises two tines, respectively. In such configurations, the fusion/fixation device 10 has increased fixation and resistance to deforming after implantation.

FIGS. 12A-12C and FIGS. 13A-13C depict configurations of the fusion/fixation device 10 shown in FIGS. 11A-11E. The shown configurations show the of proximal arms 28A, 28B, the pair of distal arms 30A, 30B, the pair of medial arms 32A, 32B, and the second pair of medial arms 62A, 62B that are of differing dimensions. Accordingly, the versatility of the fusion/fixation device 10 is understood as a fusion/fixation device 10 is configurable to accommodate differing types and sizes of fracture and osteotomy.

Among the various aspects disclosed herein, the fusion/fixation device 10 may be made of an appropriate semi-rigid, deformable material. In certain aspects, the fusion/fixation device is made from any of a variety of metal alloys, including, for example, medical grade stainless steel, titanium, or other similar materials.

In the various aspects discussed and contemplated herein, including the illustrative exemplars of the Figures, the device may have a thickness ranging from at least 0.1 mm to 2 mm, but in other aspects has a thickness of 0.635 mm, which provides the unique advantage of providing sufficient rigidity to promote primary healing, while maintaining a deformable construct that also minimizes the "footprint" after implant. The length and width of the fusion/fixation device 10, including the arm or arms and the spine may be of any suitable size due to the variety and nature of the fracture 20.

As depicted in FIGS. 5E, 6C, 7C, 8E, 9C, 10C, 11E, 12C, and 13C, the fusion/fixation device 10 can be cut from a sheet of metal (or other material) into a flat piece and subsequently formed into the desired shape for the fusion/fixation device 10 as shown in Figures. In one embodiment, the specific configuration and footprint of the fusion/fixation device 10, including the length, width, geometry and thickness, is based upon the intended fracture or osteotomy target site and anatomic restraints. That is, the specific size and dimensions of the fusion/fixation device 10 can be determined by the size and dimensions of the target site.

In one specific embodiment, the fusion/fixation device 10 can be formed from sheet metal. More specifically, it can be cut or stamped into the desired configuration using any one of a variety of methods, including, for example, laser cutting, edm, die cutting, or any other known method. Alternatively, it is understood that the flat piece could also be formed in any known way.

Any bends or desired deformations associated with the tines, arms, and/or spine can be introduced during the stamping process or post cutting using a variety of known forming methods such as, for example, stamping, fourslide bending, bending presses, etc. Alternatively, some or all of the bends or deformations can be introduced in the application process (during the fixation/implantation procedure) instead of in the manufacturing process. It is understood that any of the aspects disclosed or contemplated herein can be bent or otherwise deformed along the spine (or spines) into a curved configuration. This spine deformation can occur at any time (from the manufacturing process forward).

In a further alternative, the arms and/or tine can be manufactured separately from the sheet metal or pins and attached by any known attachment method, such as welding.

Once the flat piece is formed, the tines are formed by bending the tines into their desired configuration as shown. According to one implementation, due to the amount of force required, the tines are bent as desired during the manufacturing process (rather than being bent in the operating area immediately prior to or during a procedure). The arms can then be bent into their desired configuration. This can be accomplished during the manufacturing process or anytime thereafter, including during the procedure as described in further detail below. Further, the at least one spine 22 can also be bent into a curved configuration at any time (from the manufacturing process forward).

In use in accordance with one or more of the various aspects discussed herein, the fusion/fixation device 10 can be placed onto, implanted, or fixed on the desired target site in order to urge two or more parts of the bone 12 together at an osteotomy or fracture to provide stability and promotion of secondary bone healing in accordance with one or more of the following steps.

Initially, the fracture 20 (or osteotomy) of the bone 12 is exposed with minimal interruption to the surrounding periosteum. As discussed, osteotomies or fractures may involve the phalanges, metatarsals, or metacarpals. In the case of the fracture 20, the fracture 20 is reduced via distraction of the bone 12 to achieve anatomic length and provisional reduction, which can be accomplished by way of small reduction forceps used to align fragments of the fracture 20.

The fusion/fixation device 10 is then placed with the distal end 26 positioned distally along the bone 12 and the proximal end 24 positioned proximally along the bone 12. In certain aspects of use, the fusion/fixation device 10 is positioned such that the fracture 20 is substantially centered in relation to the fusion/fixation device 10. In some aspects, the selection of the fusion/fixation device 10 must be determined based on fusion or fixation being sought, which can involve selection based on length of the spine, length of the arms, number of arms, length of tines, number of tines, angle of arms, position of tines, number and/or position of openings on a spine. The size and shape of the fusion/fixation device 10 may be based on spanning the distance of any or all of the fragments of the fracture 20 to capture the same as well as a solid portion of the bone 12 on each side of the fracture 20.

In some operation aspects, the fusion/fixation device 10 may be held in place during insertion using finger pressure or other topical pressures. Alternatively or in addition, the fusion/fixation device 10 may be provisionally secured in place with a pin (smooth wire), olive pin (smooth wire with a metal ball enlargement), or a clamp. Alternatively or in addition, the fusion/fixation device 10 may be provisionally secured with screws placed in the at least one opening 48 about the at least one spine 22. Use of screws can provide the advantage of added construct stability.

In further operative aspects, provisional fixation of the fusion/fixation device 10 is accomplished using the fusion/fixation device 10 itself to function as a reduction clamp. In some such aspects, an olive wire or screws may then be used to stabilize the fracture 20 or secure the fusion/fixation device 10 flush to the bone 12. Thereafter, the application tool 52 may be used to sequentially bend or position the arms of the fixation/fusion device 10 around the fragments of the fracture 20 to achieve relative stability.

In some aspects, the fusion/fixation device 10 does not inherently provide axial compression that may be desired for a transverse fracture pattern. In those select situations, application of manual axial compression is possible due to clamping. Oblique and comminuted fractures do not require the application of axial compression, but do call for circumferential compression, which is inherently present in aspects of the fusion/fixation device 10 that are not present in traditional plate and screw fixation. Depending on the requisite compression, the fusion/fixation device 10 is contemplated as being applied with one hand while the other, free hand maintains reduction of the fracture 20.

Figure 14A:
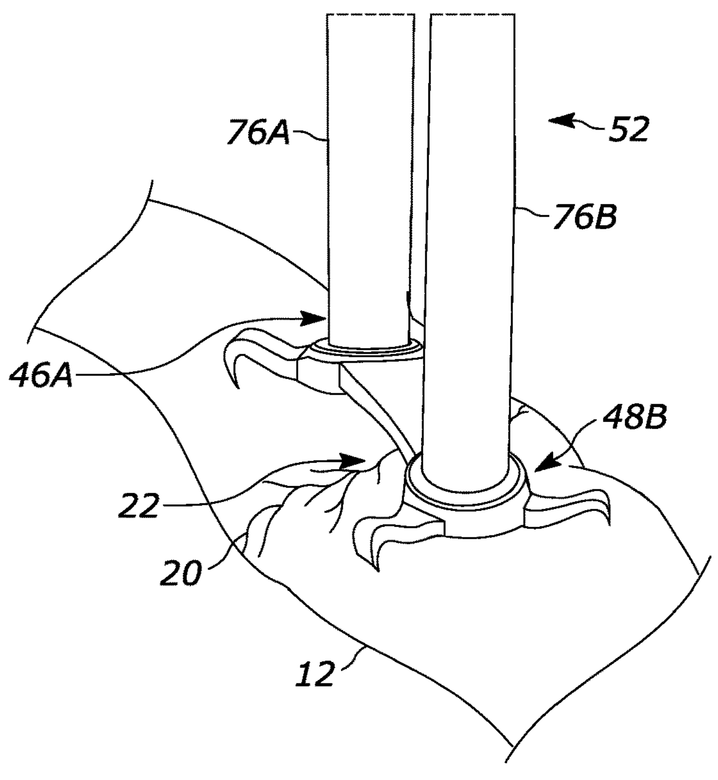
FIG. 14A is a perspective view of a fusion/fixation device coupled to an application tool for purposes of implantation according to an aspect of the disclosure.

In still other aspects of operation and with reference to FIG. 14A, the application of the fusion/fixation device 10 can be placed onto, implanted, or fixed on the desired target site of the bone 12 over the fracture 20 according to the following steps. As shown in FIG. 14A, the application tool 52 is coupled to the at least one opening 48 or the plurality of openings 48A, 48B. As shown in the illustrative example, the application tool 52 may comprise one or more of a bar and/or rod 76A, 76B configured to threadably, or otherwise, couple to the at least one opening 48.

Figure 14B:
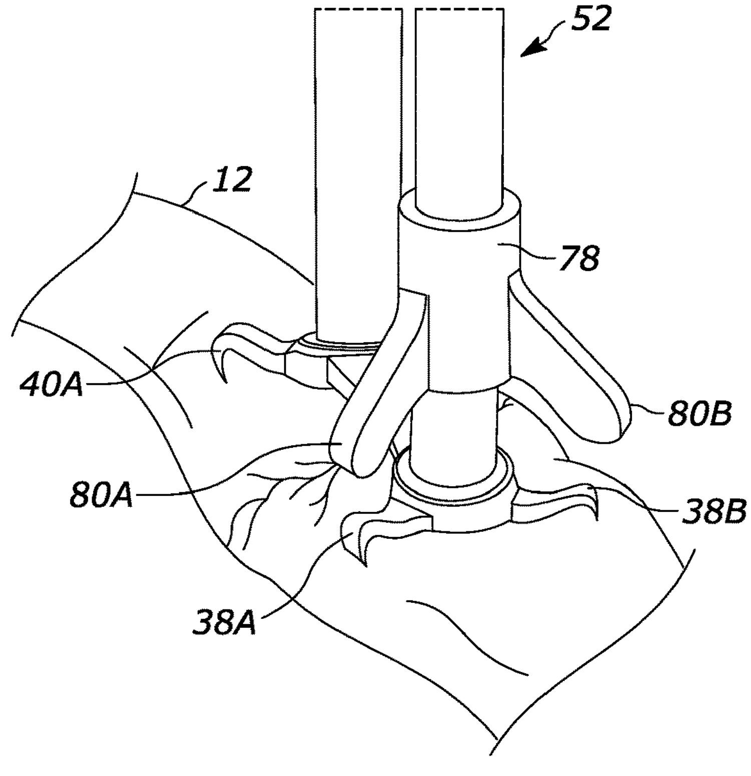
FIG. 14B is a perspective view of a fusion/fixation device of FIG. 14A in which an advancement tool is being advanced toward the fusion/fixation device according to an aspect of the disclosure.
Figure 14C:
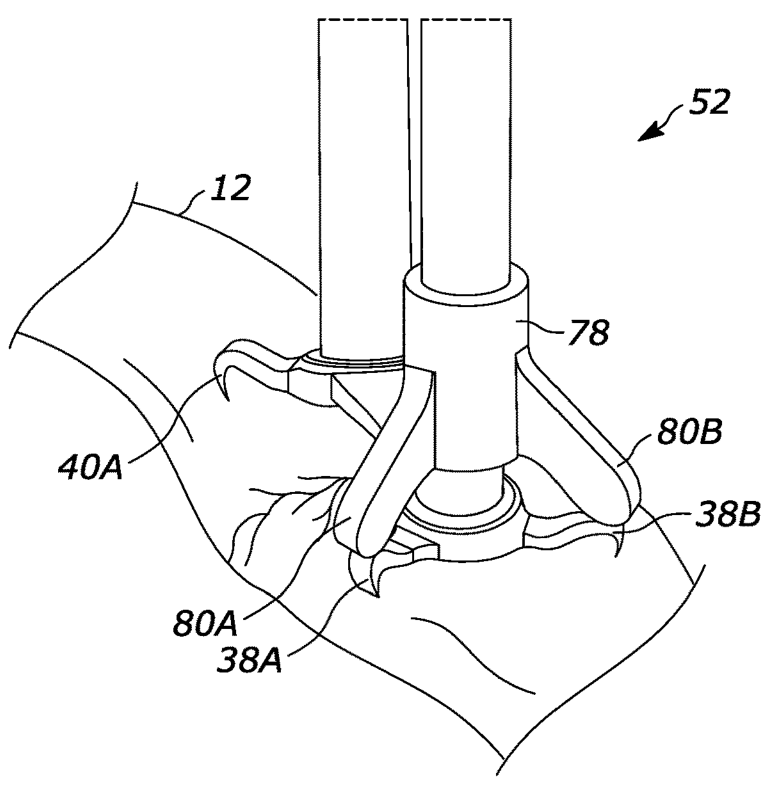
FIG. 14C is a perspective view of a fusion/fixation device of FIG. 14A in which an advancement tool urges the tines of the fusion/fixation device into a bone according to an aspect of the disclosure.

In further aspects, an advancement tool 78 is then advanced over the application tool 52 as shown in FIG. 14B. In some configurations, the advancement tool 78 has one or more protrusions 80A, 80B corresponding to the tines on the fusion/fixation device 10 (e.g., the proximal tines 38A, 38B). The advancement tool 78 advances distally along the application tool 52 until the one or more protrusions 80A, 80B are in contact with the tines (e.g., the proximal tines 38A, 38B), as shown in FIG. 14C.

Figure 14D:
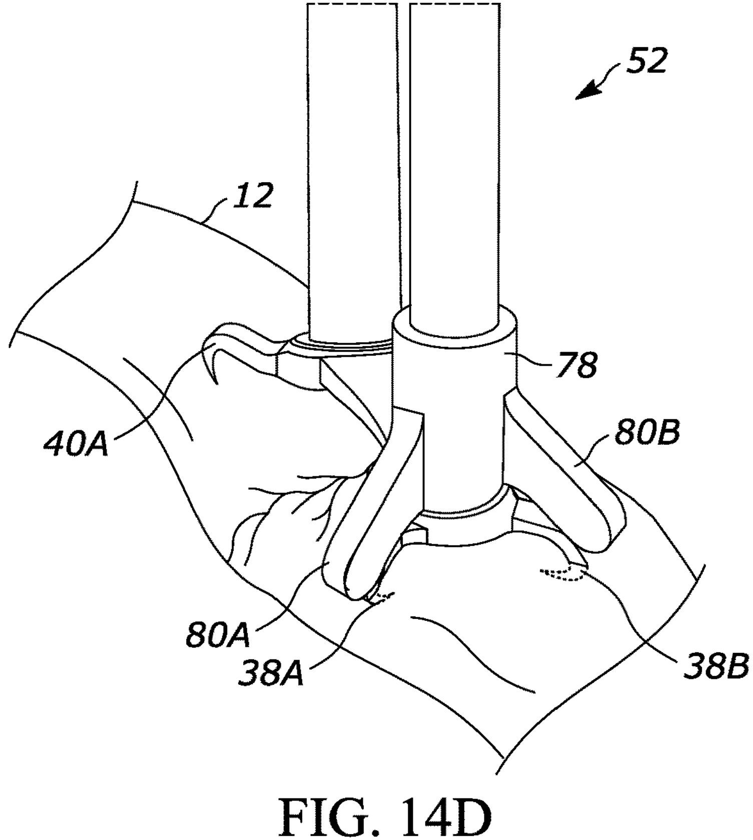
FIG. 14D is a perspective view of a fusion/fixation device of FIG. 14A in which an advancement tool is in contact with the fusion/fixation device according to an aspect of the disclosure.
Figure 14E:
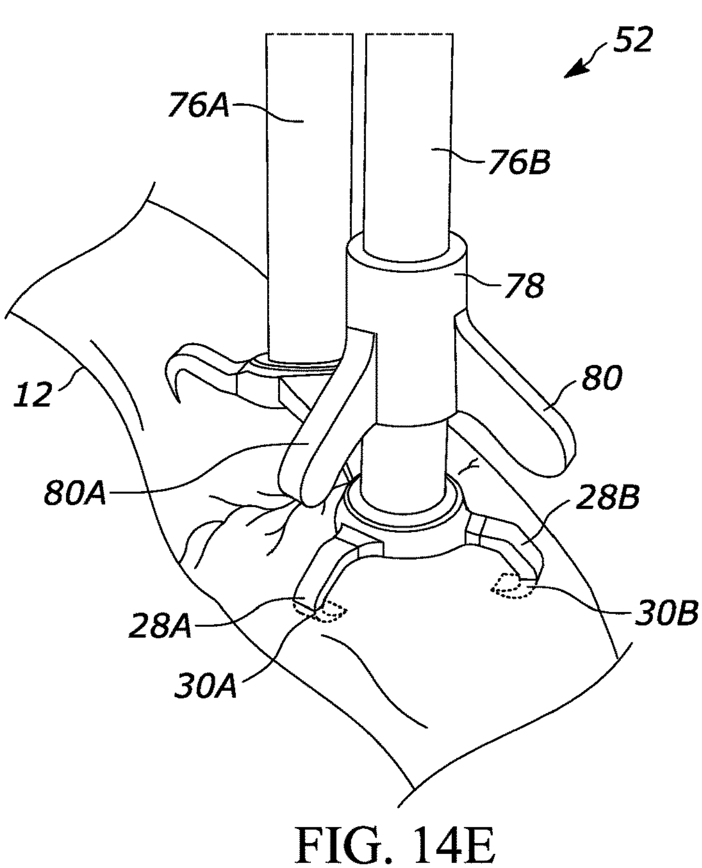
FIG. 14E is a perspective view of a fusion/fixation device of FIG. 14A in which an advancement tool is being removed according to an aspect of the disclosure.
Figure 14F:
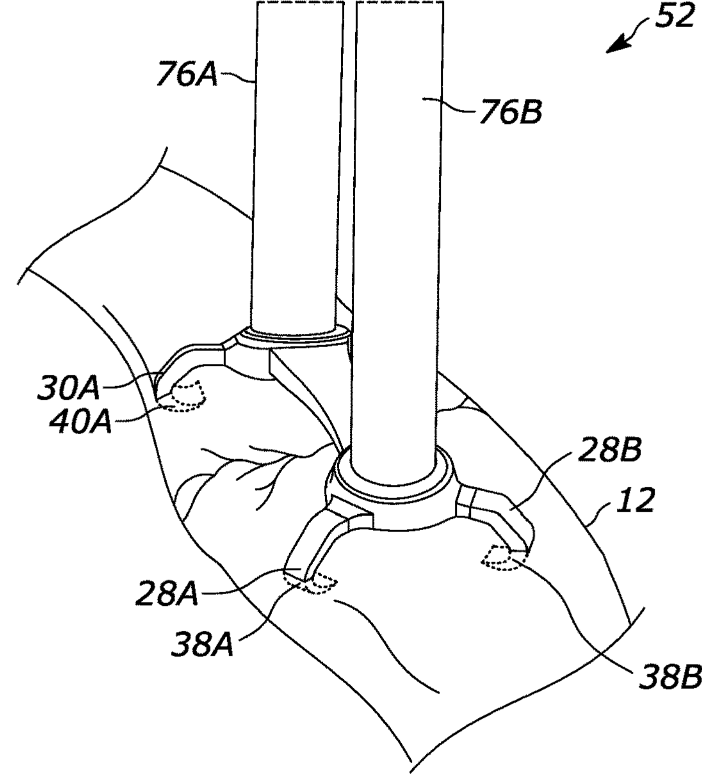
FIG. 14F is a perspective view of a fusion/fixation device of FIG. 14A in which the tines of the fusion/fixation device are embedded into a bone according to an aspect of the disclosure.
Figure 14G:
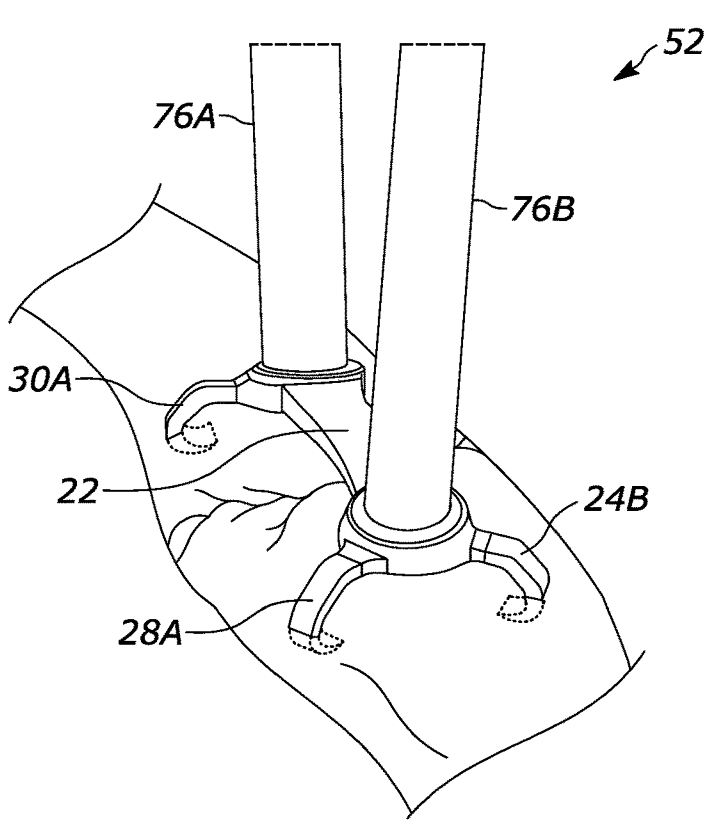
FIG. 14G is a perspective view of a fusion/fixation device of FIG. 14A in which two rods of an advancement tool are urged apart to bend the fusion/fixation device according to an aspect of the disclosure.
Figure 14H:
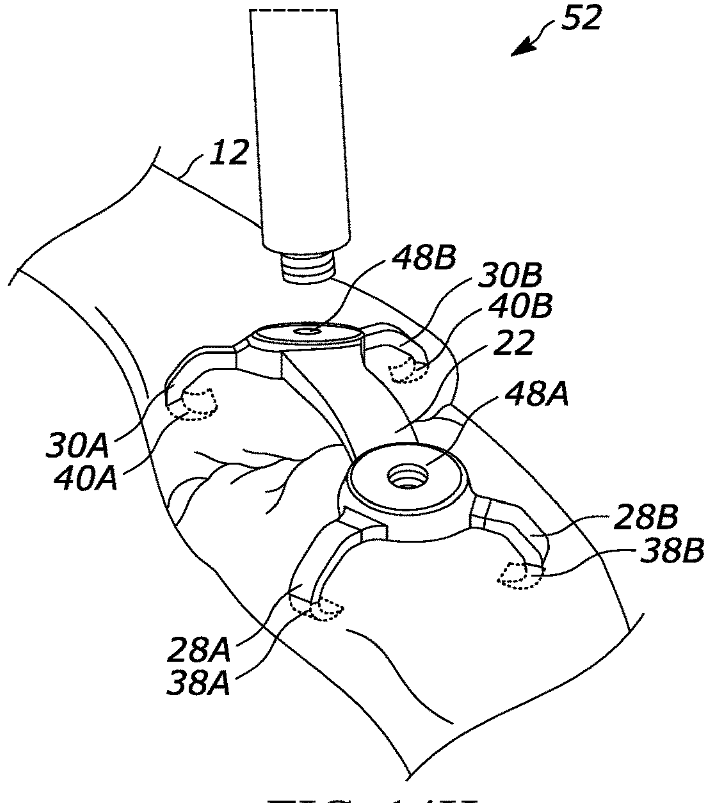
FIG. 14H is a perspective view of a fusion/fixation device of FIG. 14A in which an advancement tool is removed according to an aspect of the disclosure.
Figure 14I:
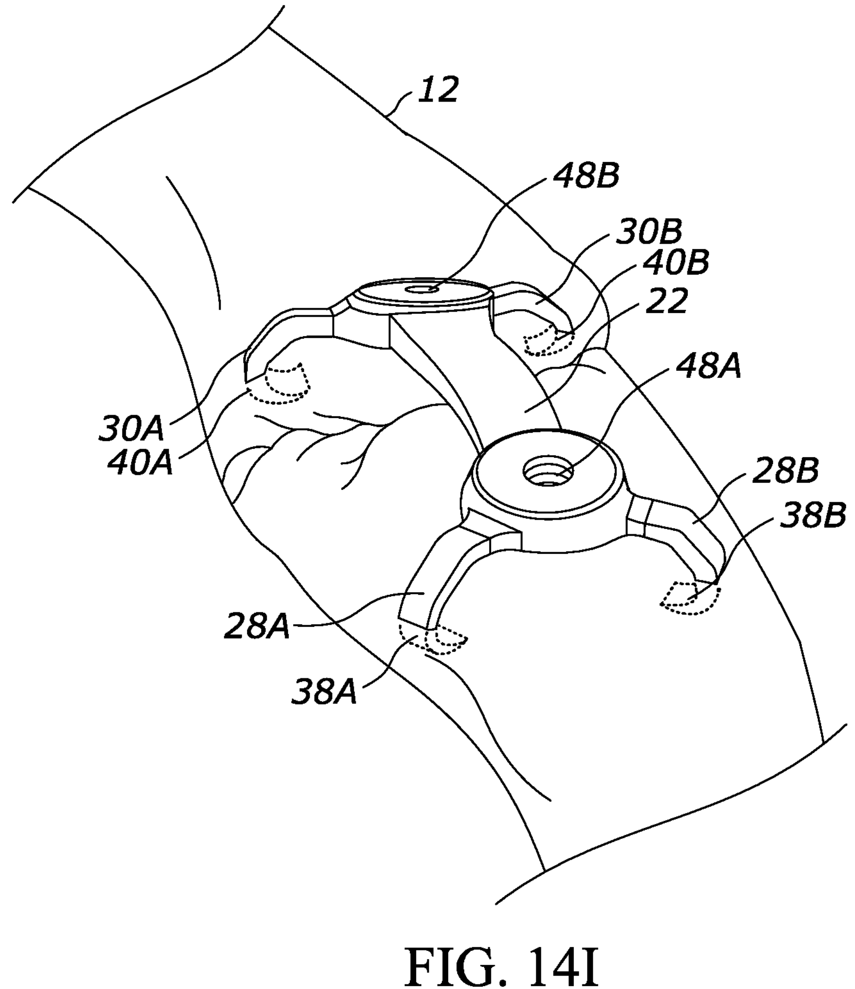
FIG. 14I is a perspective view of a fusion/fixation device of FIG. 14A in which an advancement tool is removed and the fusion and fixation device is implanted according to an aspect of the disclosure.

The advancement tool 78, in further aspects, is urged distally along the application tool 52 such that the one or more protrusions 80A, 80B urge the tines (e.g., the proximal tines 38A, 38B) of the fusion/fixation device into the bone 12 as shown in FIG. 14D, which may continue until the arms (e.g., the proximal arms 28A, 28B) are flush with the bone 12. Once the desired position is achieved, the advancement tool 78 is removed by proximal movement along the application tool 52 as shown in FIG. 14E. The advancement tool 78 may thereafter be used to repeat the process on the other off bar or rod of the application tool 52 as seen in FIG. 14F and FIG. 14G. Thereafter, the application tool 52 can be removed by decoupling from the at least one spine 22 of the fusion/fixation device 10 as seen in FIG. 14H such that only the fusion/fixation device 10 remains, as seen in FIG. 14I.

Figure 15A:
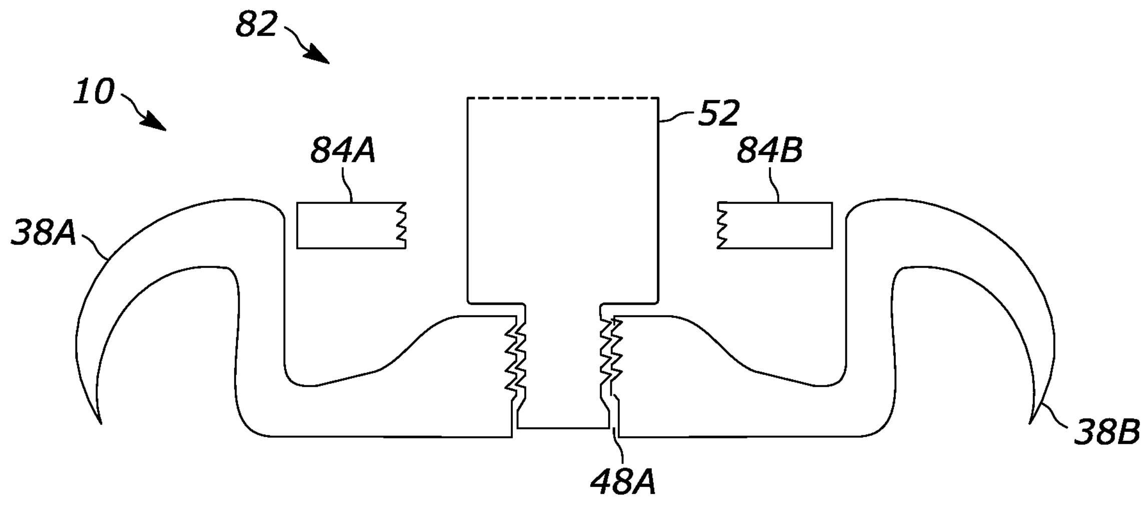
FIG. 15A is a perspective view of a fusion/fixation device coupled to an application tool for purposes of implantation according to an aspect of the disclosure.
Figure 15B:
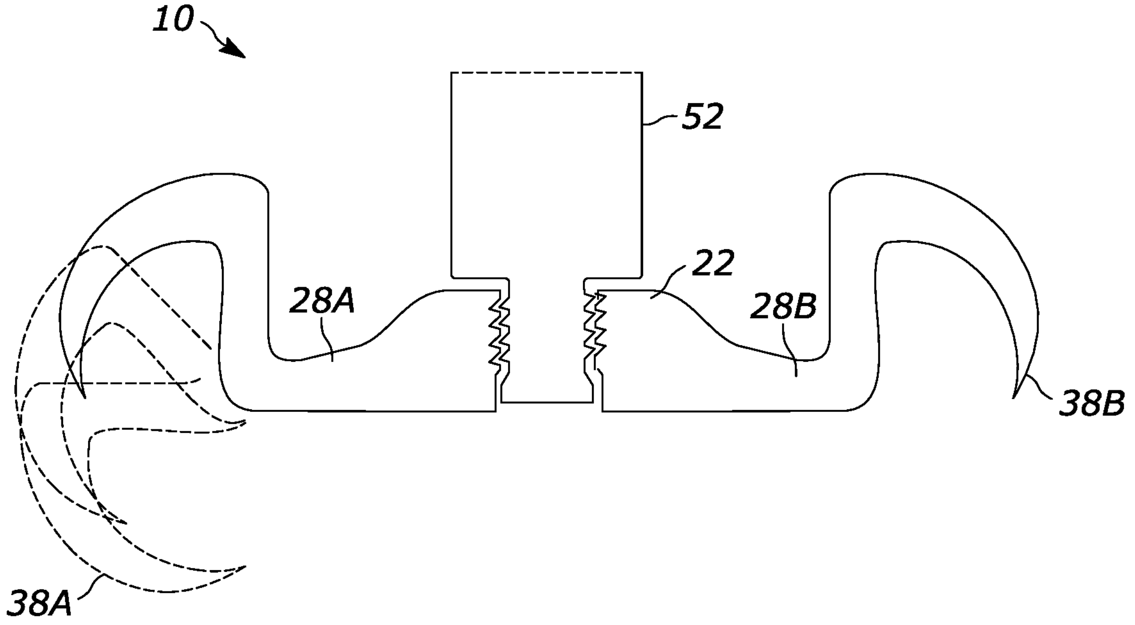
FIG. 15B is a perspective view of the fusion/fixation device of FIG. 15A in which an application tool is urging tines of the fusion/fixation device into a bone according to an aspect of the disclosure.

In still other aspects, FIGS. 15A and 15B show a cross-section cutaway of the fusion/fixation device 10 coupled to the application tool 52 according to aspects disclosed herein. A separate tine advancement tool 82 (schematically represented by the small projections 84A, 84B) is used to advance the fusion/fixation device 10 into the bone 12. The separate tine advancement tool 82, in such aspects, applies force away from the application tool 52 in a direction perpendicular to the longitudinal axis of the application tool 52, thereby urging the fusion/fixation device into the bone 12 as shown in FIG. 15B.

Figure 16A:
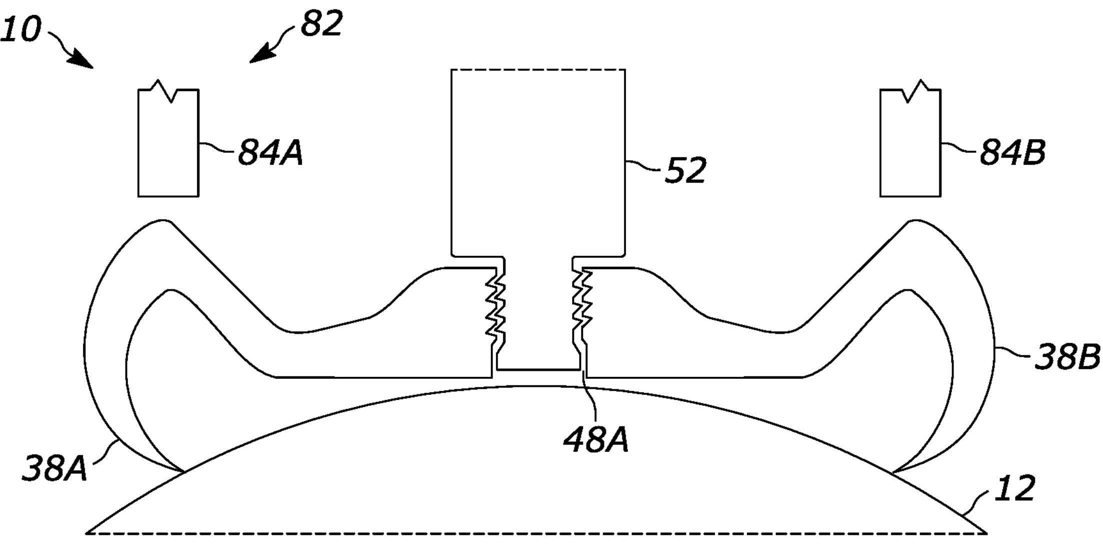
FIG. 16A is a perspective view of a fusion/fixation device coupled to an application tool for purposes of implantation according to an aspect of the disclosure.
Figure 16B:
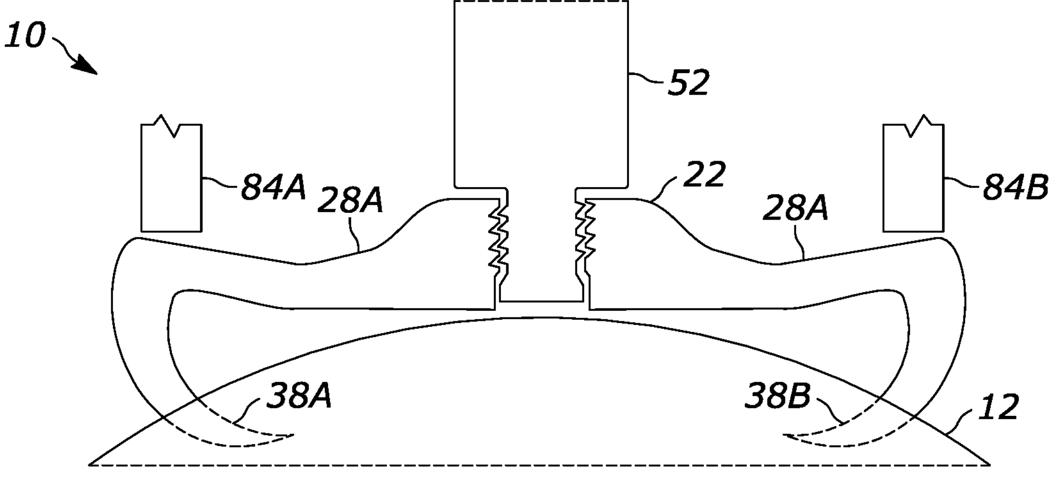
FIG. 16B is a perspective view of the fusion/fixation device of FIG. 16A in which an application tool is urging tines of the fusion/fixation device into a bone according to an aspect of the disclosure.

FIG. 16A and FIG. 16B depict a similar view of the fusion/fixation device 10 implantation using the application tool 52 according to another aspect of the disclosure. The separate tine advancement tool 82 is used to advance the fusion/fixation device 10 into the bone 12 by the separate tine advancement tool 82 applying force toward the bone 12 in a direction that is parallel to the longitudinal axis of the application tool 52, thereby urging the fusion/fixation device into the bone 12 as shown in FIG. 16B.

Figure 17A:
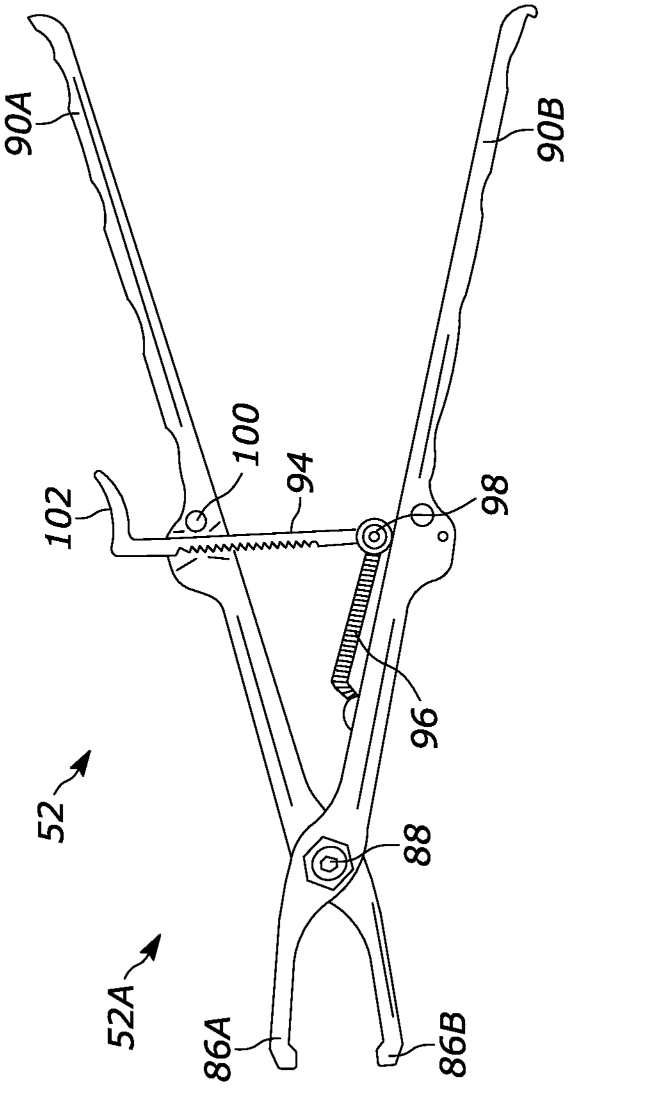
FIG. 17A is a front view of an implantation device according to an aspect of the disclosure.
Figure 17B:
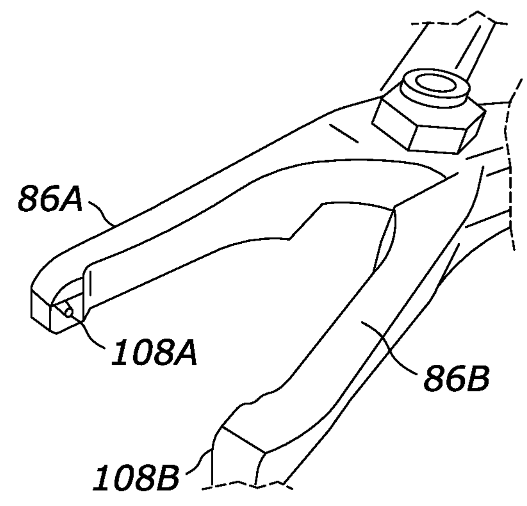
FIG. 17B is an expanded perspective view of a jaw of the implantation device of FIG. 17A according to an aspect of the disclosure.
Figure 17C:
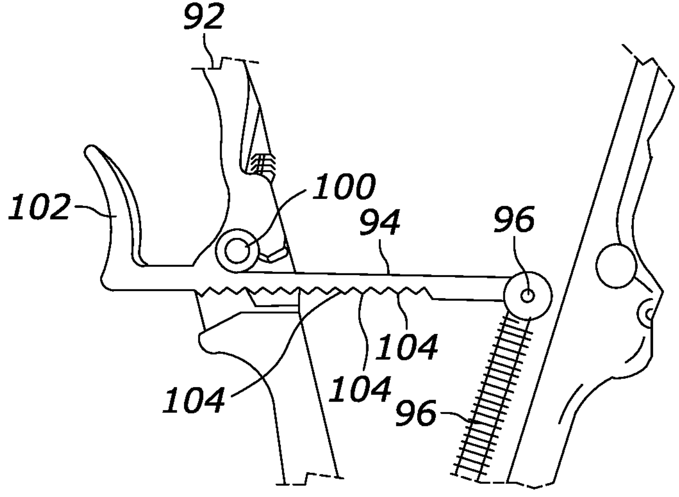
FIG. 17C is an expanded front view of a ratchet mechanism of the implantation device of FIG. 17A to an aspect of the disclosure.
Figure 17D:
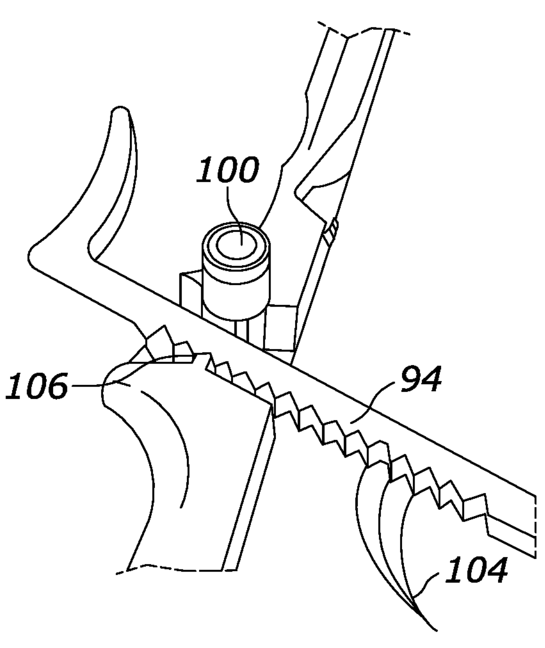
FIG. 17D is an expanded perspective view of a locking mechanism of the implantation device of FIG. 17A according to an aspect of the disclosure.
Figure 17E:
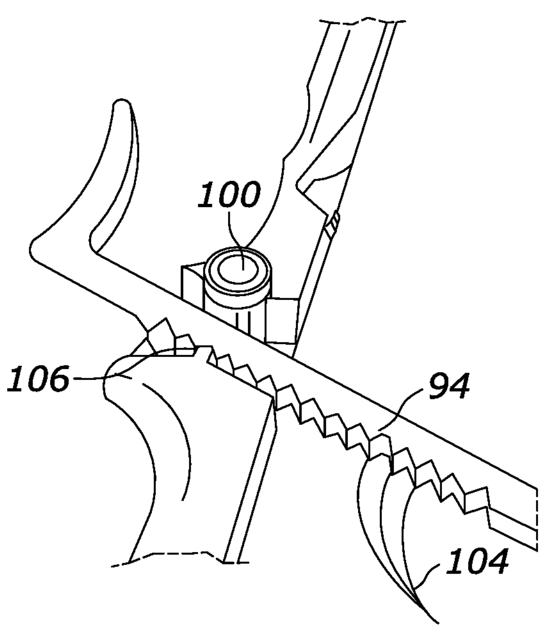
FIG. 17E is an expanded perspective view of a locking mechanism of the implantation device of FIG. 17A according to an aspect of the disclosure.

FIGS. 17A-17E depict aspects of the application tool 52, which in this embodiment is a pair of pliers 52A. The application tool 52 has a pair of jaws 86A, 86B, a jaw pivot 88, and a pair of handles 90A, 90B. As seen in FIG. 17C, the application tool 52 also has a ratchet mechanism 92 that includes a ratchet bar 94, a ratchet spring 96, a ratchet pivot 98, a locking mechanism 100, and a release mechanism 102. The ratchet spring 96 is configured to be tensioned to urge the ratchet bar 94 toward the ratchet spring 96, thereby urging a plurality of teeth 104 of the ratchet bar 94 toward a finger 106 (as shown in FIG. 17D and FIG. 17E) such that the finger 106 is positioned between two of the plurality of teeth 104 and retained in that position such that the ratchet bar 94 is retained in that position. The release mechanism 102 in some aspects is a release trigger that is moveable in relation to the finger 106, thereby allowing the pair of handles 90A, 90B to move in relation to each other.

As depicted in the illustrative example of FIG. 17B, the pair of jaws 86A, 88B have one or more device coupling feature 108A, 108B on an interior surface at the distal end of the pair of jaws 86A, 88A. The one or more device coupling feature 108A, 108B is configured to interface and couple with one or more of the fusion/fixture device 10 disclosed or contemplated herein. In certain aspects, the one or more coupling feature 108A, 108B is configured to couple to the tool interface feature 56A, 56B, 56C, **56*n* or the at least one opening 48 in the at least one spine 22. As shown, a first coupling feature 108A is a circular pin and a second coupling feature 108B is a square peg, of which each correspond and couple to the corresponding tool interface feature 56A, 56B, 56C, 56*n*, such that the fusion/fixation device 10 is locked in all degrees of freedom when coupled to the application tool 52. In other aspects, the one or more device coupling feature 108A, 108**B may be a singular feature that is non-circular, a multiple pin feature, or any other known feature for achieving the same effect.

FIGS. 17D and 17E depict further aspects of the locking mechanism 100. The locking mechanism 100 is a locking button that can be depressed by a user to move the locking mechanism 100 into and out of a locked position. FIG. 17D depicts the locking mechanism 100 in the unlocked position, while FIG. 17E depicts the locking mechanism 100 in the locked position in which the locking button is positioned to urge the ratchet bar 94 toward the finger 106 such that the finger 106 is positioned between two of the plurality of teeth 104, thereby engaging the ratchet bar 94 such that the pair of handles 90A, 90B are restrained from moving in relation to one another. The locking mechanism 100 can be depressed by the user to lock the pair of handles 90A, 90B into a specific orientation. When the locking mechanism 100 is employed to urge the ratchet bar 94 toward the finger 106, the entirety of the application tool 52 is rigidly fixed and cannot be released by actuating the release mechanism 102. When in the unlocked position and the release mechanism 102 is engaged (but the ratchet bar 94 is engaged), then the pair of handles 90A, 90B may be compressed or urged toward one another, but cannot be urged away from each other to cause the pair of jaws 86A, 86B to separate. If the locking mechanism 100 is in the unlocked position and the release mechanism 102 is actuated, then the pair of handles 90A, 90B may be compressed or released with respect to one another.

Figure 18:
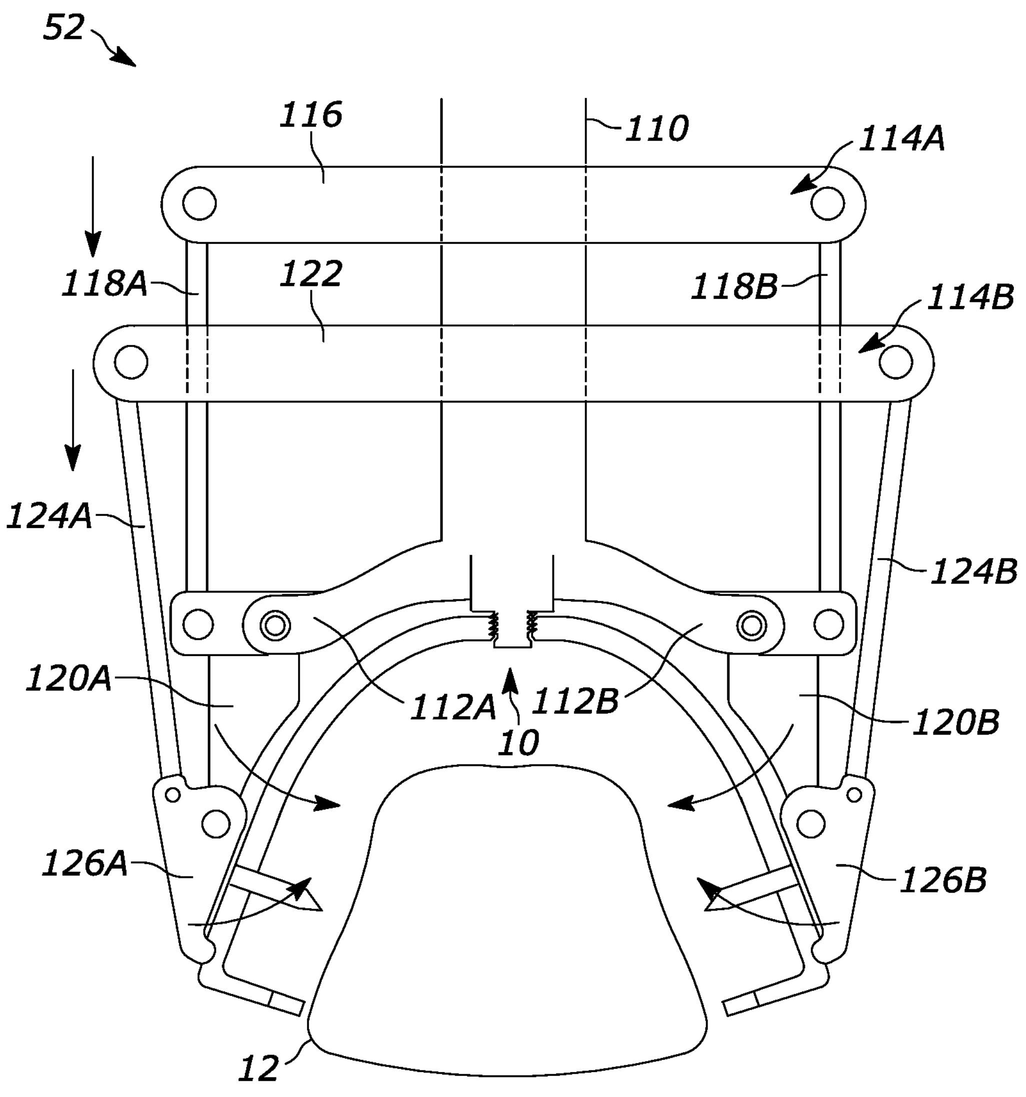
FIG. 18 is a side view of a fusion/fixation device coupled to an application tool for purposes of implantation according to an aspect of the disclosure.

FIG. 18 shows other aspects of the application tool 52. The application tool 52 has a central rod 110 with a pair of arms 112A, 112B at a distal end of the central rod 110. The application tool 52 positions or implants the fusion/fixation device 10 in two stages: first bending the arms to a certain point or position, and then applying a further bend that wraps the arms around the bone 12 even further. This is accomplished using at least a pair of deployment components 114A, 114B. One of the pair of deployment components 114A has a bar 116 coupled to a pair of links 118A, 118B that are coupled at their distal end to a first set of pivotal paddles 120A, 120B. The first of the first set of pivotal paddles 120A is pivotally coupled to the pair of arms 112A, 112B of the application tool 52, such that when the bar 116 of the first of the pair of deployment components 114A is urged downward, the distal end of the first of the first set of pivotal paddles 120A contact the arms of the fusion/fixation device 10 and bend the arms in a direction urging into the bone 12.

Thereafter, the second of the pair of deployment components 114B is deployed as follows. The second of the pair of deployment components 114B has a second bar 122 coupled to a second pair of links 124A, 124B that are coupled at their distal ends to a second set of pivotal paddles 126A, 126B. The second set of pivotal paddles 126A, 126B are pivotally coupled to the first set of pivotal paddles 120A, 120B, such that when the second bar 122 is urged downward, the distal ends of the second set of pivotal paddles 126A, 126B contact the arms of the fusion/fixation device 10 and further bend the arms such that they are more fully wrapped around the bone 12 as indicated by FIG. 18.

It is hereby contemplated that the any of the fusion/fixation device 10 disclosed or contemplated herein can be bent or otherwise deformed along the at least one spine 22 into a curved configuration. Deformation of the at least one spine 22 can occur at any time (from the manufacturing process forward).

Figure 19A:
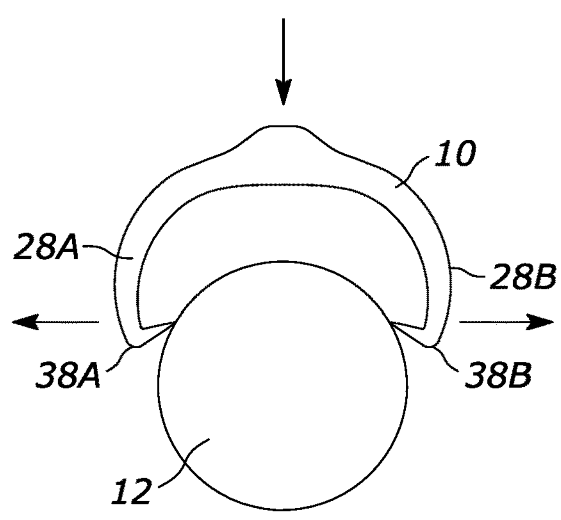
FIG. 19A is a side view of a fusion/fixation device positioned adjacent a bone according to an aspect of the disclosure.
Figure 19B:
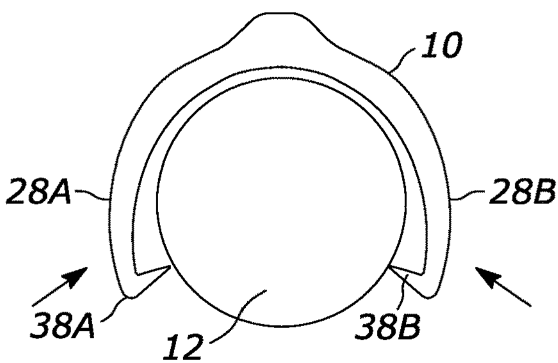
FIG. 19B is a side view of a fusion/fixation device of FIG. 19A in which the fusion/fixation device has been positioned around the bone according to an aspect of the disclosure.
Figure 19C:
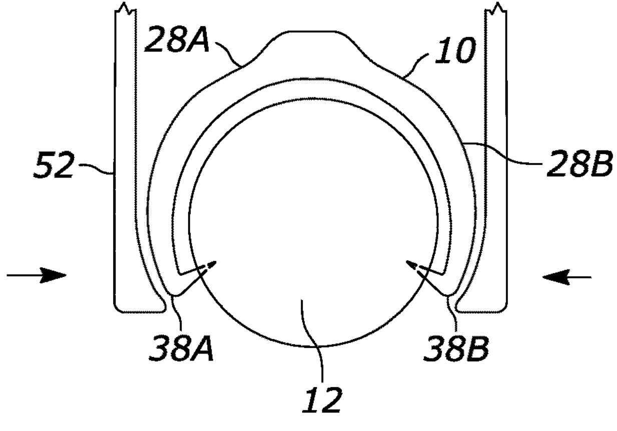
FIG. 19C is a side view of a fusion/fixation device of FIG. 19A in which an application tool is urging the tines of the fixation/fusion device into the bone according to an aspect of the disclosure.

FIGS. 19A-19C depict a cross-section cutaway view of the fusion/fixation device 10 according to further aspects of the disclosure that is advanced over the target site of the bone 12 and then fixed in place. As understood, the fusion/fixation device 10 can be of one or more of the aspects disclosed herein. As depicted, the fusion/fixation device 10 is semi-rigid, meaning that it has enough flexibility to allow the arms (e.g., the proximal arms 28A, 28B) to flex outwardly as shown by the arrows in FIG. 19A, thereby allowing the fusion/fixation device 10 to be advanced to a desired position on the bone 12 as shown in FIG. 19B. Thereafter, the application tool 52 and/or the advancement tool 78 is then positioned such that the arms of the application tool 52 and/or advancement tool 78 are positioned against the arms of the fusion/fixation device 10 (e.g., the proximal arms 28A, 28B). The application tool 52 and/or advancement tool 78 is then actuated to urge the tines of the fusion/fixation device 10 (e.g., the proximal tines 38A, 38B) into the bone 12 as shown in FIG. 19C.

Figure 1B:
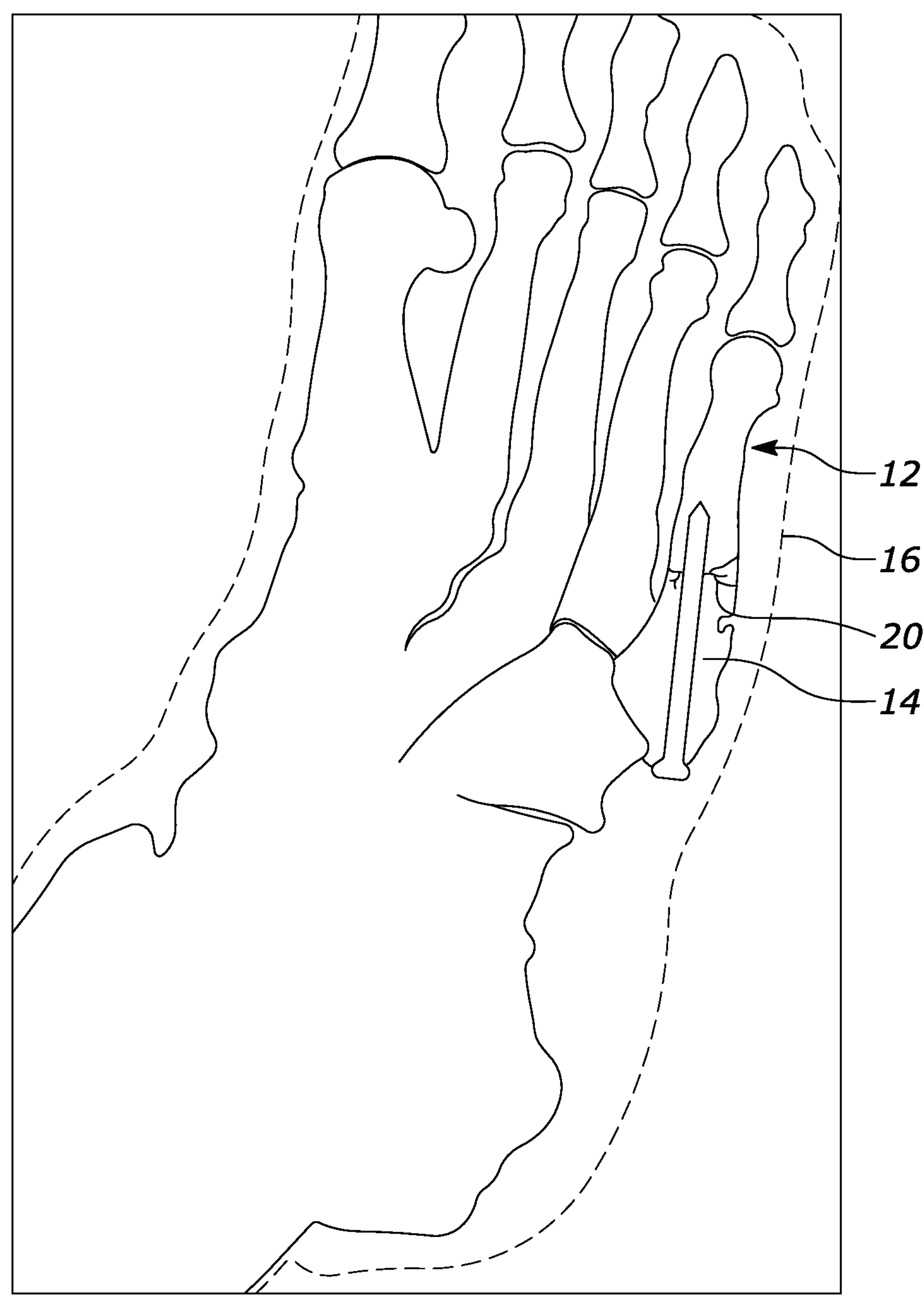
FIG. 1B is a front view of an X-ray of a known screw fixation positioned in an affected digit.
Figure 1C:
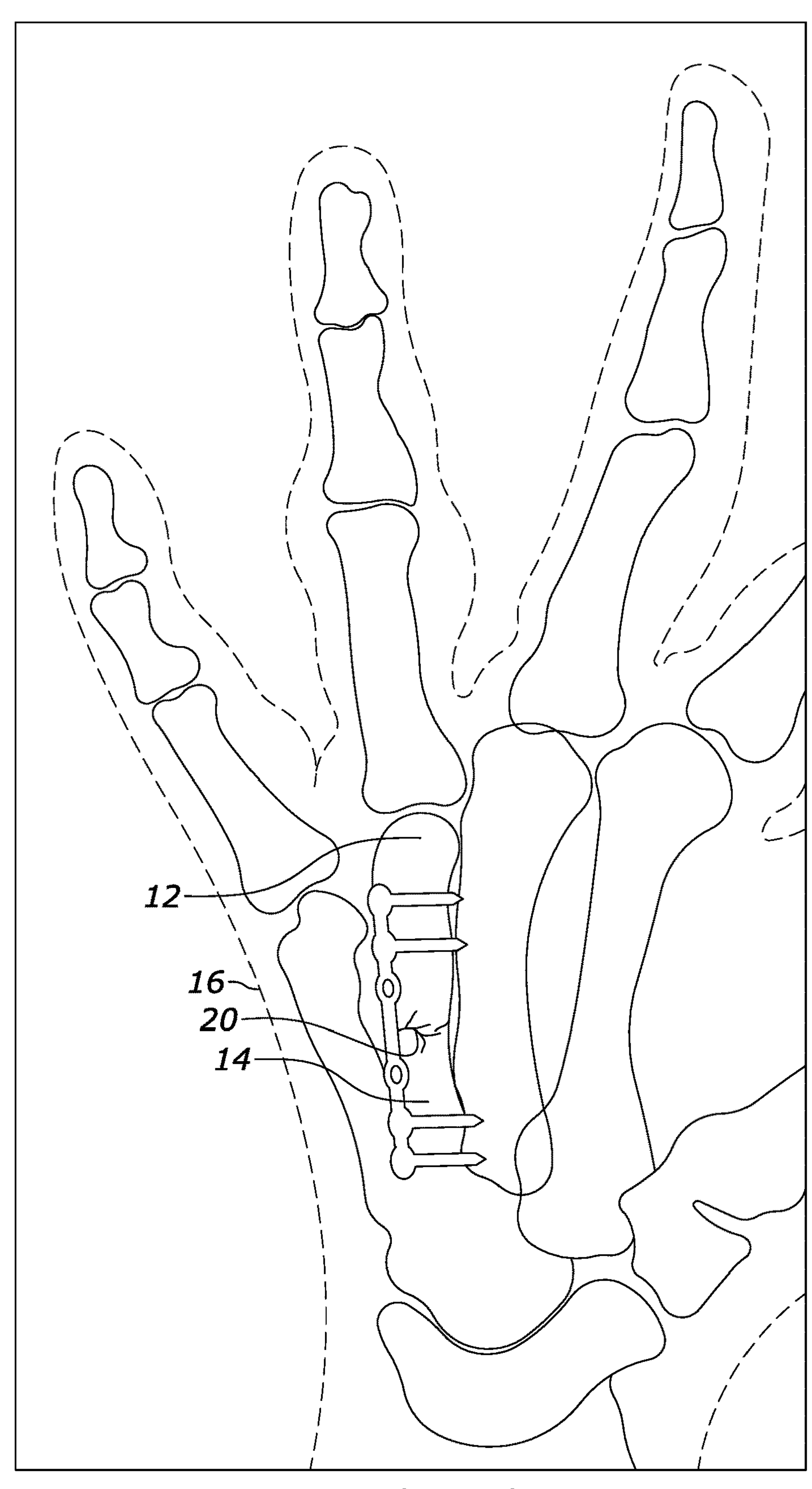
FIG. 1C is a front view of an X-ray of a known plate fixation positioned in an affected digit.
Figure 2A:
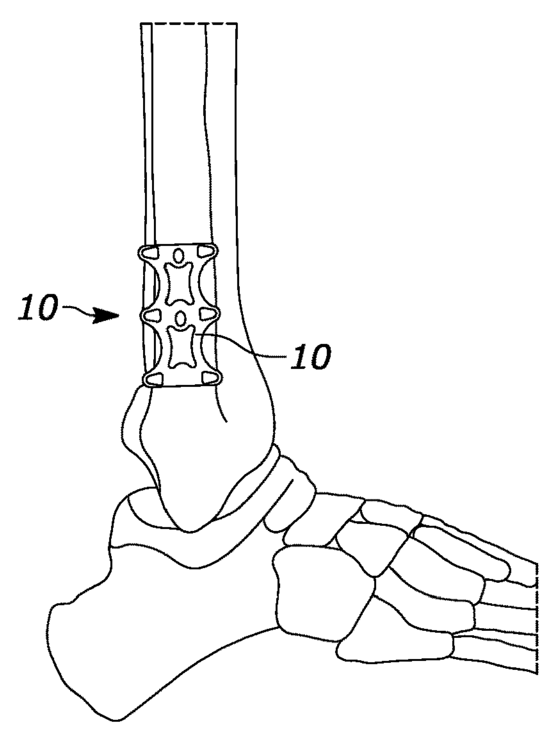
FIG. 2A is a side view of a fusion/fixation device affixed to a target site on a bone according to an aspect of the disclosure.
Figure 2B:
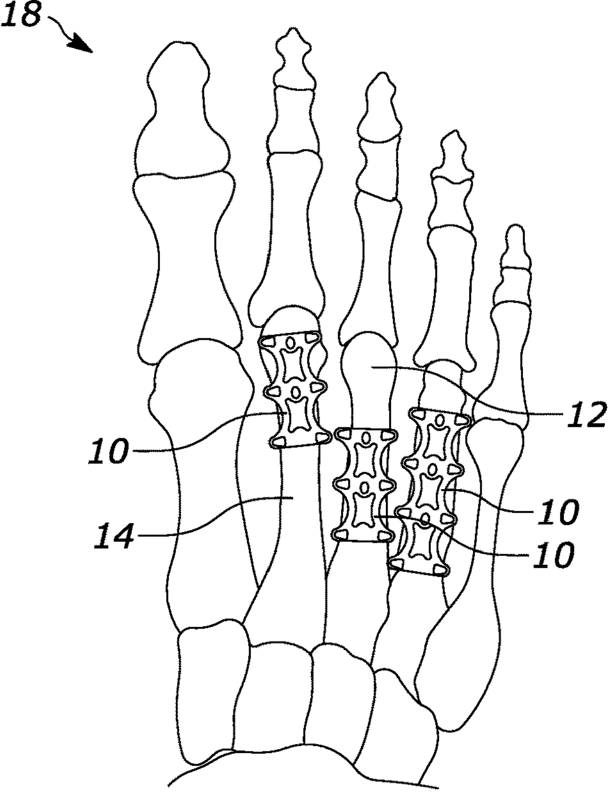
FIG. 2B is a top view of fusion/fixation devices affixed to target sites on bones of a foot according to one or more aspect of the disclosure.
Figure 2C:
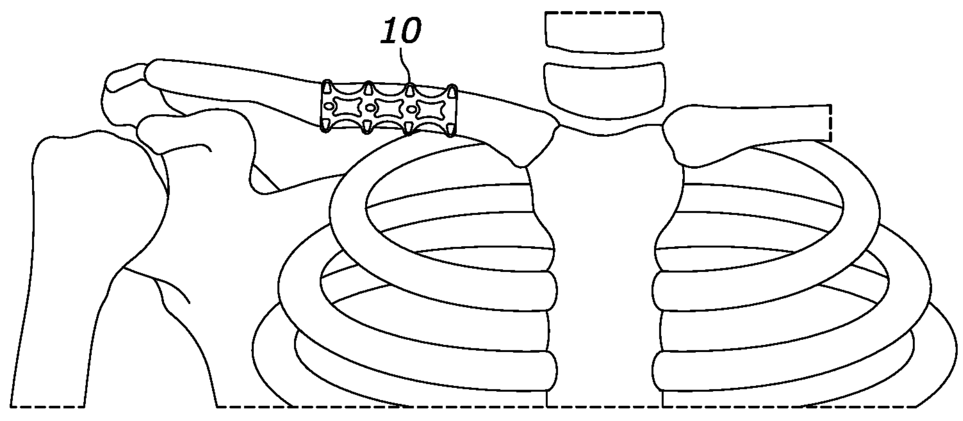
FIG. 2C is a front view of a fusion/fixation device affixed to a target site on a bone according to an aspect of the disclosure.
Figure 2D:
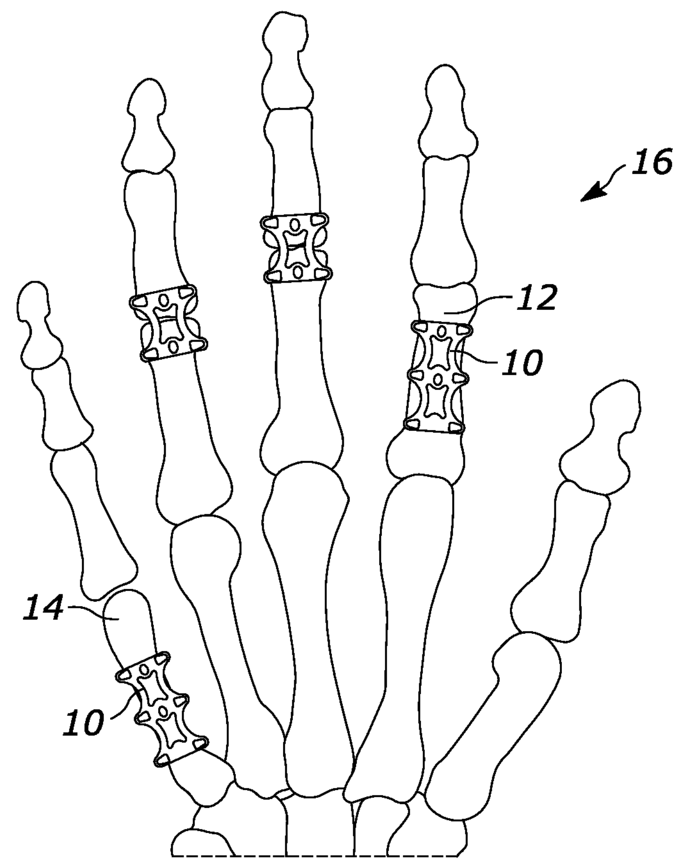
FIG. 2D is a top view of fusion/fixation devices affixed to target sites on bones according to one or more aspect of the disclosure.
Figure 2E:
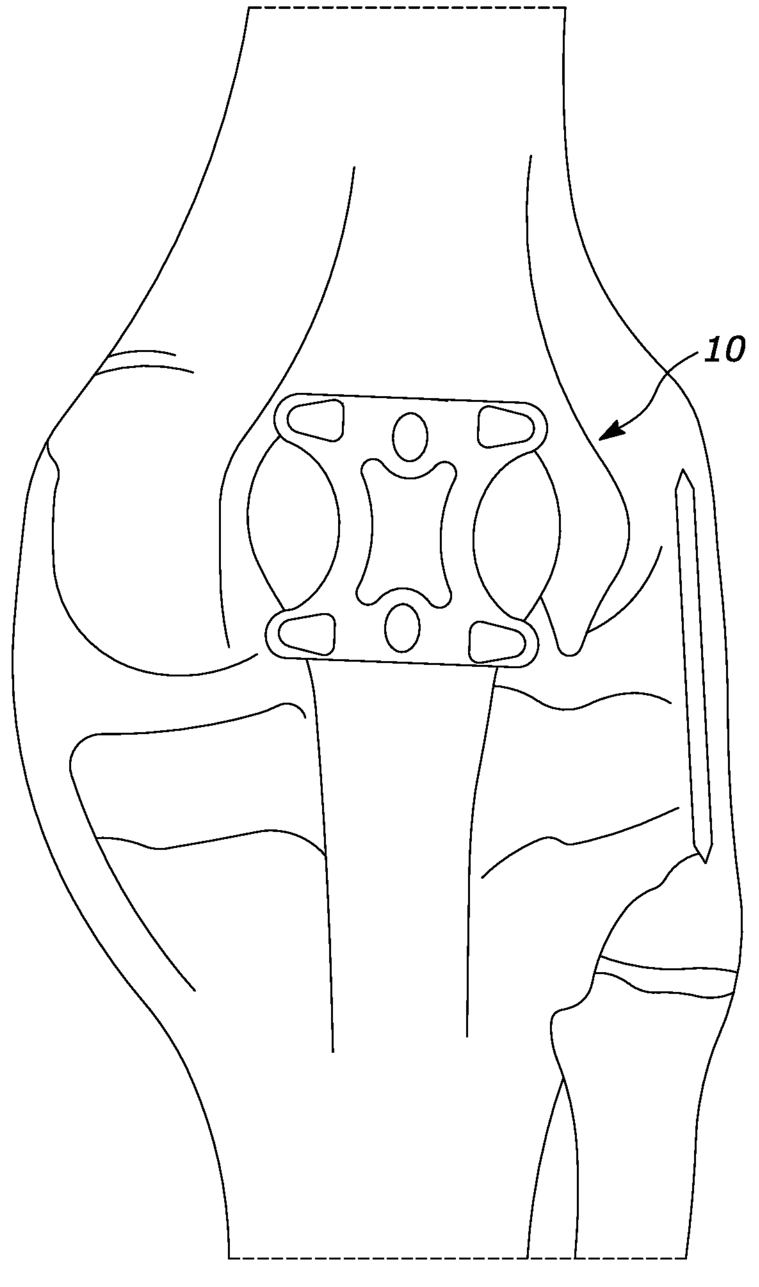
FIG. 2E is a side view of a fusion/fixation device affixed to a target site on a bone according to an aspect of the disclosure.

Some of the advantages of certain embodiments disclosed herein include the following. The device is presented to span a zone of a fractured metatarsal, metacarpal, or phalangeal bone via one or more spine with three or more pairs of arms extending peripherally from the at least one spine in a direction substantially perpendicularly to the one or more spines. As such, the device spans an appropriate length for repair of a fractured long bone of the hand and/or foot. Further, the variable length of the pair of arms allows for the device to wrap or capture various bone anatomy related to thickness, height, and diameter in addition to variable fracture pattern or patterns. Further still, the thickness of the device provides strength to the fixation construct without concern given the depth in which the device is positioned within the body commonly associated with this tissue. Further, the device is quickly applied akin to a K-wire (shown in FIG. 1A) without the disadvantage of premature loosening or percutaneous application. Further still, the device provides a span akin to plate fixation (shown in FIG. 1C) without the need for drill holes in the bone or requiring the number of plate shapes and sizes to address different fracture compositions and patterns. Further, the device provides for repair of fracture fragments that are too small to accept screw fixation (as depicted in FIG. 1B)—i.e., comminuted fracture situations. Further still, the device provides a broad capture or "footprint" that allows capture of multiple fragments in comminuted fractures. Further, the device provides dorsal, medial, lateral, and plantar fixation which translated to osteotomies.

Further, certain embodiments provide the benefits of an extra-medullar placement without the drawbacks of using mounting hardware such as screws. Some devices disclosed herein can be positioned and affixed so that they are stable using one of the application tools disclosed or contemplated herein. In addition, certain implementations herein are configured to be utilized as the sole means of fusion/fixation and can be utilized in conjunction with an additional provisional or planned adjunctive intramedullary "K-wire" per the clinical need and/or surgeon preference.

In some implementations, the specific position, dimension and relationship of the tines provide anatomic specific mechanical stability; including the angle of any arm or pair of arms discussed herein with respect to the centerline extending through the at least one spine. Furthermore, the anatomic position of the intended site can modulate to a patient specific position.

As discussed above, the various embodiments herein may be used in conjunction with a "K-Wire" or other intramedullar device. The intramedullar device may be placed prior to the application of the device embodiment to aide in the alignment. After the device embodiment has been engaged, the intramedullar device may be removed immediately, removed after a prescribed healing period or left in permanently depending on the type used.

The various embodiments may also be used in conjunction with known fasteners. In certain embodiments, the device can incorporate specialized holes for the use of fasteners when additional support or fixation is required in specific areas. Additionally the device embodiments can be used in conjunction with a screw placed in the central axis of the bone.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to embodiments, persons skilled in the art will recognize that changes may be made in form and detail without departing from the spirit and scope of the invention. The description is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. A bone fusion/fixation device comprising:

at least one spine;

at least two proximal arms extending from a proximal end of the at least one spine, each of the at least two proximal arms comprising at least one proximal tine, wherein the at least two proximal arms are configured to be positionable around a bone;

at least two distal arms extending from a distal end of the at least one spine, each of the at least two distal arms comprising at least one distal tine, wherein the at least two distal arms are configured to be positionable around the bone; and at least two medial arms extending from the at least one spine between the at least two distal arms and the at least two proximal arms, each of the at least two medial arms comprising at least one medial tine, wherein the at least two medial arms are configured to be positionable around the bone.

2. The bone fusion/fixation device of claim 1 further comprising at least one opening defined in the bone fusion/fixation device, wherein the at least one opening is sized and shaped to receive a portion of an application tool.

3. The bone fusion/fixation device of claim 1 further comprising each of the at least two medial arms comprising at least one deformation feature, wherein the at least one deformation feature is configured to facilitate deformation of the at least two medial arms.

4. The bone fusion/fixation device of claim 1 wherein the at least one medial tine is positioned at a radius of curvature that is more acute than a radii of curvature within the at least two medial arms.

5. The bone fusion/fixation device of claim 1 wherein the at least one spine comprises a first spine and a second spine, wherein the first spine and the second spine each have an inner curved edge.

6. The bone fusion/fixation device of claim 5 further comprising the inner curved edge of the first spine and the second spine extending from a spine corner, wherein the spine corner is configured to facilitate stability and are radiused to prevent fatigue fracture of the at least one spine.

7. The bone fusion/fixation device of claim 1 further comprising the at least two proximal arms comprising at least one proximal mid tine positioned proximally on the at least two proximal arms.

8. The bone fusion/fixation device of claim 7 further comprising the at least two distal arms comprising at least one distal mid tine positioned distally on the at least two distal arms.

9. The bone fusion/fixation device of claim 1 further comprising the at least two medial arms comprising at least one tool interface feature.

10. The bone fusion/fixation device of claim 1 wherein the bone fusion/fixation device is configured to be positioned over a target site;

wherein the target site is selected from a group consisting of an osteotomy of the bone and a fracture of the bone;

wherein the bone is selected from a group consisting of the bone of a foot, a digital bone of the foot, a long bone of the foot, the bone of a hand, the digital bone of the hand, and the long bone of the hand.

11. The bone fusion/fixation device of claim 1 wherein the at least two proximal arms extend outwardly in an acute angle formed by the at least one spine and each of the at least two proximal arms, respectively; and wherein the at least two proximal arms extend proximally forward of the proximal end of the at least one spine.

12. The bone fusion/fixation device of claim 1 wherein the at least two distal arms extend outwardly in an acute angle formed by the at least one spine and each of the at least two distal arms, respectively; and wherein the at least two distal arms extend distally forward of the distal end of the at least one spine.

13. The bone fusion/fixation device of claim 1 further comprising at least two second medial arms extending from the at least one spine between the at least two distal arms and the at least two medial arms, each of the at least two second medial arms comprising at least one second medial tine, wherein the at least two second medial arms are configured to be positionable around the bone.

14. The bone fusion/fixation device of claim 13 wherein the at least two proximal arms and the at least two distal arms extend a first distance away from the at least one spine, and the at least two medial arms and the at least two second medial arms extend a second distance away from the at least one spine; wherein the first distance and the second distance are not equal.

15. A bone fusion/fixation method, comprising:

providing a bone fusion/fixation device comprising:

(a) at least one spine;

(b) at least one proximal structure extending from a proximal end of the at least one spine, the at least one proximal structure comprising at least one proximal tine, wherein the at least one proximal structure is configured to be positionable around a bone;

(c) at least one distal structure extending from a distal end of the at least one spine, the at least one distal structure comprising at least one distal tine, wherein the at least one distal structure is configured to be positionable around the bone; and (d) at least one medial structure extending from the at least one spine between the at least one proximal structure and the at least one distal structure, wherein the at least one medial structure comprising at least one medial tine, wherein the at least one medial structure is configured to be positionable around the bone;

positioning the at least one proximal structure, the at least one distal structure, and the at least one proximal structure around a target site of the bone, wherein the bone is a single bone;

crimping the bone fusion/fixation device with an application tool such that the at least one proximal tine, the at least one distal tine, and the at least one distal tine are urged into the bone; and fixing the bone about the target site with the bone fusion/fixation device in a desired anatomical alignment.

16. The bone fusion/fixation method of claim 15 wherein the target site is selected from a group consisting of an osteotomy of the bone and a fracture of the bone; and wherein the bone is selected from a group consisting of the bone of a foot, a digital bone of the foot, a long bone of the foot, the bone of a hand, the digital bone of the hand, and the long bone of the hand.

17. The bone fusion/fixation method of claim 15 further comprising (e) at least one arm deformation feature defined in at least one of the at least one medial structure, wherein the at least one arm deformation feature is configured to facilitate deformation of the at least one medial structure.

18. The bone fusion/fixation method of claim 15 further comprising (e) at least one second medial structure extending from the at least one spine between the at least one medial structure and the at least one distal structure, wherein the at least one second medial structure comprising at least one second medial tine, wherein the at least one second medial structure is configured to be positionable around the bone.

19. The bone fusion/fixation method of claim 18 wherein the at least one proximal structure and the at least one distal structure extend a first distance away from the at least one spine, and the at least one medial structure and the at least one second medial structure extend a second distance away from the at least one spine; wherein the first distance and the second distance are not equal.

20. The bone fusion/fixation method of claim 15 wherein the at least one proximal structure extends outwardly in an acute angle formed by the at least one spine and the at least one proximal structure and wherein the at least one proximal structure extends proximally forward of the proximal end of the at least one spine; and wherein the at least one distal structure extends outwardly in an acute angle formed by the at least one spine and the at least one distal structure and wherein the at least one distal structure extends distally forward of the distal end of the at least one spine.

21. A method of making a bone fusion/fixation device, the method comprising:

forming a flat structure of bendable material, the flat structure comprising;

(a) at least one spine;

(b) at least one proximal structure extending from a proximal end of the at least one spine, the at least one proximal structure comprising at least one proximal tine;

(c) at least one distal structure extending from a distal end of the at least one spine, the at least one distal structure comprising at least one distal tine; and (d) at least one medial structure extending from the at least one spine between the at least one proximal structure and the at least one distal structure, wherein the at least one medial structure comprising at least one medial tine; and deforming the at least one medial tine such that the at least one medial tine is disposed at an angle greater than 0 degrees in relation to the at least one medial structure.

22. The method of making a bone fusion/fixation device of claim 21 further comprising (e) at least one second medial structure extending from the at least one spine between the at least one medial structure and the at least one distal structure, the at least one second medial structure comprising at least one second medial tine.

23. The method of making a bone fusion/fixation device of claim 21 further comprising (e) at least one opening defined in the flat structure, wherein the at least one opening is sized and shaped to receive a portion of an application tool.

* * * * *